(12) United States Patent
Cogan et al.

(10) Patent No.: US 7,166,628 B2
(45) Date of Patent: *Jan. 23, 2007

(54) CYTOKINE INHIBITORS

(75) Inventors: Derek A. Cogan, Sandy Hook, CT (US); Ming-Hong Hao, Ridgefield, CT (US); Kevin Chungeng Qian, New Milford, CT (US); Alan David Swinamer, Bethel, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 214 days.

This patent is subject to a terminal disclaimer.

(21) Appl. No.: 10/718,380

(22) Filed: Nov. 20, 2003

(65) Prior Publication Data

US 2004/0102492 A1    May 27, 2004

Related U.S. Application Data

(60) Provisional application No. 60/430,519, filed on Nov. 27, 2002.

(51) Int. Cl.
*A61K 31/41* (2006.01)
*C07D 249/04* (2006.01)

(52) U.S. Cl. ...................................... 514/383; 548/255
(58) Field of Classification Search ................ 548/255; 514/383
See application file for complete search history.

(56) References Cited

U.S. PATENT DOCUMENTS

| | | | |
|---|---|---|---|
| 6,319,921 B1 | 11/2001 | Cirillo et al. | |
| 2001/0044445 A1 | 11/2001 | Bamaung et al. | |
| 2005/0153972 A1* | 7/2005 | Cogan et al. | 514/252.05 |
| 2005/0256113 A1* | 11/2005 | Cogan et al. | 514/230.5 |

FOREIGN PATENT DOCUMENTS

| | | |
|---|---|---|
| DE | 4302051 A1 | 7/1994 |
| WO | WO 96/32382 | 10/1996 |
| WO | WO 00/18738 | 4/2000 |
| WO | WO 00/24735 | 5/2000 |
| WO | WO 03/022820 | 3/2003 |
| WO | WO 03/029210 A2 | 4/2003 |
| WO | WO 03/030902 A1 | 4/2003 |
| WO | WO 03/063781 A2 | 8/2003 |

OTHER PUBLICATIONS

Tsuboi et al., 2002, CAS: 137:263038.*
DE 4302051: Abstract for Correspondent EP 0608858.
* cited by examiner

*Primary Examiner*—Joseph K. McKane
*Assistant Examiner*—Robert Shiao
(74) *Attorney, Agent, or Firm*—Michael P. Morris; Anthony P. Bottino; Philip I. Datlow

(57) ABSTRACT

Disclosed are compounds of formula (I)

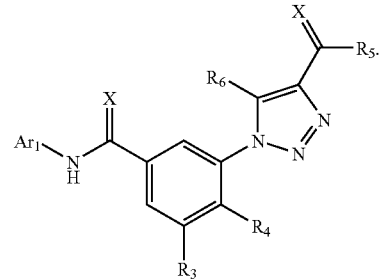

Where $Ar_1$, X, $R_3$, $R_4$, $R_5$ and $R_6$ are defined herein. The compounds of the invention inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

13 Claims, No Drawings

CYTOKINE INHIBITORS

RELATED APPLICATION DATA

This application claims benefit to U.S. provisional application No. 60/430,519 filed Nov. 27, 2002.

1. TECHNICAL FIELD

This invention relates to compounds of formula (I)

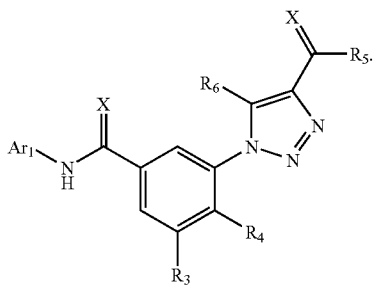

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

2. BACKGROUND INFORMATION

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). Studies suggest that inflammatory changes mediated by cytokines may be involved in endothelial cell pathogenesis including restenosis after percutaneous transluminal coronary angioplasty (PTCA) (Tashiro, H., et al., 2001 March, *Coron Artery Dis* 12(2):107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol*. 109, 54). IL-1 and TNF are both involved in periodontal disease. The destructive process associated with periodontal disease may be due to a disregulation of both IL-1 and TNF (Howells, 1995, *Oral Dis*. 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med*., 35, 26). TNFα has also been implicated in cachexia and muscle degradation, associated with HIV infection (Lahdiverta et al., 1988, *Amer. J. Med*., 85, 289). Obesity is associated with an increase incidence of infection, diabetes and cardiovascular disease. Abnormalities in TNFα expression have been noted for each of the above conditions (Loffreda, et al., 1998, *FASEB J*. 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol*. 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J*., 15, 281). Circulating TNFα may also contribute to weight loss associated with this disease (N. Takabatake et al., 2000, *Amer. J. Resp. & Crit. Care Med*., 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol*., 278, L3-12), kidney (Lemay et al., 2000, *Transplantation*, 69, 959), and the nervous system (Mitsui et al., 1999, *Brain Res*., 844, 192).

TNFα is also a potent osteoclastogenic agent and is involved in bone resorption and diseases involving bone resorption (Abu-Amer et al., 2000, *J. Biol. Chem*., 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther*., 14, 31). Cytokines including IL-1, TNF and GM-CSF have been shown to stimulate proliferation of acute myelogenous leukemia blasts (Bruserud, 1996, *Leukemia Res*. 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat*. 7, 177). Data obtained from IL-1 knock out mice indicates the critical involvement in fever for this cytokine (Kluger et al., 1998, *Clin Exp Pharmacol Physiol*. 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr*. 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol*. 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol*. 21: 487). Marked cytokine differences, such as IL-6 levels, exist in vivo between osteoclasts of normal bone and bone from patients with Paget's disease (Mills, et al., 1997, *Calcif Tissue Int*.

61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther*. 1, 107). Several infectious diseases, such as influenza, indicate IL-6 and IFN alpha as key factors in both symptom formation and in host defense (Hayden, et al., 1998, *J Clin Invest*. 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci*. 6, 929). Compounds that interfered with the production of cytokines including IL-6, and TNF were effective in blocking a passive cutaneous anaphylaxis in mice (Scholz et al., 1998, *J. Med. Chem*., 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol*. 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma*. 19, 173). The development of insulin-dependent diabetes (Type 1) can be correlated with the accumulation in pancreatic islet cells of T-cells producing IFN γ (Ablumunits, et al., 1998, *J Autoimmun*. 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol*. 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol*. 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol*. 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg*. 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med*. 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol*. 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res*. 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilboum, et al., 1997, *Dis Mon*. 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther*. 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Ret syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anat-agonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95–101; Shock 1998 Sep. 10(3): 160–75. p38MAP kinase pathway plays an role in B. burgdorferi-elicited infammation and may be useful in treating inflammation induced by the Lyme disease agent. Anguita, J. et. al., *The Journal of Immunology*, 2002, 168:6352–6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

Compounds active against p38 MAP kinase can also be useful for treating various types of cancers as described in WO 03/068223.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

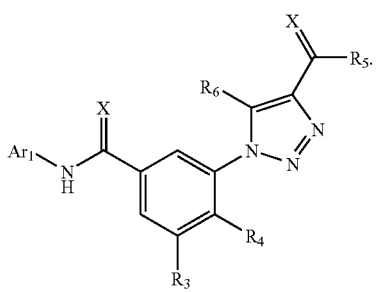

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE INVENTION

In the broadest generic embodiment, there is provided compounds of the formula (I)

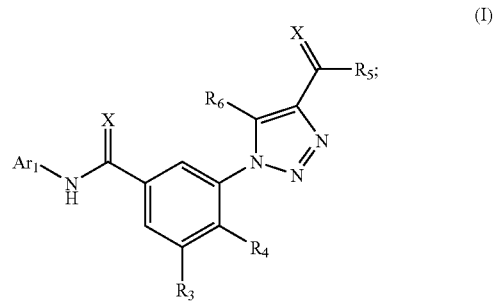

wherein:

$Ar_1$ is carbocycle optionally substituted with one $R_1$, and wherein $Ar_1$ is independently substituted with two $R_2$ groups;

$R_1$ is hydrogen, $NO_2$, —$N(R^c)_2$, J-C(O)—$N(R^c)$— or J-S(O)$_m$—$N(R^c)$— m is 0, 1 or 2 and wherein $R^c$ is chosen from hydrogen or C1–5 alkyl;

J is chosen from C1–10 alkyl and carbocycle each optionally substituted by $R^b$;

$R_2$ is chosen from C1–6 alkyl or C3–7 cycloalkyl which may optionally be partially or fully halogenated, C1–4 acyl, aroyl, C1–4 alkoxy, which may optionally be partially or fully halogenated, halogen, C1–6 alkoxycarbonyl, carbocyclesulfonyl and —$SO_2$—$CF_3$;

$R_3$, $R_4$, $R_6$, $R_7$ and $R_8$ are each independently chosen from hydrogen, halogen, C1–5 alkyl, C1–5 alkoxy, C1–5 alkyl C1–5 alkoxy, hydroxy, hydroxy C1–5 alkyl or amino optionally mono- or di-substituted by C1–5 alkyl, aryl or aryl C1–5 alkyl;

$R_5$ is: a bond, —O—, —S—, —N<, —NH—, C(O), a linear chain chosen from —NH(CR$_7$R$_8$)$_n$—, —(CR$_7$R$_8$)$_n$—, —O(CR$_7$R$_8$)$_n$—, —C(O)—O(CR$_7$R$_8$)$_n$—, —S(CR$_7$R$_8$)$_n$—, C(O)(CR$_7$R$_8$)$_n$— and —C(O)NH(CR$_7$R$_8$)$_n$—, wherein n is 1–5 and each of the aforementioned $R_5$ is further substituted by $R^a$, or $R_5$ is a ring system chosen from aryl, heteroaryl or heterocyclyl each optionally substituted by $R^a$;

$R^a$ and $R^b$ are each independently chosen from hydrogen, C1–5 alkyl, hydroxyC1–5 alkyl, C2–5 alkenyl, C2–5 alkynyl, carbocycle, heterocycle, heteroaryl, C1–5 alkoxy, C1–5 alkylthio, amino, C1–5 alkylamino, C1–5 dialkylamino, C1–5 acyl, C1–5 alkoxycarbonyl, C1–5 acyloxy, C1–5 acylamino, each of the aforementioned are optionally partially or fully halogenated, or $R^a$ and $R^b$ are chosen from C1–5 alkylsulphonylamino, hydroxy, oxo, halogen, nitro and nitrile, and each X is independently O or S or the pharmaceutically acceptable salts, acids, esters or isomers thereof.

In another embodiment, there are provided compounds of the formula (I) as described above and wherein J is chosen from C1–10 alkyl, aryl or C3–7 cycloalkyl each optionally substituted by $R^b$;

$R_2$ is independently chosen from C1–6 alkyl which may optionally be partially or fully halogenated, acetyl, aroyl, C1–4 alkoxy, which may optionally be partially or fully halogenated, halogen, methoxycarbonyl, phenylsulfonyl and —SO$_2$—CF$_3$;

n is 1–4;

R$^a$ and R$^b$ are each independently chosen from hydrogen, C1–5 alkyl, C2–5 alkenyl, C2–5 alkynyl, C3–8 cycloalkylC0–2 alkyl, aryl, C1–5 alkoxy, C1–5 alkylthio, amino, C1–5 alkylamino, C1–5 dialkylamino, C1–5 acyl, C1–5 alkoxycarbonyl, C1–5 acyloxy, C1–5 acylamino, C1–5 sulphonylamino, hydroxy, halogen, trifluoromethyl, nitro, nitrile or R$^a$ and R$^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl;

R$_7$ is hydrogen;

and each X is O.

In yet another embodiment, there are provided compounds of the formula (I) as described immediately above and wherein R$_5$ is: —O—, —S—, —NH—, C(O), a linear chain chosen from —NH(CR$_7$R$_8$)$_n$—, —(CR$_7$R$_8$)$_n$—, —O(CR$_7$R$_8$)$_n$—, —C(O)—O(CR$_7$R$_8$)$_n$—, —S(CR$_7$R$_8$)$_n$—, —C(O)NH(CR$_7$R$_8$)$_n$—, wherein n is 1–3 and each of the aforementioned R$_5$ is further substituted by R$^a$.

In yet another embodiment, there are provided compounds of the formula (I) as described immediately above and wherein Ar$^1$ is chosen from cyclopropyl, cyclobutyl, cyclopentyl, cyclohexyl and cycloheptyl, phenyl, naphthyl, tetrahydronaphthyl, indanyl and indenyl, each Ar$^1$ is substituted with one R$^1$, and independently substituted with two R$^2$ groups;

R$^1$ is NO$_2$, NH$_2$, C1–3acylNH— or the formula:

J-S(O)$_m$—N(R$^c$)—;

J is C1–10 alkyl;

R$_2$ is independently chosen from C1–6 alkyl which may optionally be partially or fully halogenated and C1–3 alkoxy, which may optionally be partially or fully halogenated;

R$_3$ and R$_4$ are each independently chosen from hydrogen, C1–3 alkyl and chloro;

R$_6$ is chosen from hydrogen and amino;

R$_5$ is: —NH—, C(O), a linear chain chosen from —NH(CR$_7$R$_8$)$_n$—, —(CR$_7$R$_8$)$_n$—, —O(CR$_7$R$_8$)$_n$—, —C(O)—O(CR$_7$R$_8$)$_n$—, C(O)(CR$_7$R$_8$)$_n$— and —C(O)NH(CR$_7$R$_8$)$_n$— wherein n is 1–2 and each of the aforementioned R$_5$ is further substituted by R$^a$, R$^a$ and R$^b$ are each independently chosen from hydrogen, C1–5 alkyl, C3–7 cycloalkylC0–2 alkyl, aryl, C1–5 alkoxy, amino, C1–5 alkylamino, C1–3 dialkylamino, C1–3 acyl, C1–5 alkoxycarbonyl, C1–3 acyloxy, C1–3 acylamino, C1–3 sulphonylamino, hydroxy, halogen, trifluoromethyl, nitro, nitrile;

or R$^a$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl.

In yet still another embodiment, there are provided compounds of the formula (I) as described immediately above and wherein Ar$^1$ is

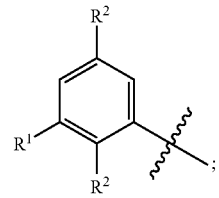

R$^1$ is the formula:

J-S(O)$_2$—NH—;

J is C1–5 alkyl;

R$_2$ is independently chosen from C1–5 alkyl which may optionally be partially or fully halogenated and C1–2 alkoxy, which may optionally be partially or fully halogenated;

R$_3$ is hydrogen;

R$_4$ is chosen from hydrogen and methyl;

R$_8$ is hydrogen, methyl, ethyl, CH$_2$OH and CH$_2$OCH$_3$.

In yet another embodiment, there are provided compounds of the formula (I) as described immediately above and wherein R$_3$ is hydrogen;

R$_4$ is methyl;

R$^a$ is chosen from hydrogen, C1–5 alkyl, C3–6 cycloalkylC0–2 alkyl, phenyl, C1–5 alkoxy, amino, C1–5 alkylamino, C1–3 dialkylamino, C1–3 acyl, C1–5 alkoxycarbonyl, C1–3 acyloxy, C1–3 acylamino, hydroxy, halogen;

or R$^a$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl.

In yet another embodiment, there are provided compounds of the formula (I) as described immediately above and wherein R$^a$ is chosen from hydrogen, C1–5 alkyl, C3–6 cycloalkyl, phenyl, C1–5 alkoxy, C1–5 alkoxycarbonyl, C1–3 acyloxy, C1–3 acylamino, hydroxy, halogen;

or R$^a$ is chosen morpholinyl, piperidinyl and pyridinyl.

In yet another embodiment, there are provided compounds of the formula (I) as described immediately above and wherein Ar$^1$ is

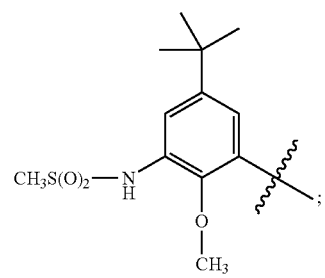

R$_5$ is —NH(CR$_7$R$_8$)$_n$—R$^a$, wherein R$^a$ is chosen from phenyl, morpholinyl, piperidinyl, pyridinyl, cyclopropyl, cyclohexyl, C1–5 alkyl and C1–3 alkoxy.

The following are representative compounds of the invention which can be made according to the general schemes and working examples below:

TABLE I

| Structure | Name |
|---|---|
| (structure) | 1-[5-(3-Methanesulfonylamino-2-methoxy-5-trifluoromethyl-phenylcarbamoyl)-2-methyl-phenyl]-1H-1,2,3-triazole-4-carboxylic acid methyl ester |
| (structure) | 1-[5-(5-tert-Butyl-2-methoxy-phenylcarbamoyl)-2-methyl-phenyl]-1H-1,2,3-triazole-4-carboxylic acid ((R)-1-phenyl-ethyl)-amide |
| (structure) | 1-[5-(5-tert-Butyl-2-methoxy-phenylcarbamoyl)-2-methyl-phenyl]-1H-1,2,3-triazole-4-carboxylic acid (2-morpholin-4-yl-ethyl)-amide |
| (structure) | 1-[5-(5-tert-Butyl-2-methoxy-phenylcarbamoyl)-2-methyl-phenyl]-1H-1,2,3-triazole-4-carboxylic acid benzylamide |
| (structure) | 1-[5-(5-tert-Butyl-2-methoxy-phenylcarbamoyl)-2-methyl-phenyl]-1H-1,2,3-triazole-4-carboxylic acid methyl ester |

TABLE I-continued

| | |
|---|---|
| 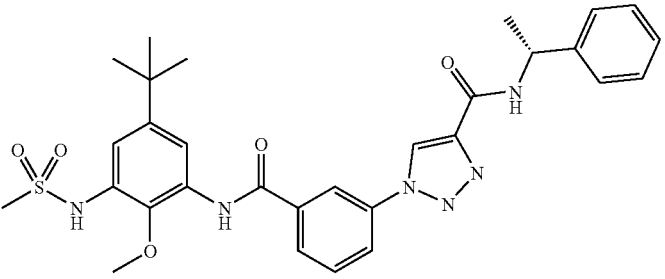 | 1-[3-(5-tert-Butyl-3-methanesulfonylamino-2-methoxy-phenylcarbamoyl)-phenyl]-1H-[1,2,3]triazole-4-carboxylic acid ((R)-1-phenyl-ethyl)-amide |
| 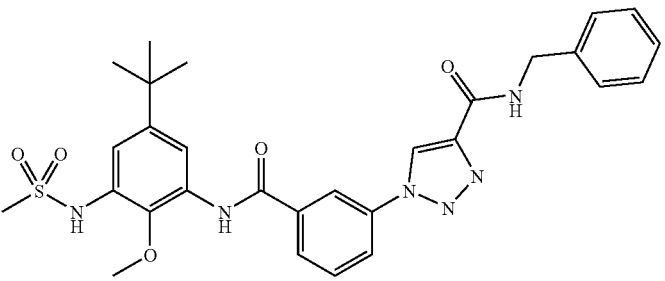 | 1-[3-(5-tert-Butyl-3-methanesulfonylamino-2-methoxy-phenylcarbamoyl)-phenyl]-1H-[1,2,3]triazole-4-carboxylic acid benzylamide |
| 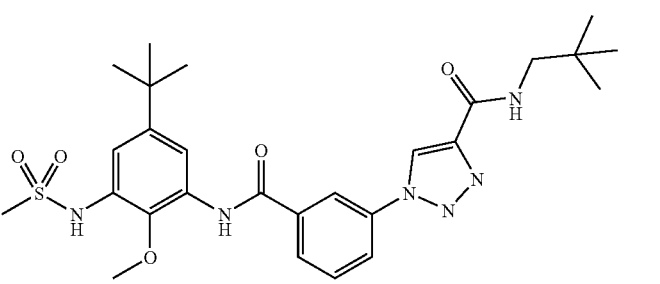 | 1-[3-(5-tert-Butyl-3-methanesulfonylamino-2-methoxy-phenylcarbamoyl)-phenyl]-1H-[1,2,3]triazole-4-carboxylic acid (2,2-dimethyl-propyl)-amide |
| 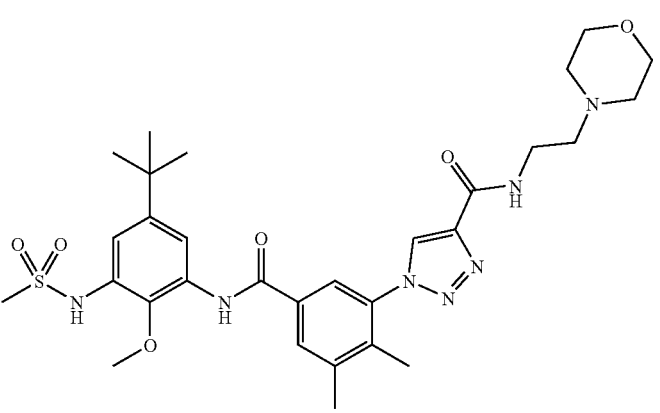 | 1-[5-(5-tert-Butyl-3-methanesulfonylamino-2-methoxy-phenylcarbamoyl)-2,3-dimethyl-phenyl]-1H-1,2,3-triazole-4-carboxylic acid (2-morpholin-4-yl-ethyl)-amide |
| 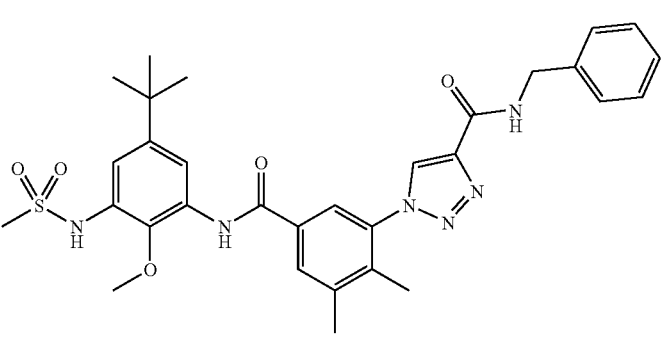 | 1-[5-(5-tert-Butyl-3-methanesulfonylamino-2-methoxy-phenylcarbamoyl)-2,3-dimethyl-phenyl]-1H-1,2,3-triazole-4-carboxylic acid benzylamide |

TABLE I-continued

| Structure | Name |
|---|---|
| 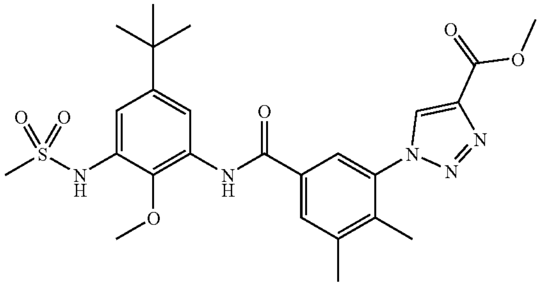 | 1-[5-(5-tert-Butyl-3-methanesulfonylamino-2-methoxy-phenylcarbamoyl)-2,3-dimethyl-phenyl]-1H-1,2,3-triazole-4-carboxylic acid methyl ester |
| 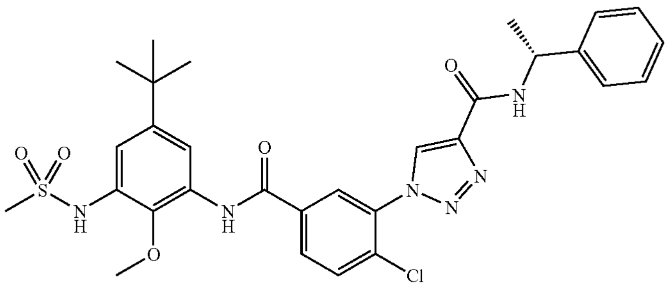 | 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-ethyl)-amide |
| 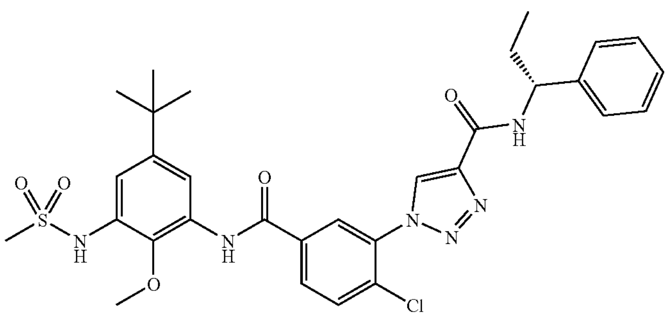 | 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-propyl)-amide |
| 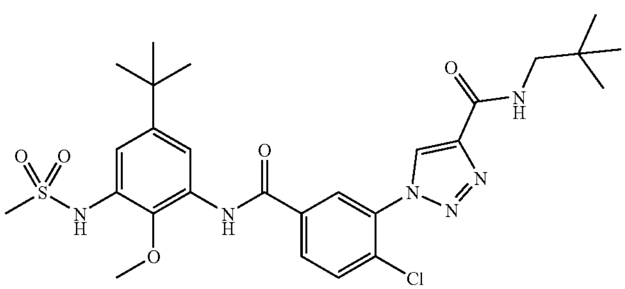 | 1-[5-(5-tert-Butyl-3-methanesulfonylamino-2-methoxy-phenylcarbamoyl)-2-chloro-phenyl]-1H-1,2,3-triazole-4-carboxylic acid (2,2-dimethyl-propyl)-amide |
| 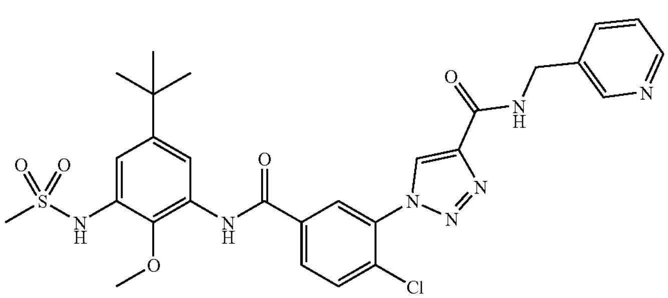 | 1-[5-(5-tert-Butyl-3-methanesulfonylamino-2-methoxy-phenylcarbamoyl)-2-chloro-phenyl]-1H-1,2,3-triazole-4-carboxylic acid (pyridin-3-ylmethyl)-amide |

TABLE I-continued

| Structure | Name |
|---|---|
| (structure) | 1-[5-(5-tert-Butyl-3-methanesulfonylamino-2-methoxy-phenylcarbamoyl)-2-chloro-phenyl]-1H-1,2,3-triazole-4-carboxylic acid ethyl ester |
| (structure) | 1-[5-(5-tert-Butyl-3-methanesulfonylamino-2-methoxy-phenylcarbamoyl)-2-chloro-phenyl]-1H-1,2,3-triazole-4-carboxylic acid methyl ester |
| (structure) | 1-[5-(5-tert-Butyl-3-methanesulfonylamino-2-methoxy-phenylcarbamoyl)-2-fluoro-phenyl]-1H-[1,2,3]triazole-4-carboxylic acid benzylamide |
| (structure) | 1-[5-(5-tert-Butyl-3-methanesulfonylamino-2-methoxy-phenylcarbamoyl)-2-fluoro-phenyl]-1H-[1,2,3]triazole-4-carboxylic acid (2,2-dimethyl-propyl)-amide |
| (structure) | 1-[5-(5-tert-Butyl-3-methanesulfonylamino-2-methoxy-phenylcarbamoyl)-3-fluoro-2-methyl-phenyl]-1H-[1,2,3]triazole-4-carboxylic acid (2,2-dimethyl-propyl)-amide |

TABLE I-continued

| Structure | Name |
|---|---|
| (structure) | 1-[5-(5-tert-Butyl-3-methanesulfonylamino-2-methoxy-phenylcarbamoyl)-2-methyl-phenyl]-1H-1,2,3-triazole-4-carboxylic acid |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid ((R)-1,2,2-trimethyl-propyl)-amide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid (1-pyridin-3-yl-ethyl)-amide |
| (structure) | 1-{5-[3-Methanesulfonylamino-2-methoxy-5-(2,2,2-trifluoro-1-trifluoromethyl-ethyl)-phenylcarbamoyl]-2-methyl-phenyl}-1H-[1,2,3]triazole-4-carboxylic acid ((R)-1-phenyl-ethyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid ((R)-1-cyclohexyl-ethyl)-amide |

TABLE I-continued

| Structure | Name |
|---|---|
| 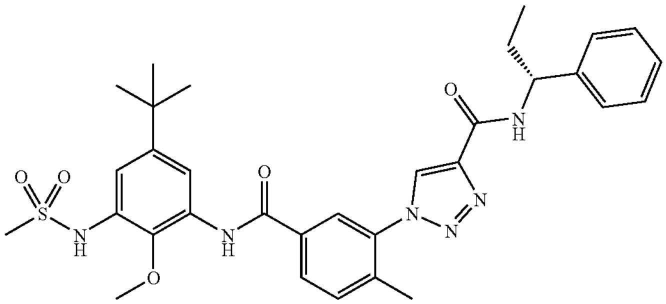 | 1-[5-(5-tert-Butyl-3-methanesulfonylamino-2-methoxy-phenylcarbamoyl)-2-methyl-phenyl]-1H-1,2,3-triazole-4-carboxylic acid ((R)-1-phenyl-propyl)-amide |
| 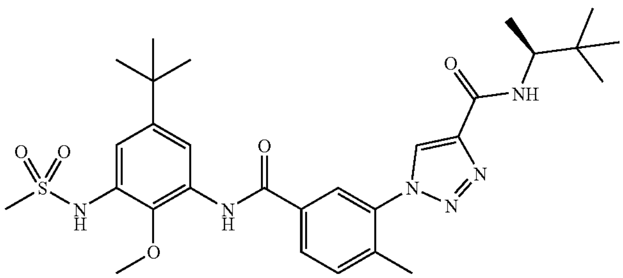 | 1-[5-(5-tert-Butyl-3-methanesulfonylamino-2-methoxy-phenylcarbamoyl)-2-methyl-phenyl]-1H-1,2,3-triazole-4-carboxylic acid ((S)-1,2,2-trimethyl-propyl)-amide |
| 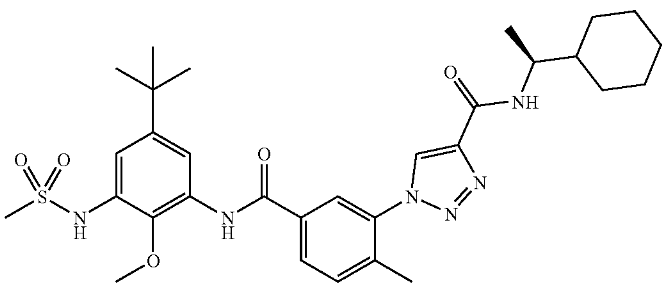 | 1-[5-(5-tert-Butyl-3-methanesulfonylamino-2-methoxy-phenylcarbamoyl)-2-methyl-phenyl]-1H-1,2,3-triazole-4-carboxylic acid ((S)-1-cyclohexyl-ethyl)-amide |
| 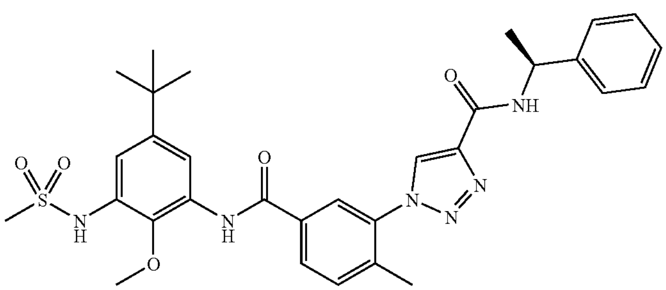 | 1-[5-(5-tert-Butyl-3-methanesulfonylamino-2-methoxy-phenylcarbamoyl)-2-methyl-phenyl]-1H-1,2,3-triazole-4-carboxylic acid ((S)-1-phenyl-ethyl)-amide |
| 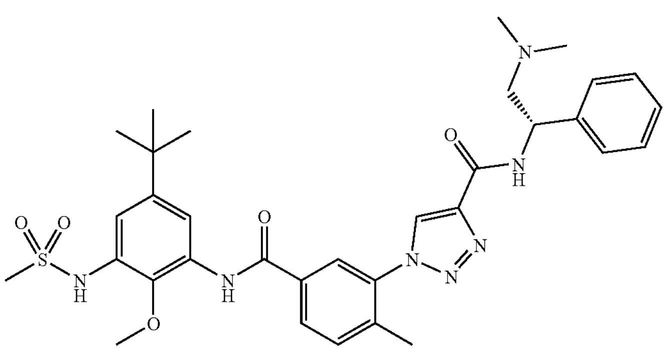 | 1-[5-(5-tert-Butyl-3-methanesulfonylamino-2-methoxy-phenylcarbamoyl)-2-methyl-phenyl]-1H-1,2,3-triazole-4-carboxylic acid ((S)-2-dimethylamino-1-phenyl-ethyl)-amide |

TABLE I-continued

| Structure | Name |
|---|---|
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid ((R)-3-dimethylamino-1-phenyl-propyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid ((S)-2-methoxy-1-phenyl-ethyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid (1-methyl-1-phenyl-ethyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid (2,2-dimethyl-propyl)-amide |
| (structure) | 1-[5-(3-Amino-5-tert-butyl-2-methoxy-phenylcarbamoyl)-2-methyl-phenyl]-1H-[1,2,3]triazole-4-carboxylic acid (2,2-dimethyl-propyl)-amide |

TABLE I-continued

| Structure | Name |
|---|---|
| 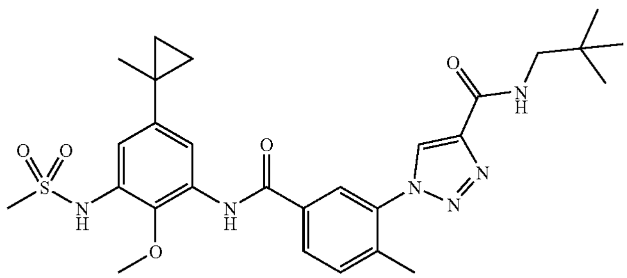 | 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid (2,2-dimethyl-propyl)-amide |
| 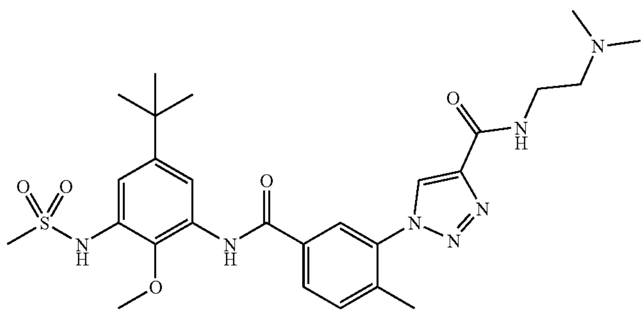 | 1-[5-(5-tert-Butyl-3-methanesulfonylamino-2-methoxy-phenylcarbamoyl)-2-methyl-phenyl]-1H-1,2,3-triazole-4-carboxylic acid (2-dimethylamino-ethyl)-amide |
| 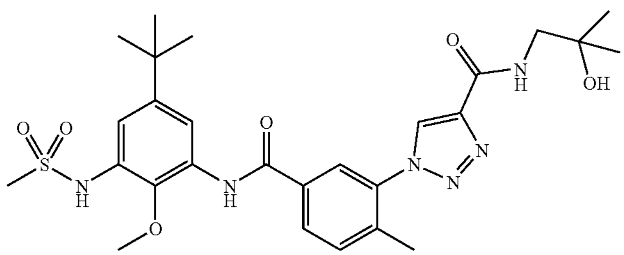 | 1-[5-(5-tert-Butyl-3-methanesulfonylamino-2-methoxy-phenylcarbamoyl)-2-methyl-phenyl]-1H-1,2,3-triazole-4-carboxylic acid (2-hydroxy-2-methyl-propyl)-amide |
| 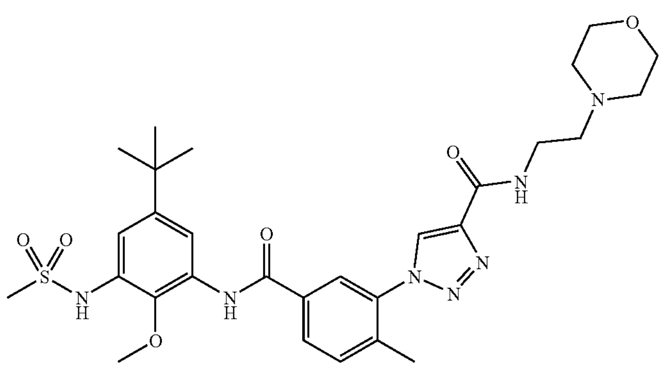 | 1-[5-(5-tert-Butyl-3-methanesulfonylamino-2-methoxy-phenylcarbamoyl)-2-methyl-phenyl]-1H-1,2,3-triazole-4-carboxylic acid (2-morpholin-4-yl-ethyl)-amide |
| 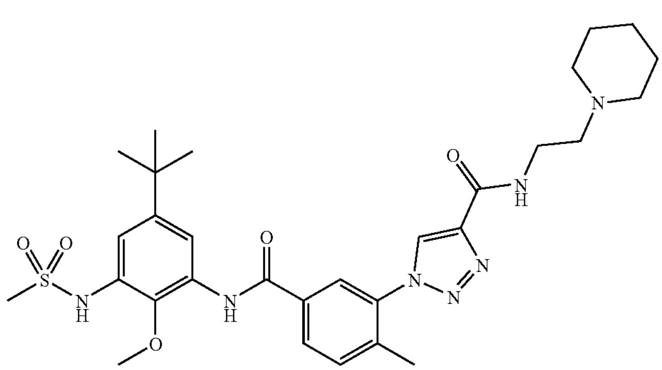 | 1-[5-(5-tert-Butyl-3-methanesulfonylamino-2-methoxy-phenylcarbamoyl)-2-methyl-phenyl]-1H-1,2,3-triazole-4-carboxylic acid (2-piperidin-1-yl-ethyl)-amide |

TABLE I-continued

1-[5-(5-tert-Butyl-3-methanesulfonylamino-2-methoxy-phenylcarbamoyl)-2-methyl-phenyl]-1H-1,2,3-triazole-4-carboxylic acid (3-dimethylamino-2,2-dimethyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid (piperidin-4-ylmethyl)-amide 1-[5-(5-tert-Butyl-3-methanesulfonylamino-2-methoxy-phenylcarbamoyl)-2-methyl-phenyl]-1H-[1,2,3]triazole-4-carboxylic acid (1-methyl-piperidin-4-ylmethyl)-amide 1-[5-(5-tert-Butyl-3-methanesulfonylamino-2-methoxy-phenylcarbamoyl)-2-methyl-phenyl]-1H-[1,2,3]triazole-4-carboxylic acid ((S)-1-ethyl-pyrrolidin-2-ylmethyl)-amide 1-[5-(5-tert-Butyl-3-methanesulfonylamino-2-methoxy-phenylcarbamoyl)-2-methyl-phenyl]-1H-[1,2,3]triazole-4-carboxylic acid ((R)-1-ethyl-pyrrolidin-2-ylmethyl)-amide TABLE I-continued

| Structure | Name |
|---|---|
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid (1-methyl-piperidin-3-ylmethyl)-amide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid (2-dimethylamino-2-methyl-propyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid (pyridin-3-ylmethyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid (pyridin-4-ylmethyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid 3-methyl-benzylamide |

TABLE I-continued

| | |
|---|---|
| (structure) | 1-[5-(5-tert-Butyl-3-methanesulfonylamino-2-methoxy-phenylcarbamoyl)-2-methyl-phenyl]-1H-1,2,3-triazole-4-carboxylic acid amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid benzylamide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid phenylamide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid p-tolylamide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid m-tolylamide |

TABLE I-continued

| Structure | Name |
|---|---|
| 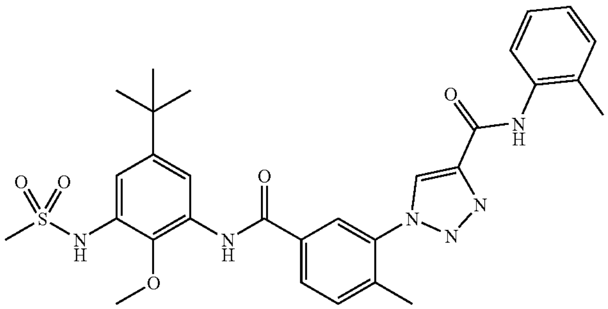 | 1-[5-(5-tert-Butyl-3-methanesulfonylamino-2-methoxy-phenylcarbamoyl)-2-methyl-phenyl]-1H-[1,2,3]triazole-4-carboxylic acid o-tolylamide |
| 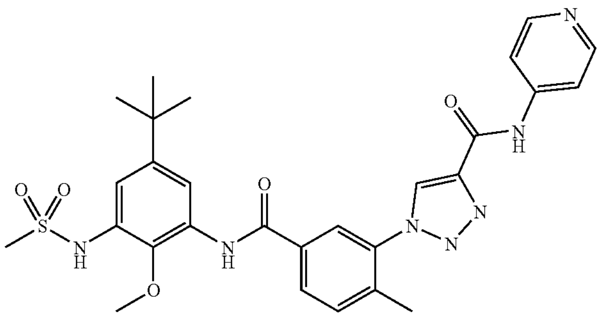 | 1-[5-(5-tert-Butyl-3-methanesulfonylamino-2-methoxy-phenylcarbamoyl)-2-methyl-phenyl]-1H-[1,2,3]triazole-4-carboxylic acid pyridin-4-ylamide |
| 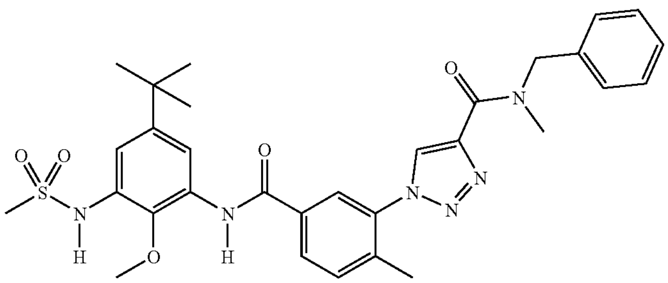 | 1-[5-(5-tert-Butyl-3-methanesulfonylamino-2-methoxy-phenylcarbamoyl)-2-methyl-phenyl]-1H-1,2,3-triazole-4-carboxylic acid benzyl methyl-amide |
| 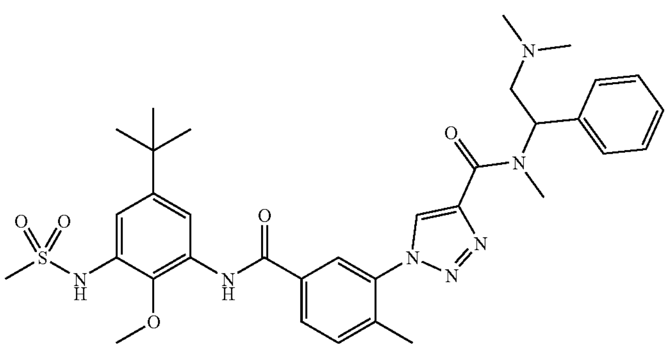 | 1-[5-(5-tert-Butyl-3-methanesulfonylamino-2-methoxy-phenylcarbamoyl)-2-methyl-phenyl]-1H-[1,2,3]triazole-4-carboxylic acid ((S)-2-dimethylamino-1-phenyl-ethyl)-methyl-amide |
| 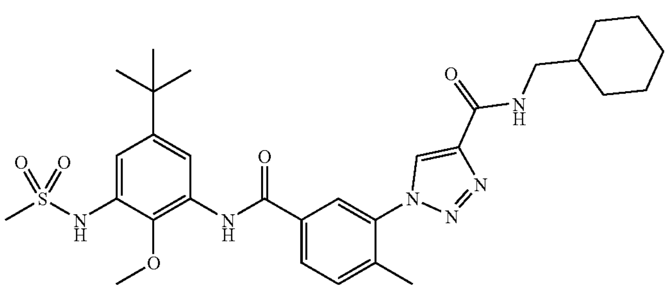 | 1-[5-(5-tert-Butyl-3-methanesulfonylamino-2-methoxy-phenylcarbamoyl)-2-methyl-phenyl]-1H-1,2,3-triazole-4-carboxylic acid cyclohexylmethyl-amide |

TABLE I-continued

| Structure | Name |
|---|---|
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopentylamide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopentylmethyl-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopropylamide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopropylmethyl-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid ethyl ester |

TABLE I-continued

| Structure | Name |
|---|---|
| 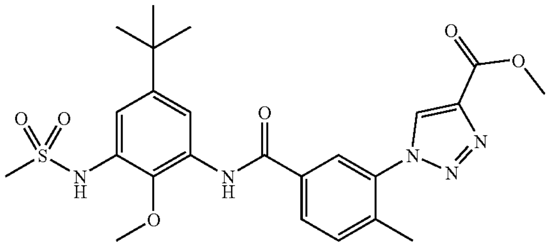 | 1-[5-(5-tert-Butyl-3-methanesulfonylamino-2-methoxy-phenylcarbamoyl)-2-methyl-phenyl]-1H-1,2,3-triazole-4-carboxylic acid methyl ester |
| 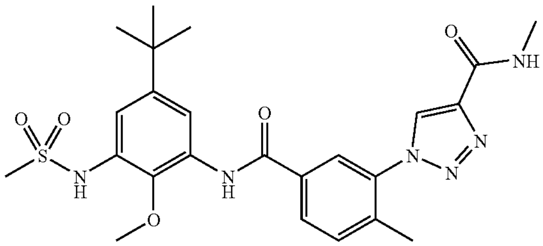 | 1-[5-(5-tert-Butyl-3-methanesulfonylamino-2-methoxy-phenylcarbamoyl)-2-methyl-phenyl]-1H-1,2,3-triazole-4-carboxylic acid methylamide |
| 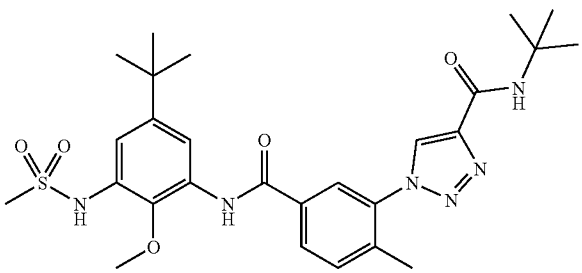 | 1-[5-(5-tert-Butyl-3-methanesulfonylamino-2-methoxy-phenylcarbamoyl)-2-methyl-phenyl]-1H-1,2,3-triazole-4-carboxylic acid tert-butylamide |
| 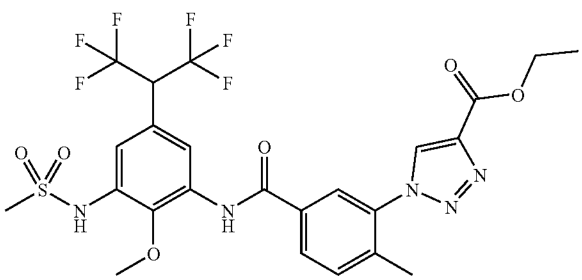 | 1-{5-[3-Methanesulfonylamino-2-methoxy-5-(2,2,2-trifluoro-1-trifluoromethyl-ethyl)-phenylcarbamoyl]-2-methyl-phenyl}-1H-1,2,3-triazole-4-carboxylic acid ethyl ester |
| 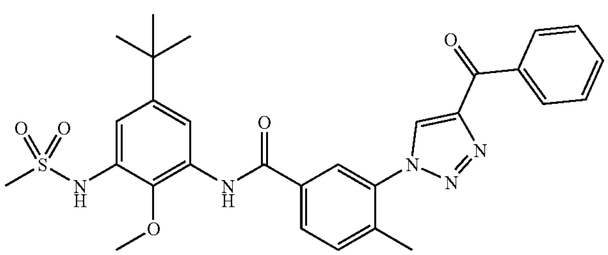 | 3-(4-Benzoyl-1,2,3-triazol-1-yl)-N-(5-tert-butyl-3-methanesulfonylamino-2-methoxy-phenyl)-4-methyl-benzamide |
| 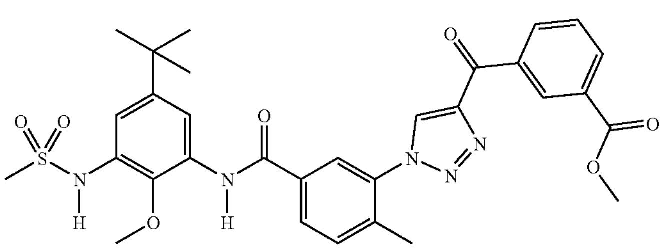 | 3-{1-[5-(5-tert-Butyl-3-methanesulfonylamino-2-methoxy-phenylcarbamoyl)-2-methyl-phenyl]-1H-1,2,3-triazole-4-carbonyl}-benzoic acid methyl ester |

TABLE I-continued

| Structure | Name |
|---|---|
| 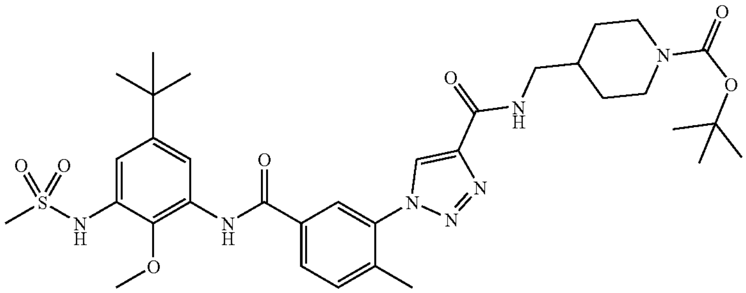 | 4-[({1-[5-(5-tert-Butyl-3-methanesulfonylamino-2-methoxy-phenylcarbamoyl)-2-methyl-phenyl]-1H-1,2,3-triazole-4-carbonyl}-amino)-methyl]-piperidine-1-carboxylic acid tert-butyl ester |
| 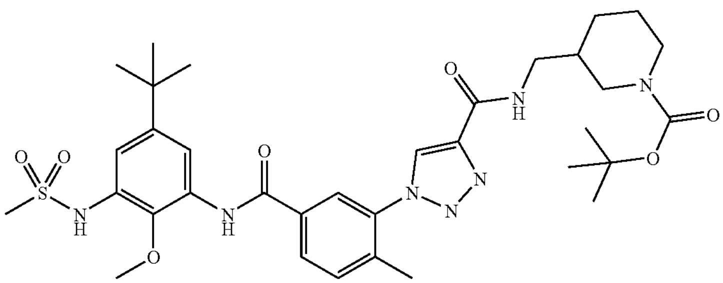 | 3-[({1-[5-(5-tert-Butyl-3-methanesulfonylamino-2-methoxy-phenylcarbamoyl)-2-methyl-phenyl]-1H-[1,2,3]triazole-4-carbonyl}-amino)-methyl]-piperidine-1-carboxylic acid tert-butyl ester |
| 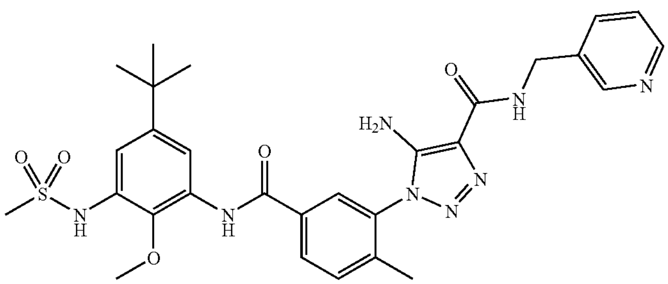 | 5-Amino-1-[5-(5-tert-butyl-3-methanesulfonylamino-2-methoxy-phenylcarbamoyl)-2-methyl-phenyl]-1H!-1,2,3-triazole-4-carboxylic acid (pyridin-3-ylmethyl)-amide |
| 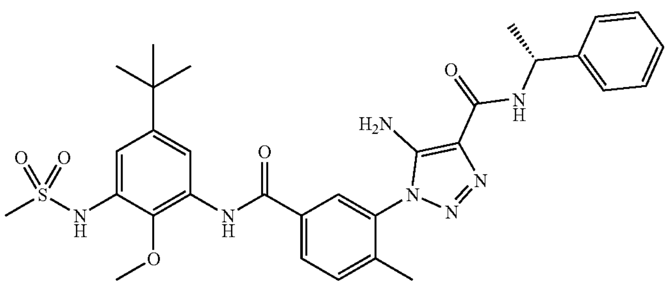 | 5-Amino-1-[5-(5-tert-butyl-3-methanesulfonylamino-2-methoxy-phenylcarbamoyl)-2-methyl-phenyl]-1H-1,2,3-triazole-4-carboxylic acid ((R)-1-phenyl-ethyl)-amide |
| 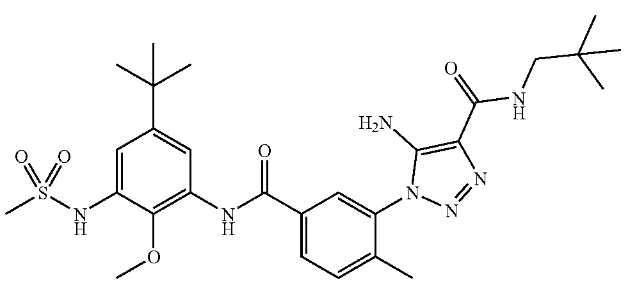 | 5-Amino-1-[5-(5-tert-butyl-3-methanesulfonylamino-2-methoxy-phenylcarbamoyl)-2-methyl-phenyl]-1H-1,2,3-triazole-4-carboxylic acid (2,2-dimethyl-propyl)-amide |

TABLE I-continued

| Structure | Name |
|---|---|
| (structure) | 5-Amino-1-[5-(5-tert-butyl-3-methanesulfonylamino-2-methoxy-phenylcarbamoyl)-2-methyl-phenyl]-1H-[1,2,3]triazole-4-carboxylic acid ((S)-1,2,2-trimethyl-propyl)-amide |
| (structure) | 5-Amino-1-[5-(5-tert-butyl-3-methanesulfonylamino-2-methoxy-phenylcarbamoyl)-2-methyl-phenyl]-1H-[1,2,3]triazole-4-carboxylic acid (3-dimethylamino-2,2-dimethyl-propyl)-amide |
| (structure) | 5-Amino-1-[5-(5-tert-butyl-3-methanesulfonylamino-2-methoxy-phenylcarbamoyl)-2-methyl-phenyl]-1H-1,2,3-triazole-4-carboxylic acid methyl ester |
| (structure) | N-(5-tert-Butyl-3-methanesulfonylamino-2-methoxy-phenyl)-3-(4-cyclohexanecarbonyl-1,2,3-triazol-1-yl)-4-methyl-benzamide |
| (structure) | N-(5-tert-Butyl-3-methanesulfonylamino-2-methoxy-phenyl)-3-[4-((S)-3-hydroxy-2-phenyl-propionyl)-1,2,3-triazol-1-yl]-4-methyl-benzamide |

TABLE I-continued

| Structure | Name |
|---|---|
| (structure) | N-(5-tert-Butyl-3-methanesulfonylamino-2-methoxy-phenyl)-3-[4-(2,6-dichloro-benzoyl)-1,2,3-triazol-1-yl]-4-methyl-benzamide |
| (structure) | N-(5-tert-Butyl-3-methanesulfonylamino-2-methoxy-phenyl)-3-[4-(2,6-dimethyl-benzoyl)-1,2,3-triazol-1-yl]-4-methyl-benzamide |
| (structure) | N-(5-tert-Butyl-3-methanesulfonylamino-2-methoxy-phenyl)-4-methyl-3-[4-((R)-2-phenyl-propionyl)-1,2,3-triazol-1-yl]-benzamide |
| (structure) | N-(5-tert-Butyl-3-methanesulfonylamino-2-methoxy-phenyl)-4-methyl-3-[4-(2-methyl-benzoyl)-1,2,3-triazol-1-yl]-benzamide |
| (structure) | N-(5-tert-Butyl-3-methanesulfonylamino-2-methoxy-phenyl)-4-methyl-3-[4-(morpholine-4-carbonyl)-1,2,3-triazol-1-yl]-benzamide | or the pharmaceutically acceptable salts, acids, esters or isomers thereof.

Preferred compounds of the invention are listed in table II.

TABLE II

| Structure | Name |
|---|---|
| 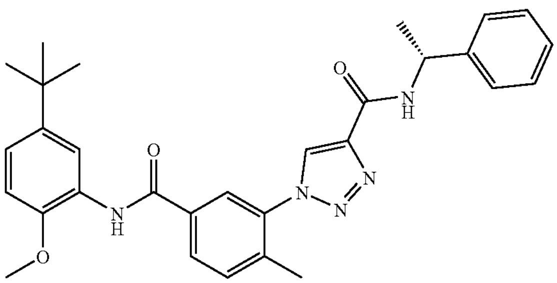 | 1-[5-(5-tert-Butyl-2-methoxy-phenylcarbamoyl)-2-methyl-phenyl]-1H-1,2,3-triazole-4-carboxylic acid ((R)-1-phenyl-ethyl)-amide |
| 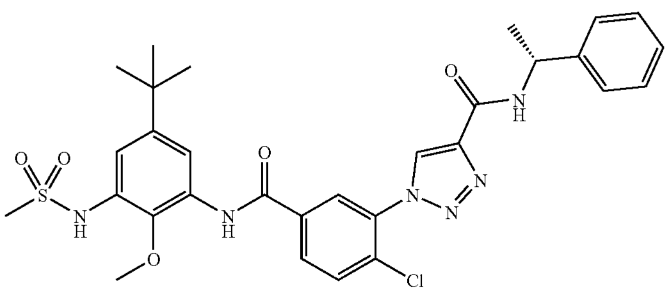 | 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-ethyl)-amide |
| 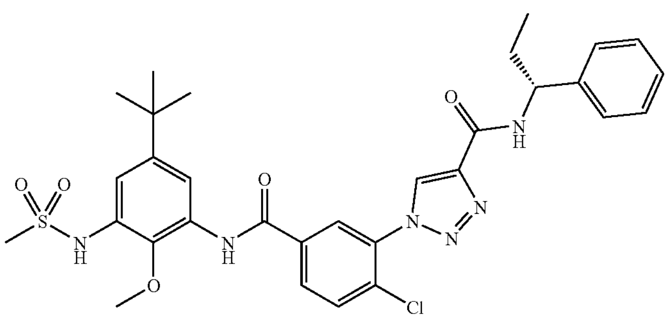 | 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-propyl)-amide |
| 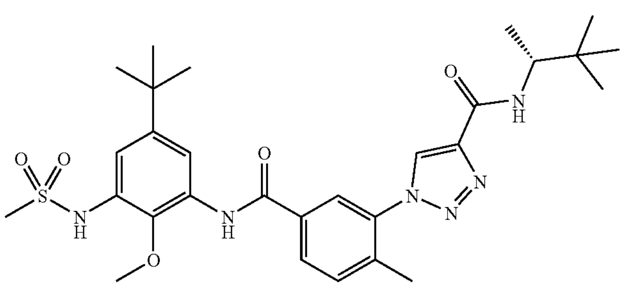 | 1-[5-(5-tert-Butyl-3-methanesulfonylamino-2-methoxy-phenylcarbamoyl)-2-methyl-phenyl]-1H-1,2,3-triazole-4-carboxylic acid ((R)-1,2,2-trimethyl-propyl)-amide |
| 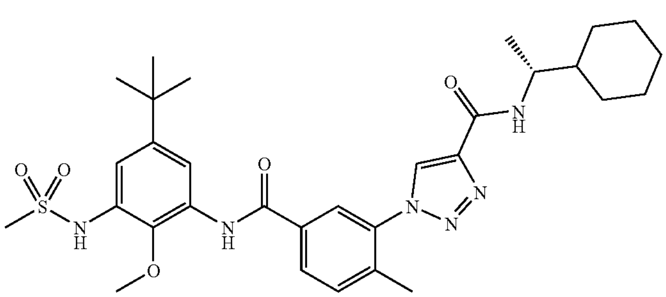 | 1-[5-(5-tert-Butyl-3-methanesulfonylamino-2-methoxy-phenylcarbamoyl)-2-methyl-phenyl]-1H-1,2,3-triazole-4-carboxylic acid ((R)-1-cyclohexyl-ethyl)-amide |

TABLE II-continued

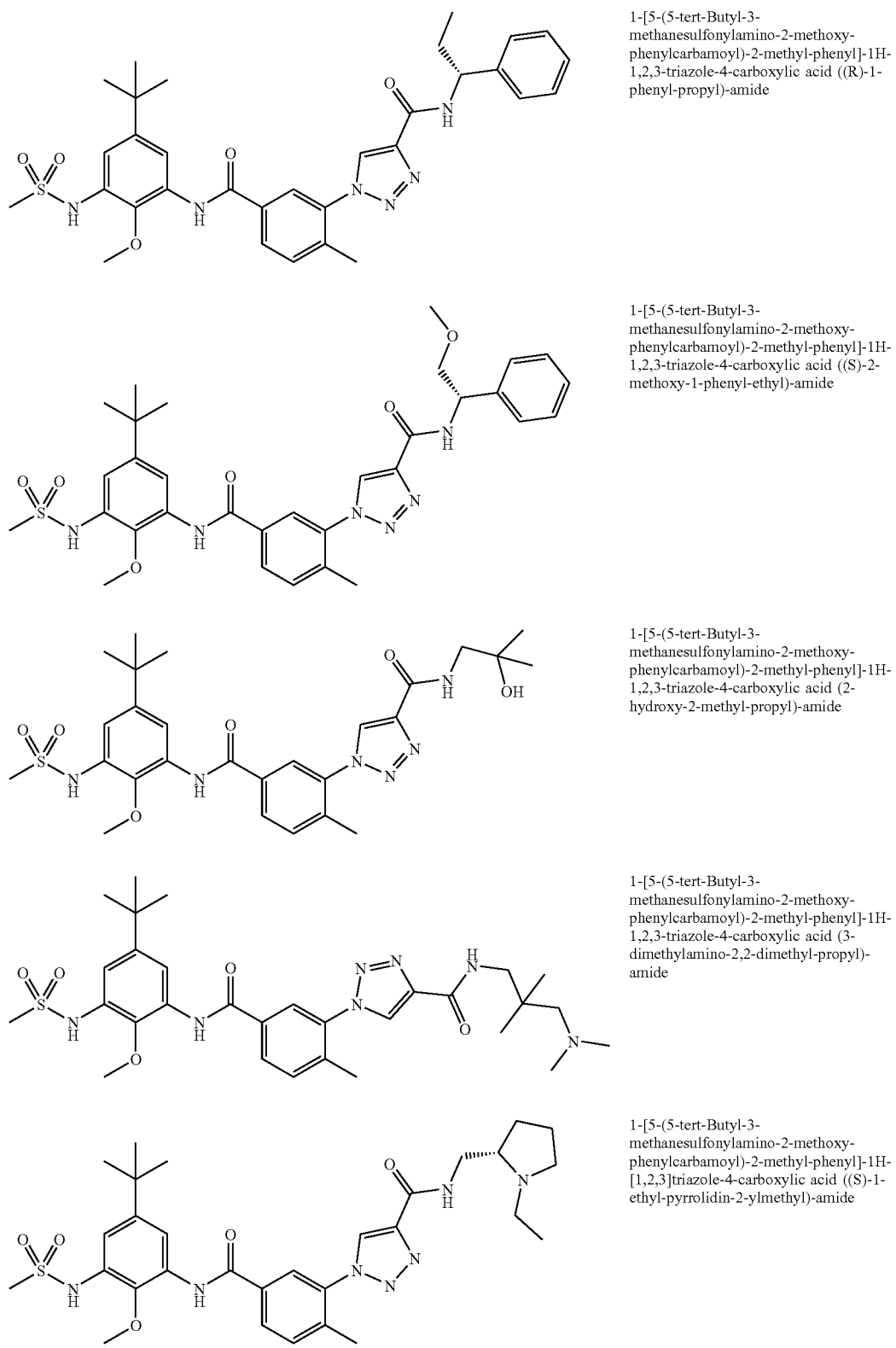

1-[5-(5-tert-Butyl-3-methanesulfonylamino-2-methoxy-phenylcarbamoyl)-2-methyl-phenyl]-1H-1,2,3-triazole-4-carboxylic acid ((R)-1-phenyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((S)-2-methoxy-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid (2-hydroxy-2-methyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid (3-dimethylamino-2,2-dimethyl-propyl)-amide 1-[5-(5-tert-Butyl-3-methanesulfonylamino-2-methoxy-phenylcarbamoyl)-2-methyl-phenyl]-1H-[1,2,3]triazole-4-carboxylic acid ((S)-1-ethyl-pyrrolidin-2-ylmethyl)-amide TABLE II-continued

| Structure | Name |
|---|---|
| 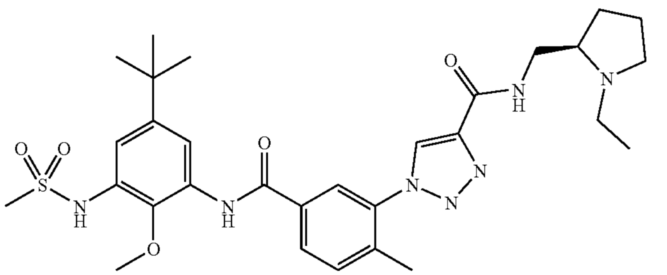 | 1-[5-(5-tert-Butyl-3-methanesulfonylamino-2-methoxy-phenylcarbamoyl)-2-methyl-phenyl]-1H-[1,2,3]triazole-4-carboxylic acid ((R)-1-ethyl-pyrrolidin-2-ylmethyl)-amide |
| 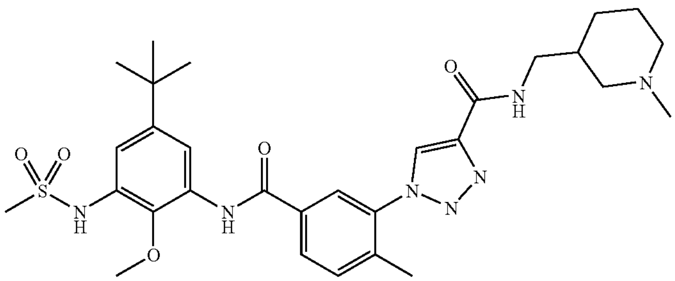 | 1-[5-(5-tert-Butyl-3-methanesulfonylamino-2-methoxy-phenylcarbamoyl)-2-methyl-phenyl]-1H-[1,2,3]triazole-4-carboxylic acid (1-methyl-piperidin-3-ylmethyl)-amide |
| 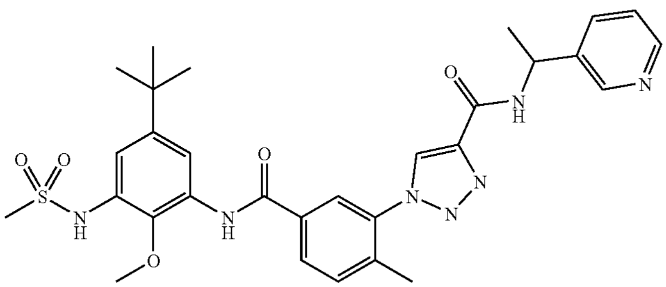 | 1-[5-(5-tert-Butyl-3-methanesulfonylamino-2-methoxy-phenylcarbamoyl)-2-methyl-phenyl]-1H-[1,2,3]triazole-4-carboxylic acid (1-pyridin-3-yl-ethyl)-amide |
| 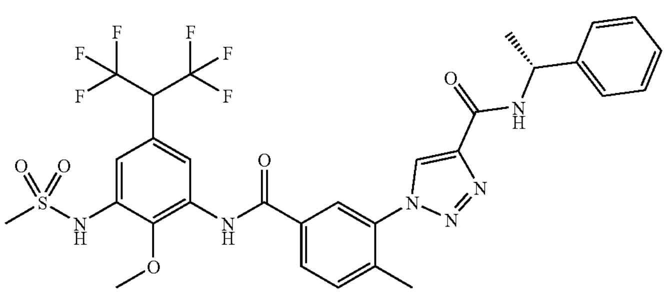 | 1-{5-[3-Methanesulfonylamino-2-methoxy-5-(2,2,2-trifluoro-1-trifluoromethyl-ethyl)-phenylcarbamoyl]-2-methyl-phenyl}-1H-[1,2,3]triazole-4-carboxylic acid ((R)-1-phenyl-ethyl)-amide |
| 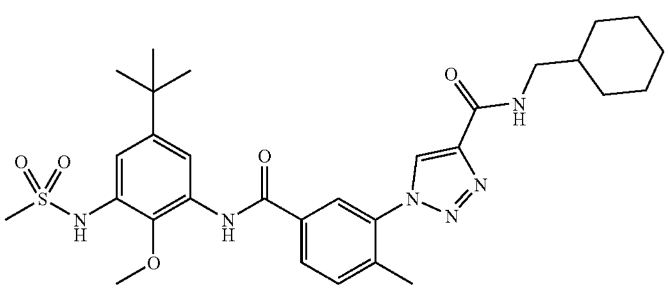 | 1-[5-(5-tert-Butyl-3-methanesulfonylamino-2-methoxy-phenylcarbamoyl)-2-methyl-phenyl]-1H-1,2,3-triazole-4-carboxylic acid cyclohexylmethyl-amide |

TABLE II-continued

| Structure | Name |
|---|---|
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopentylamide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopentylmethyl-amide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid phenylamide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid p-tolylamide |
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid m-tolylamide |

TABLE II-continued

| Structure | Name |
|---|---|
| (structure) | 1-[5-(5-tert-Butyl-3-methanesulfonylamino-2-methoxy-phenylcarbamoyl)-2-methyl-phenyl]-1H-[1,2,3]triazole-4-carboxylic acid o-tolylamide |
| (structure) | 5-Amino-1-[5-(5-tert-butyl-3-methanesulfonylamino-2-methoxy-phenylcarbamoyl)-2-methyl-phenyl]-1H!-1,2,3-triazole-4-carboxylic acid (pyridin-3-ylmethyl)-amide |
| (structure) | 5-Amino-1-[5-(5-tert-butyl-3-methanesulfonylamino-2-methoxy-phenylcarbamoyl)-2-methyl-phenyl]-1H-1,2,3-triazole-4-carboxylic acid ((R)-1-phenyl-ethyl)-amide |
| (structure) | 5-Amino-1-[5-(5-tert-butyl-3-methanesulfonylamino-2-methoxy-phenylcarbamoyl)-2-methyl-phenyl]-1H-1,2,3-triazole-4-carboxylic acid (2,2-dimethyl-propyl)-amide |
| (structure) | 5-Amino-1-[5-(5-tert-butyl-3-methanesulfonylamino-2-methoxy-phenylcarbamoyl)-2-methyl-phenyl]-1H-[1,2,3]triazole-4-carboxylic acid ((S)-1,2,2-trimethyl-propyl)-amide |

TABLE II-continued

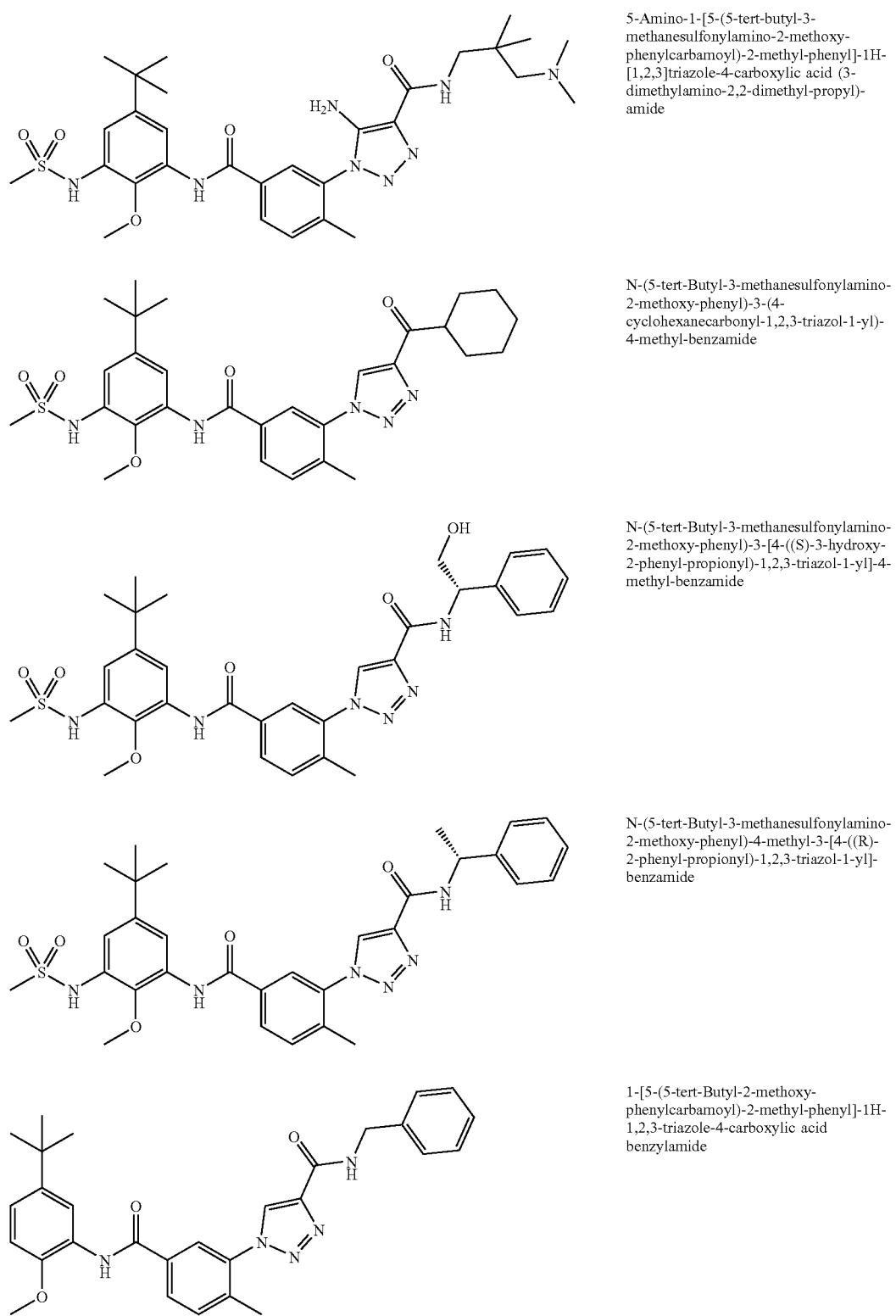

5-Amino-1-[5-(5-tert-butyl-3-methanesulfonylamino-2-methoxy-phenylcarbamoyl)-2-methyl-phenyl]-1H-[1,2,3]triazole-4-carboxylic acid (3-dimethylamino-2,2-dimethyl-propyl)-amide N-(5-tert-Butyl-3-methanesulfonylamino-2-methoxy-phenyl)-3-(4-cyclohexanecarbonyl-1,2,3-triazol-1-yl)-4-methyl-benzamide N-(5-tert-Butyl-3-methanesulfonylamino-2-methoxy-phenyl)-3-[4-((S)-3-hydroxy-2-phenyl-propionyl)-1,2,3-triazol-1-yl]-4-methyl-benzamide N-(5-tert-Butyl-3-methanesulfonylamino-2-methoxy-phenyl)-4-methyl-3-[4-((R)-2-phenyl-propionyl)-1,2,3-triazol-1-yl]-benzamide 1-[5-(5-tert-Butyl-2-methoxy-phenylcarbamoyl)-2-methyl-phenyl]-1H-1,2,3-triazole-4-carboxylic acid benzylamide TABLE II-continued

| Structure | Name |
|---|---|
| (structure) | 1-[5-(5-tert-Butyl-3-methanesulfonylamino-2-methoxy-phenylcarbamoyl)-2,3-dimethyl-phenyl]-1H-1,2,3-triazole-4-carboxylic acid benzylamide |
| (structure) | 1-[5-(5-tert-Butyl-3-methanesulfonylamino-2-methoxy-phenylcarbamoyl)-2-chloro-phenyl]-1H-1,2,3-triazole-4-carboxylic acid (2,2-dimethyl)-propyl)-amide |
| (structure) | 1-[5-(5-tert-Butyl-3-methanesulfonylamino-2-methoxy-phenylcarbamoyl)-2-chloro-phenyl]-1H-1,2,3-triazole-4-carboxylic acid (pyridin-3-ylmethyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid ((S)-1,2,2-trimethyl-propyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid ((S)-1-cyclohexyl-ethyl)-amide |

TABLE II-continued

| Structure | Name |
|---|---|
| 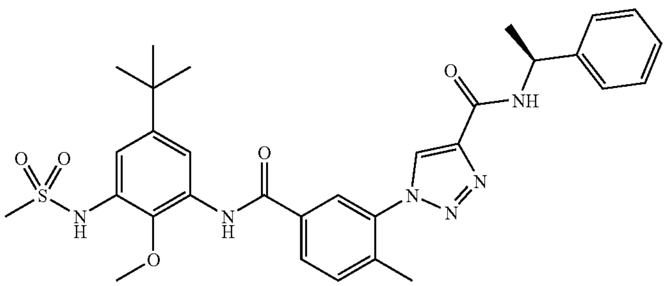 | 1-[5-(5-tert-Butyl-3-methanesulfonylamino-2-methoxy-phenylcarbamoyl)-2-methyl-phenyl]-1H-1,2,3-triazole-4-carboxylic acid ((S)-1-phenyl-ethyl)-amide |
| 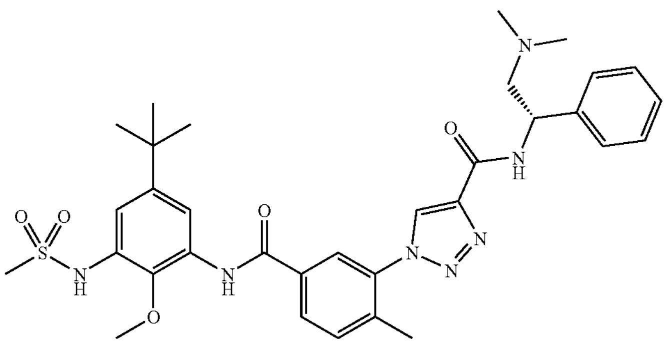 | 1-[5-(5-tert-Butyl-3-methanesulfonylamino-2-methoxy-phenylcarbamoyl)-2-methyl-phenyl]-1H-1,2,3-triazole-4-carboxylic acid ((S)-2-dimethylamino-1-phenyl-ethyl)-amide |
| 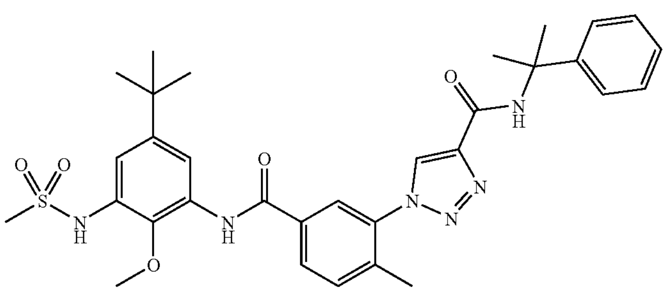 | 1-[5-(5-tert-Butyl-3-methanesulfonylamino-2-methoxy-phenylcarbamoyl)-2-methyl-phenyl]-1H-1,2,3-triazole-4-carboxylic acid (1-methyl-1-phenyl-ethyl)-amide |
| 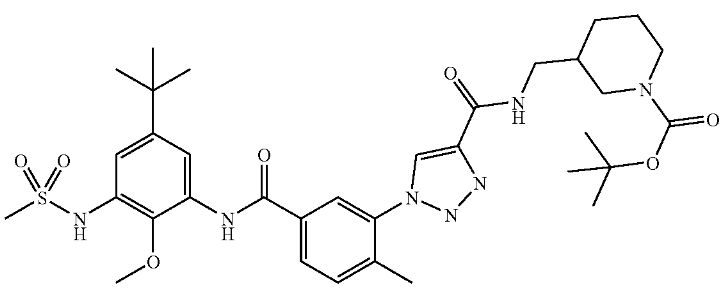 | 3-[({1-[5-(5-tert-Butyl-3-methanesulfonylamino-2-methoxy-phenylcarbamoyl)-2-methyl-phenyl]-1H-[1,2,3]triazole-4-carbonyl}-amino)-methyl]-piperidine-1-carboxylic acid tert-butyl ester |
| 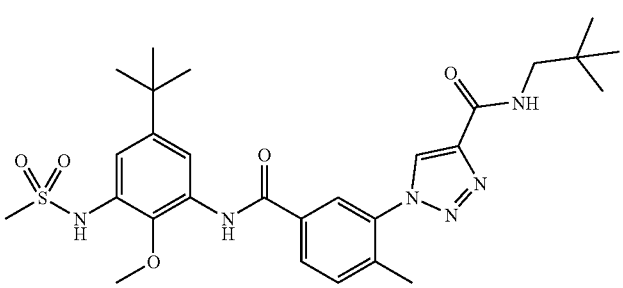 | 1-[5-(5-tert-Butyl-3-methanesulfonylamino-2-methoxy-phenylcarbamoyl)-2-methyl-phenyl]-1H-1,2,3-triazole-4-carboxylic acid (2,2-dimethyl-propyl)-amide |

TABLE II-continued

| | |
|---|---|
| 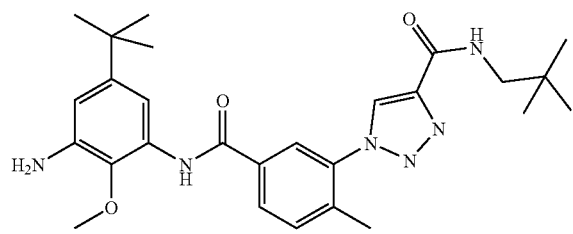 | 1-[5-(3-Amino-5-tert-butyl-2-methoxy-phenylcarbamoyl)-2-methyl-phenyl]-1H-[1,2,3]triazole-4-carboxylic acid (2,2-dimethyl-propyl)-amide |
| 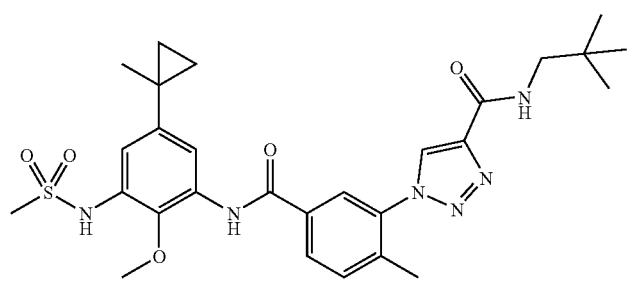 | 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid (2,2-dimethyl-propyl)-amide |
| 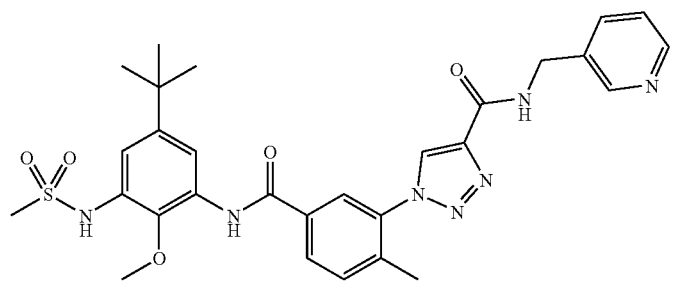 | 1-[5-(5-tert-Butyl-3-methanesulfonylamino-2-methoxy-phenylcarbamoyl)-2-methyl-phenyl]-1H-1,2,3-triazole-4-carboxylic acid (pyridin-3-ylmethyl)-amide |
| 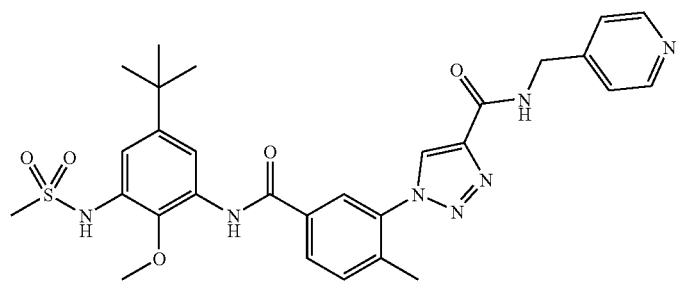 | 1-[5-(5-tert-Butyl-3-methanesulfonylamino-2-methoxy-phenylcarbamoyl)-2-methyl-phenyl]-1H-1,2,3-triazole-4-carboxylic acid (pyridin-4-ylmethyl)-amide |
| 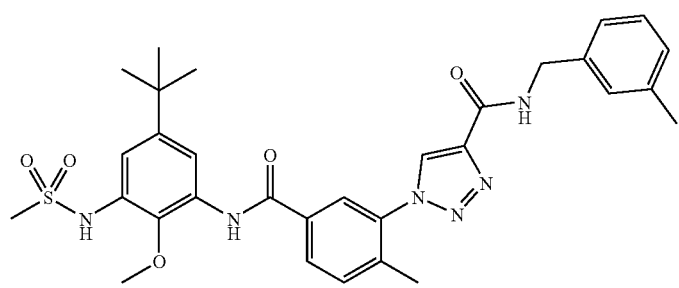 | 1-[5-(5-tert-Butyl-3-methanesulfonylamino-2-methoxy-phenylcarbamoyl)-2-methyl-phenyl]-1H-1,2,3-triazole-4-carboxylic acid 3-methyl-benzylamide |

TABLE II-continued

| Structure | Name |
|---|---|
| 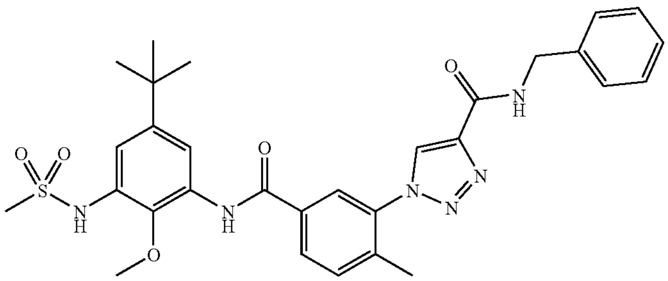 | 1-[5-(5-tert-Butyl-3-methanesulfonylamino-2-methoxy-phenylcarbamoyl)-2-methyl-phenyl]-1H-1,2,3-triazole-4-carboxylic acid benzylamide |
| 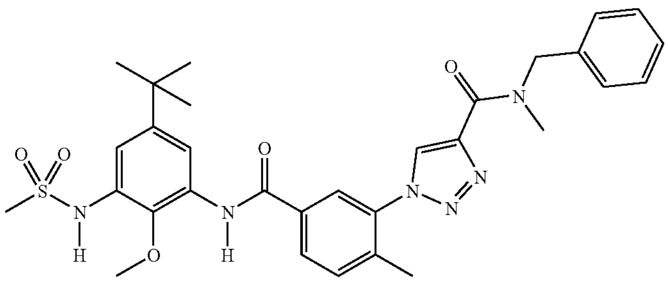 | 1-[5-(5-tert-Butyl-3-methanesulfonylamino-2-methoxy-phenylcarbamoyl)-2-methyl-phenyl]-1H-1,2,3-triazole-4-carboxylic acid benzyl-methyl-amide |
| 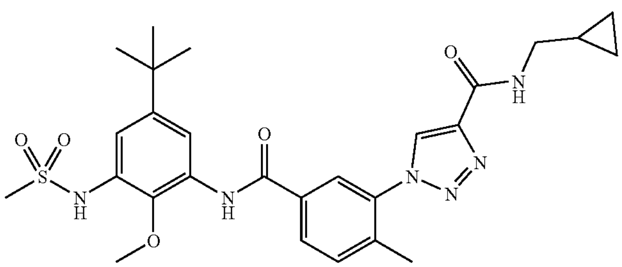 | 1-[5-(5-tert-Butyl-3-methanesulfonylamino-2-methoxy-phenylcarbamoyl)-2-methyl-phenyl]-1H-1,2,3-triazole-4-carboxylic acid cyclopropylmethyl-amide |
| 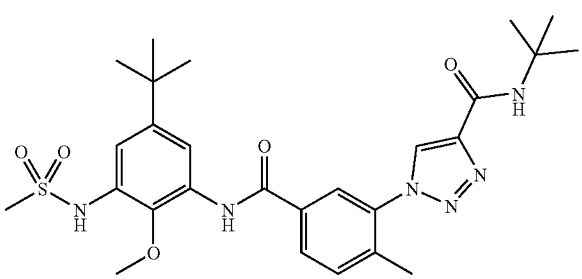 | 1-[5-(5-tert-Butyl-3-methanesulfonylamino-2-methoxy-phenylcarbamoyl)-2-methyl-phenyl]-1H-1,2,3-triazole-4-carboxylic acid tert-butylamide |
| 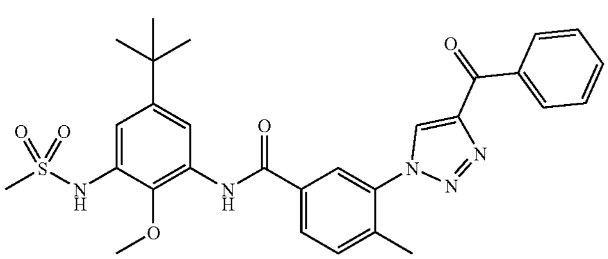 | 3-(4-Benzoyl-1,2,3-triazol-1-yl)-N-(5-tert-butyl-3-methanesulfonylamino-2-methoxy-phenyl)-4-methyl-benzamide |
| 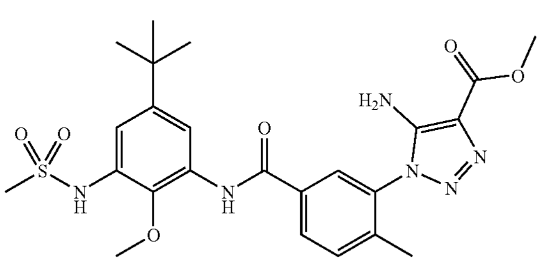 | 5-Amino-1-[5-(5-tert-butyl-3-methanesulfonylamino-2-methoxy-phenylcarbamoyl)-2-methyl-phenyl]-1H-1,2,3-triazole-4-carboxylic acid methyl ester |

TABLE II-continued

| | |
|---|---|
| 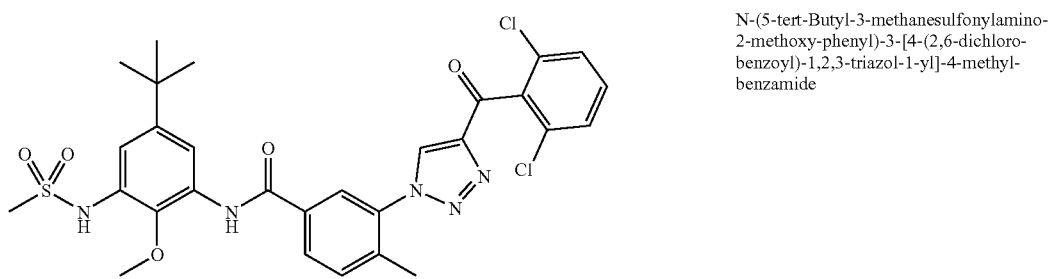 | N-(5-tert-Butyl-3-methanesulfonylamino-2-methoxy-phenyl)-3-[4-(2,6-dichloro-benzoyl)-1,2,3-triazol-1-yl]-4-methyl-benzamide |
| 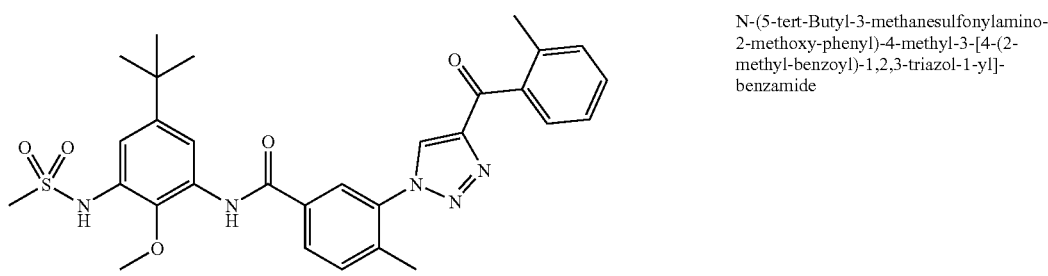 | N-(5-tert-Butyl-3-methanesulfonylamino-2-methoxy-phenyl)-4-methyl-3-[4-(2-methyl-benzoyl)-1,2,3-triazol-1-yl]-benzamide | or the pharmaceutically acceptable salts, acids, esters or isomers thereof.

Most preferred compounds of the invention are listed in table III:

TABLE III

| | |
|---|---|
| 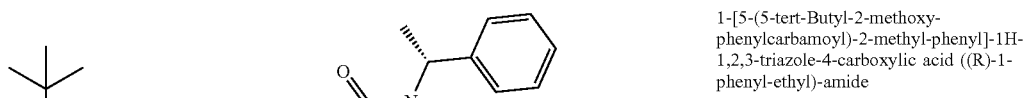 | 1-[5-(5-tert-Butyl-2-methoxy-phenylcarbamoyl)-2-methyl-phenyl]-1H-1,2,3-triazole-4-carboxylic acid ((R)-1-phenyl-ethyl)-amide |
| 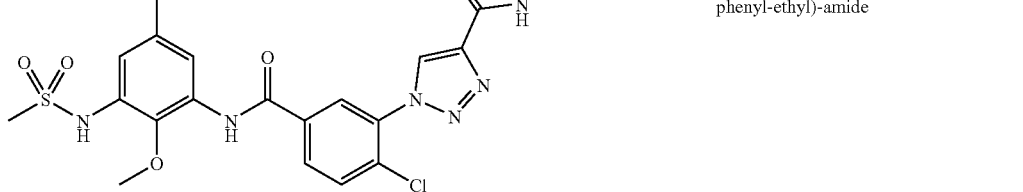 | 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-ethyl)-amide |

TABLE III-continued

| Structure | Name |
|---|---|
| | 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-propyl)-amide |
| | 1-[5-(5-tert-Butyl-3-methanesulfonylamino-2-methoxy-phenylcarbamoyl)-2-methyl-phenyl]-1H-1,2,3-triazole-4-carboxylic acid ((R)-1,2,2-trimethyl-propyl)-amide |
| | 1-[5-(3-Amino-5-tert-butyl-2-methoxy-phenylcarbamoyl)-2-methyl-phenyl]-1H-[1,2,3]triazole-4-carboxylic acid (2,2-dimethyl-propyl)-amide |
| | 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid (2,2-dimethyl-propyl)-amide |
| | 1-[5-(5-tert-Butyl-3-methanesulfonylamino-2-methoxy-phenylcarbamoyl)-2-methyl-phenyl]-1H-1,2,3-triazole-4-carboxylic acid ((R)-1-cyclohexyl-ethyl)-amide |

TABLE III-continued

| Structure | Name |
|---|---|
| 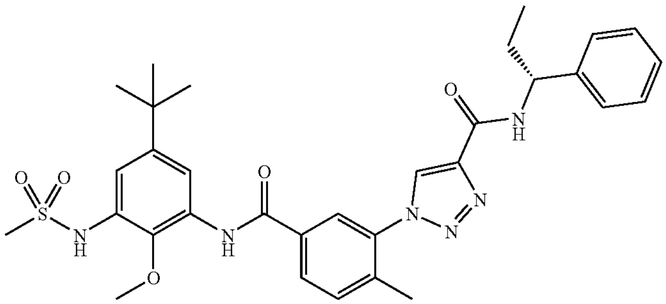 | 1-[5-(5-tert-Butyl-3-methanesulfonylamino-2-methoxy-phenylcarbamoyl)-2-methyl-phenyl]-1H-1,2,3-triazole-4-carboxylic acid ((R)-1-phenyl-propyl)-amide |
| 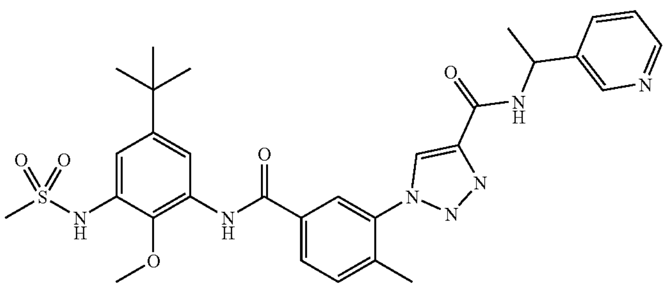 | 1-[5-(5-tert-Butyl-3-methanesulfonylamino-2-methoxy-phenylcarbamoyl)-2-methyl-phenyl]-1H-[1,2,3]triazole-4-carboxylic acid (1-pyridin-3-yl-ethyl)-amide |
| 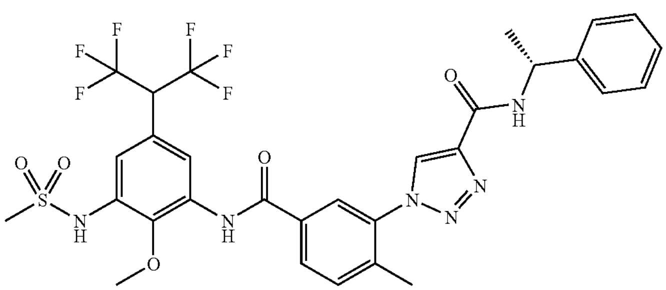 | 1-{5-[3-Methanesulfonylamino-2-methoxy-5-(2,2,2-trifluoro-1-trifluoromethyl-ethyl)-phenylcarbamoyl]-2-methyl-phenyl}-1H-[1,2,3]triazole-4-carboxylic acid ((R)-1-phenyl-ethyl)-amide |
| 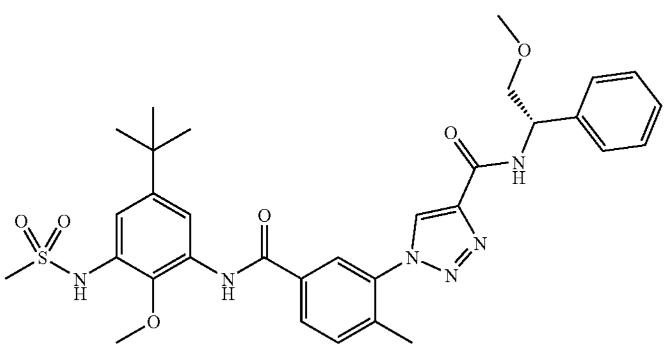 | 1-[5-(5-tert-Butyl-3-methanesulfonylamino-2-methoxy-phenylcarbamoyl)-2-methyl-phenyl]-1H-1,2,3-triazole-4-carboxylic acid ((S)-2-methoxy-1-phenyl-ethyl)-amide |
| 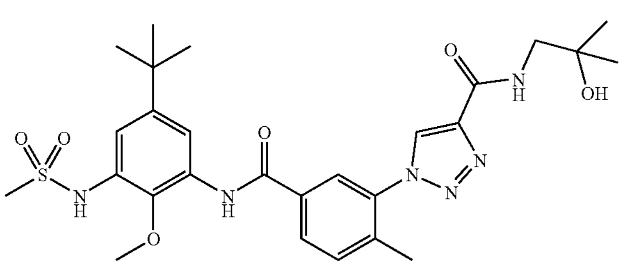 | 1-[5-(5-tert-Butyl-3-methanesulfonylamino-2-methoxy-phenylcarbamoyl)-2-methyl-phenyl]-1H-1,2,3-triazole-4-carboxylic acid (2-hydroxy-2-methyl-propyl)-amide |

TABLE III-continued

| Structure | Name |
|---|---|
| (structure) | 1-[5-(5-tert-Butyl-3-methanesulfonylamino-2-methoxy-phenylcarbamoyl)-2-methyl-phenyl]-1H-1,2,3-triazole-4-carboxylic acid (3-dimethylamino-2,2-dimethyl-propyl)-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclohexylmethyl-amide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopentylamide |
| (structure) | 1-[5-(5-tert-Butyl-3-methanesulfonylamino-2-methoxy-phenylcarbamoyl)-2-methyl-phenyl]-1H-1,2,3-triazole-4-carboxylic acid cyclopropylamide |
| (structure) | 5-Amino-1-[5-(5-tert-butyl-3-methanesulfonylamino-2-methoxy-phenylcarbamoyl)-2-methyl-phenyl]-1H!-1,2,3-triazole-4-carboxylic acid (pyridin-3-ylmethyl)-amide |

TABLE III-continued

| Structure | Name |
|---|---|
| 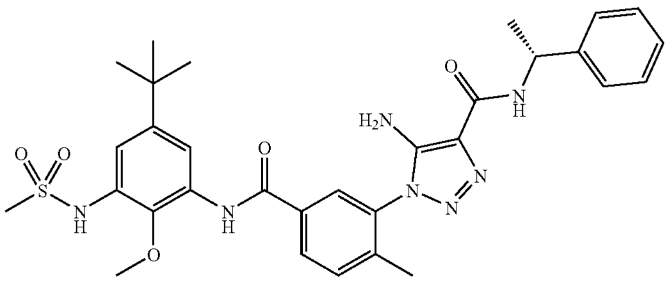 | 5-Amino-1-[5-(5-tert-butyl-3-methanesulfonylamino-2-methoxy-phenylcarbamoyl)-2-methyl-phenyl]-1H-1,2,3-triazole-4-carboxylic acid ((R)-1-phenyl-ethyl)-amide |
| 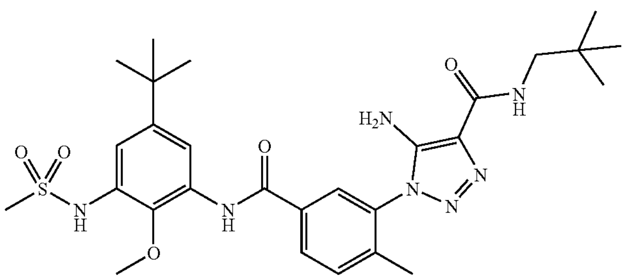 | 5-Amino-1-[5-(5-tert-butyl-3-methanesulfonylamino-2-methoxy-phenylcarbamoyl)-2-methyl-phenyl]-1H-1,2,3-triazole-4-carboxylic acid (2,2-dimethyl-propyl)-amide |
| 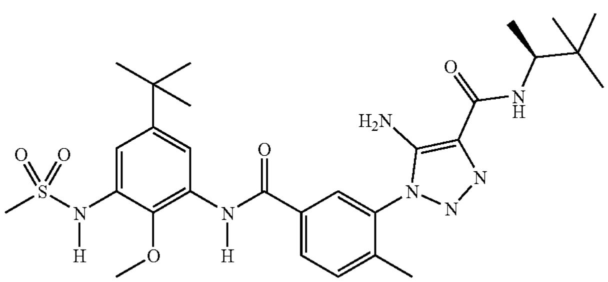 | 5-Amino-1-[5-(5-tert-butyl-3-methanesulfonylamino-2-methoxy-phenylcarbamoyl)-2-methyl-phenyl]-1H-[1,2,3]triazole-4-carboxylic acid ((S)-1,2,2-trimethyl-propyl)-amide |
| 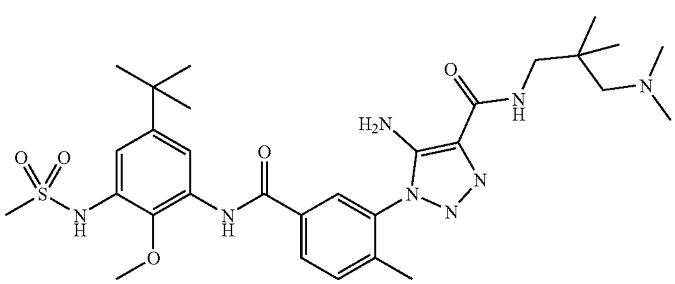 | 5-Amino-1-[5-(5-tert-butyl-3-methanesulfonylamino-2-methoxy-phenylcarbamoyl)-2-methyl-phenyl]-1H-[1,2,3]triazole-4-carboxylic acid (3-dimethylamino-2,2-dimethyl-propyl)-amide |
| 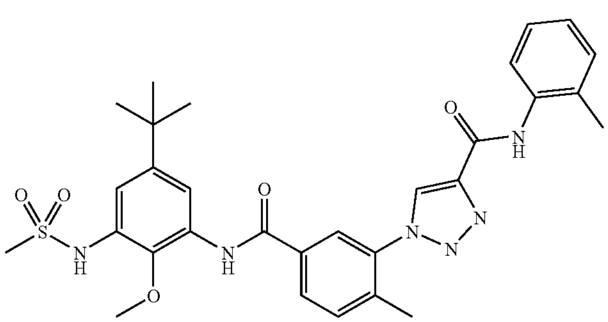 | 1-[5-(5-tert-Butyl-3-methanesulfonylamino-2-methoxy-phenylcarbamoyl)-2-methyl-phenyl]-1H-[1,2,3]triazole-4-carboxylic acid o-tolylamide |

TABLE III-continued

| Structure | Name |
|---|---|
| 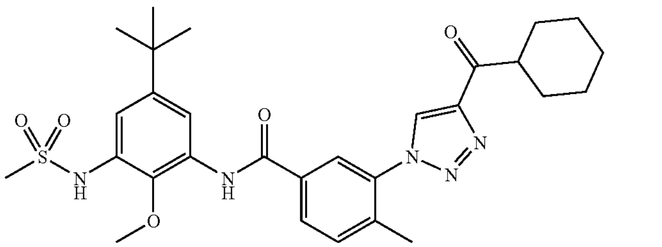 | N-(5-tert-Butyl-3-methanesulfonylamino-2-methoxy-phenyl)-3-(4-cyclohexanecarbonyl-1,2,3-triazol-1-yl)-4-methyl-benzamide |
| 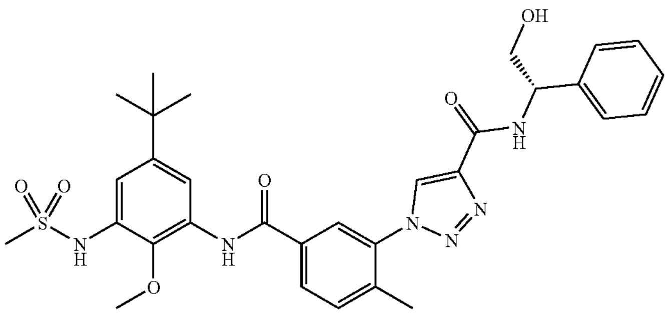 | N-(5-tert-Butyl-3-methanesulfonylamino-2-methoxy-phenyl)-3-[4-((S)-3-hydroxy-2-phenyl-propionyl)-1,2,3-triazol-1-yl]-4-methyl-benzamide |
| 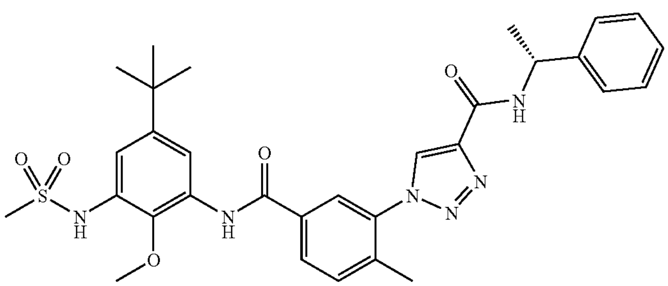 | N-(5-tert-Butyl-3-methanesulfonylamino-2-methoxy-phenyl)-4-methyl-3-[4-((R)-2-phenyl-propionyl)-1,2,3-triazol-1-yl]-benzamide |
| | 1-[5-(5-tert-Butyl-3-methanesulfonylamino-2-methoxy-phenylcarbamoyl)-2-methyl-phenyl]-1H-1,2,3-triazole-4-carboxylic acid ((S)-2-dimethylamino-1-phenyl-ethyl)-amide | or the pharmaceutically acceptable salts, acids, esters or isomers thereof.

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5–8 membered monocyclic or 8–11 membered bicyclic ring containing 1–4 heteroatoms such as N,O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$–$C_4$ alkyl)$_4$$^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The invention additionally provides for methods of making the compounds of formula (I). The compounds of the invention may be prepared by the general methods and examples presented below, and methods known to those of ordinary skill in the art. In the schemes below, unless otherwise specified, $Ar_1$, $R_1$–$R_6$ and X in the formulas shown below shall have the meanings defined for these groups in the definition of the formula (I) of the invention, described hereinabove. Intermediates used in the syntheses below are either commercially available or easily prepared by methods known to those skilled in the art. Further reference in this regard may be made to U.S. Pat. No. 6,358,945, U.S. application Ser. Nos. 09/714,539, 09/834,797, 10/120,028, 10/143,322 and 10/147,675. Each of the aforementioned are incorporated in their entirety.

Reaction progress may be monitored by conventional methods such as thin layer chromatography (TLC). Intermediates and products may be purified by methods known in the art, including column chromatography, HPLC or recrystallization.

Compounds of formula (I) having $R_5$=—$OR^a$ may be prepared as described in Scheme I.

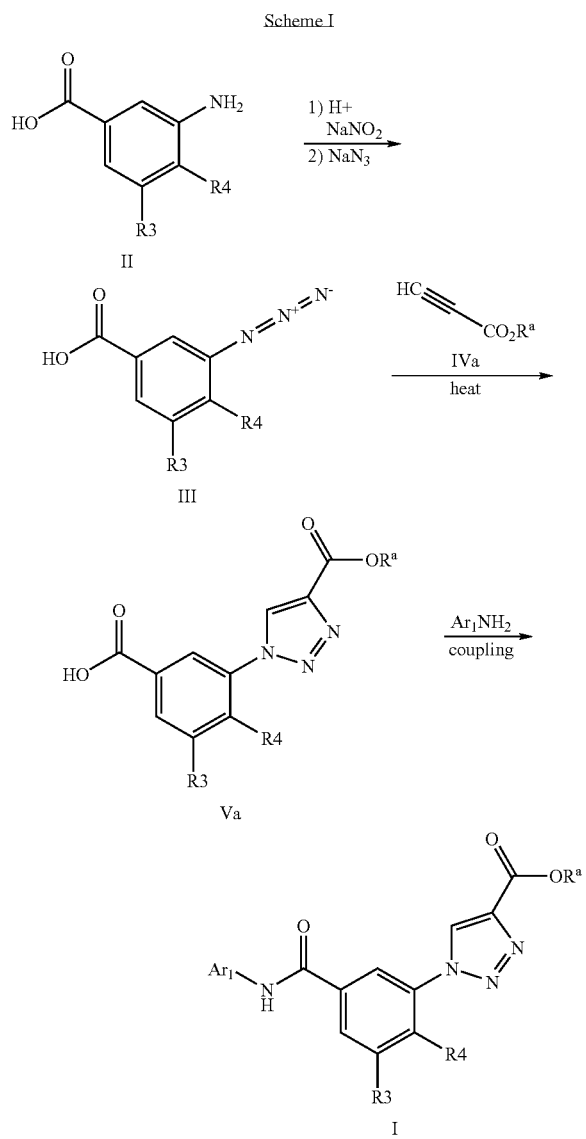

Scheme I

As illustrated in Scheme I, an optionally substituted 3-aminobenzoic acid (II) is reacted with $NaNO_2$ in an aqueous acid such as 2N HCl, at about 0° C. The diazonium salt that forms is reacted in situ with a cold aqueous solution of $NaN_3$ at about 0° C. to provide the azide III. Reaction of the azide with alkyne ester IVa in a suitable solvent such as dimethylacetamide (DMA), ethanol, or toluene while heating at about 80° C. to 120° C. in a sealed tube provides the triazole V and its regioisomer. Alternatively, an appropriate copper salt, such as CuI (Pérez-Balderas, F. et al., *Org. Lett.* 2003, 1951–1954) or $CuSO_4$ and sodium ascorbate (Rostovtsev, V. V. et al. *Angew. Chem. Int. Ed. Engl.* 2002, 41, 2596–2599), can catalyze the reaction of azide III and alkyne IVa to provide triazole V. Intermediate V is then coupled with the desired aniline $Ar_1NH_2$ by methods known in the art to produce the desired compound of formula (I) having $R_5$=$OR^a$. Coupling methods may include conversion of the benzoic acid V to the acid chloride, for example by treatment with oxalyl chloride and DMF in a suitable solvent such as dichloromethane or THF, followed by reaction with the desired aniline compound $Ar_1NH_2$ in the presence of a suitable base such as 2,6-lutidine, in a suitable solvent such as dichloromethane. Alternatively, one may react the benzoic acid V with $Ar_1NH_2$ under standard peptide coupling conditions known in the art, for example, treatment of V with 1-(3-dimethylaminopropyl)-3-ethylcarbodiimide (EDC) and 1-hydroxybenzotriazole (HOBt) in a suitable solvent such as DMF, followed by addition of $Ar_1NH_2$. The initially formed (I) may be further modified by methods known in the art to provide additional compounds of the invention. Some of these methods are illustrated in the Synthetic Examples section below.

Compounds of formula (I) in which $R_5$ is an aryl, cycloalkyl, heteroaryl or heterocyclyl group may be prepared from III as illustrated in Scheme II.

Scheme II

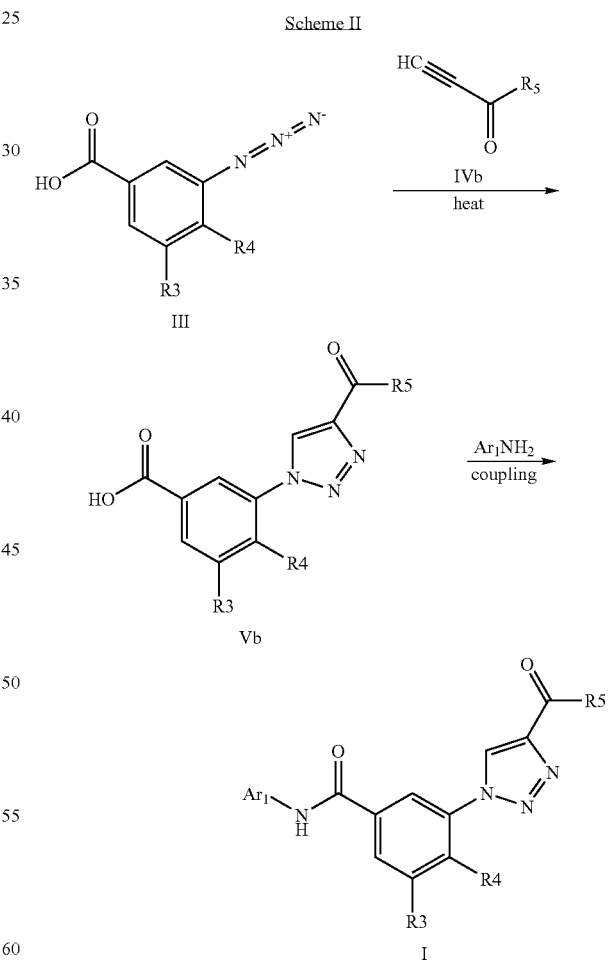

Reaction of III with an alkyne substituted with the desired $R_5$ (IVb) as described above for the alkyne ester (IVa) provides the desired ketone Vb. Coupling with $Ar_1NH_2$ as described above provides the desired compound of formula (I).

A modification of the procedure in Scheme I is illustrated in Scheme III and described below.

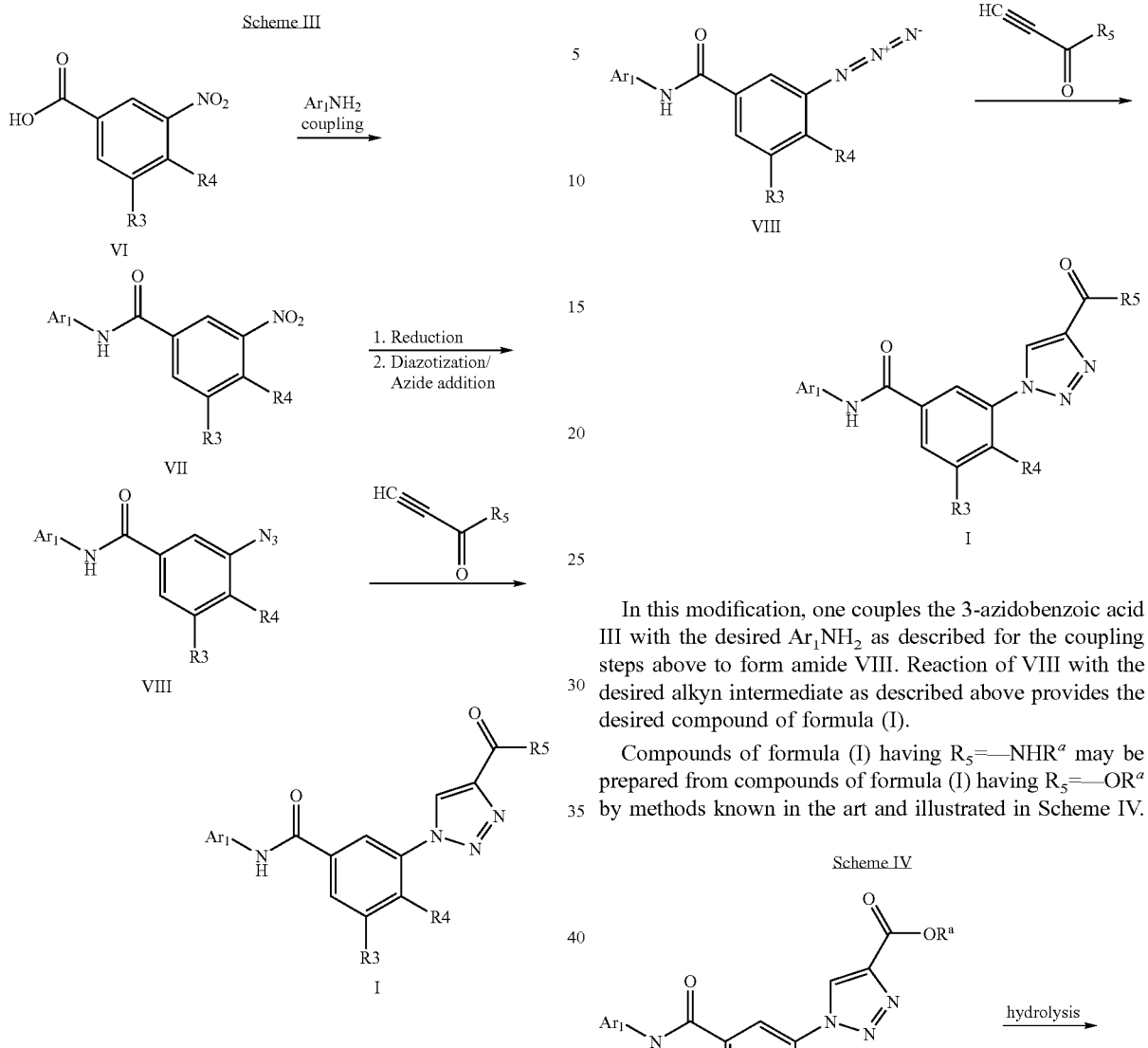

In this modification, one couples the 3-nitrobenzoic acid VI with the desired $Ar_1NH_2$ as described for the coupling steps above to form amide VII. The nitro group is then reduced by methods known in the art, for example by stirring under a hydrogen atmosphere in a suitable solvent such as MeOH with 1% HOAc, in the presence of a suitable catalyst such as palladium on carbon to provide aniline VIII. Formation of the azide followed by reaction with the desired alkyne intermediate as described above provides the desired compound of formula (I).

Another modification of the procedure in Scheme I is illustrated in Scheme IV and described below

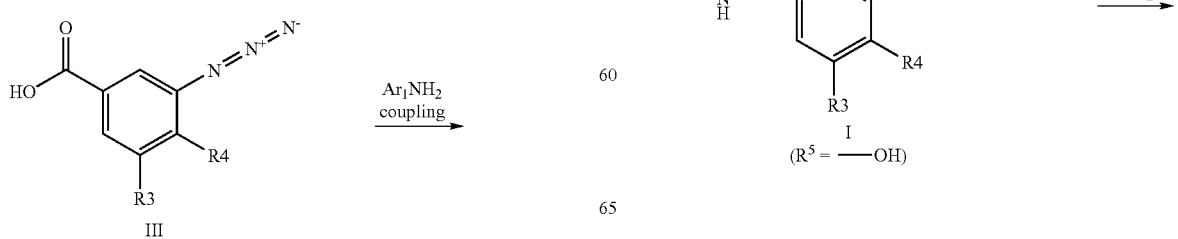

In this modification, one couples the 3-azidobenzoic acid III with the desired $Ar_1NH_2$ as described for the coupling steps above to form amide VIII. Reaction of VIII with the desired alkyn intermediate as described above provides the desired compound of formula (I).

Compounds of formula (I) having $R_5$=—$NHR^a$ may be prepared from compounds of formula (I) having $R_5$=—$OR^a$ by methods known in the art and illustrated in Scheme IV.

-continued

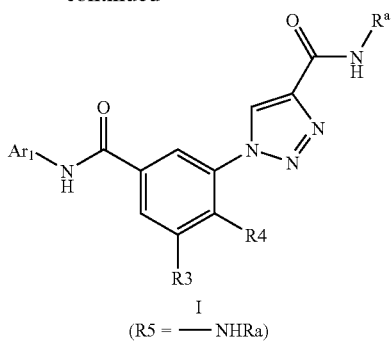

Hydrolysis of I (R=OR$^a$) for example by treatment with aqueous base in a suitable solvent such as MeOH provides carboxylic acid I (R$_5$=—OH). The carboxylic acid is then coupled with the desired amine R$^a$NH$_2$ by methods known in the art and described above and in the Synthetic Examples section below to provide the desired compound.

Aniline compounds Ar$_1$NH$_2$ are readily prepared from commercially available intermediates by methods known in the art. Further reference in this regard may be made to references cited in the first paragraph of this section.

SYNTHETIC EXAMPLES

Compound 1: N-[3-Amino-2-methoxy-5-(1-methyl-cyclopropyl)-phenyl]-methanesulfonamide

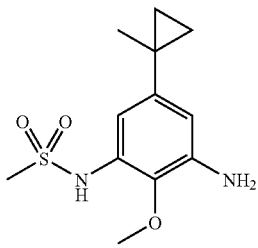

To a solution of 4-hydroxyacetophenone (10.0 g, 73.5 mmol) in DMF (74 mL) was added imidazole (12.0 g, 176.3 mmol) and tert-butyldimethylsilyl chloride (13.3 g, 88.1 mmol). The colorless solution was stirred for 0.75 h at rt then quenched with saturated aqueous NaHCO$_3$. The aqueous phase was extracted with hexanes and the combined organic layers were washed with saturated NaHCO$_3$. The organic layers were dried over sodium sulfate, filtered, and concentrated to provide 1-[4-(tert-Butyl-dimethyl-silanyloxy)-phenyl]-ethanone (18.0 g, 98%) as a white solid which was utilized without further purification. ESI MS (m/z 251, M+H).

Methyl(triphenylphosphonium) bromide (17.1 g, 48.0 mmol) was suspended in THF (96 mL) and cooled to 0° C. n-Butyllithium (2.5 M in hexane, 19.2 mL, 48.0 mmol) was added dropwise to the mixture. The red solution was stirred at rt for 0.5 h. 1-[4-(tert-Butyl-dimethyl-silanyloxy)-phenyl]-ethanone (10.0 g, 40.0 mmol) was added. The solution turned bright yellow and a white precipitate formed. The mixture was stirred for 1 h at rt and then the solution was quenched with saturated NaHCO$_3$. The aqueous phase was extracted with diethyl ether and the combined organic layers were washed with saturated NaHCO$_3$. The organic layers were dried over sodium sulfate, filtered and concentrated. The resultant mixture was eluted through a plug of silica gel (hexanes) and the filtrate was concentrated to provide tert-butyl-(4-isopropenyl-phenoxy)-dimethyl-silane (8.36 g, 84%) as a colorless oil. ESI MS (m/z 249, M+H).

Diethylzinc (1.0 M in hexanes, 69 mL, 69 mmol) was added to a solution of tert-butyl-(4-isopropenyl-phenoxy)-dimethyl-silane (6.85 g, 27.6 mmol) in dichloroethane at 0° C. Diiodomethane (11.2 mL, 138 mmol) was then added dropwise to the solution and the resultant mixture was stirred at 0° C. for 0.5 h and allowed to warm to rt for 2 h. The opaque mixture was quenched with saturated aqueous NH$_4$Cl. The aqueous phase was extracted with CH$_2$Cl$_2$ and the combined organic layers were washed with saturated aqueous NaHCO$_3$. The organic layers were dried over sodium sulfate, filtered through celite, and concentrated. The crude TBS ether was dissolved in THF (50 mL) and TBAF (1.0 M in THF, 28 mL, 28 mmol) was added at rt. The solution was stirred for 2 h and then quenched with aqueous 1.0 M HCl. The aqueous phase was extracted with ethyl acetate and the combined organic layers were washed with saturated NaHCO$_3$.

The organic layers were dried over sodium sulfate, filtered and concentrated. Purification by silica-gel chromatography (1% 2-propanol/12% ethyl acetate in hexanes) provided 4-(1-methyl-cyclopropyl)-phenol (2.77 g, 68%) as a white solid.

(NO)18-crown-6.H(NO$_3$)$_2$ (18.0 g, 43.0 mmol) was added to a solution of phenol 4-(1-methyl-cyclopropyl)-phenol (2.77 g, 18.7 mmol) in ethyl acetate. The reaction mixture was heated to reflux for 5 min and then cooled to rt. The mixture was poured onto 1.0 M HCl. The aqueous phase was extracted with diethyl ether. The combined organic layers were dried over sodium sulfate, filtered and concentrated. The residue was redissolved in acetonitrile/methanol (9:1, 62 mL), cooled to 0° C. and N,N-diisopropylethylamine (13 mL, 74.8 mmol) was added slowly. The deep red solution was warmed to rt and trimethylsilyldiazomethane (2.0 M in hexane, 18.7 mL, 37.4 mmol) was added slowly to control nitrogen evolution. After stirring at rt for 0.5 h, the mixture was concentrated and partitioned between methylene chloride and saturated NH$_4$Cl. The aqueous layer was extracted with methylene chloride and the combined extracts were dried over sodium sulfate, filtered and concentrated. Purification by silica-gel chromatography (6% ethyl acetate in hexanes) provided 2-methoxy-5-(1-methyl-cyclopropyl)-1,3-dinitro-benzene (2.21 g, 47%) as a red oil.

Tin(II)chloride dihydrate (11.9 g, 52.6 mmol) was added to a solution of 2-methoxy-5-(1-methyl-cyclopropyl)-1,3-dinitro-benzene (2.21 g, 8.76 mmol) in ethyl acetate (30 mL). The mixture was heated to reflux for 0.25 h upon which the solution became red in color. The solution was cooled to rt and poured onto aqueous 2.0 M NaOH. The aqueous phase was extracted with ethyl acetate and the combined organic layers were washed with saturated NaHCO$_3$. The organic layers were dried over sodium sulfate, eluted through a plug of silica gel (1% ammonium hydroxide in methylene chloride), and the filtrate was concentrated. The residue was redissolved in Et$_2$O and extracted (3x) with 1.0 M HCl. The pH of the combined aqueous layers was adjusted to pH=12 with 2.0M NaOH and extracted with methylene chloride. The combined organic layers were dried over sodium sulfate, filtered and concentrated to provide 2-methoxy-5-(1-methyl-cyclopropyl)-benzene-1,3-diamine (860 mg, 52%) as a red oil. ESI MS (m/z 193, M+H).

Triethylamine (521 mL, 3.74 mmol) was added to a solution of 2-methoxy-5-(1-methyl-cyclopropyl)-benzene-1,3-diamine (718 mg, 3.74 mmol) in methylene chloride at −10° C. Methanesulfonyl chloride (290 μL, 3.74 mmol) was then added dropwise over a 10 min period and the resultant solution was allowed to slowly warm to rt over 2 h. The mixture was quenched with saturated aqueous NaHCO₃ and the aqueous layer was extracted with methylene chloride. The combined organic layers were dried over sodium sulfate, filtered and concentrated. Purification by silica gel chromatography (1% ammonium hydroxide/35% ethyl acetate in hexanes to 1% ammonium hydroxide/50% ethyl acetate in hexanes) provided a red solid which was triturated with a diethyl ether/hexanes (1:1) to yield Compound 1 (510 mg, 51%) as a pale brown solid: mp 144–146° C. ESI MS (m/z 271, M+H).

Compound 2: 3-azido-4-methyl benzoic acid

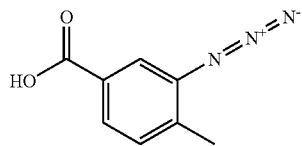

3-Amino-4-methyl benzoic acid (2.28 g, 15.1 mmol) was suspended in 65 mL of 2N HCl and chilled to 0° C. A chilled solution of 1.25 g (18.1 mmol) of NaNO₂ in 5 mL of water was added slowly, and the solution was stirred for 30 min. The mixture was filtered through a plug of diatomaceous earth, and then returned to a 0° C. bath where 1.08 g (16.6 mmol) of NaN₃ dissolved in about 5 mL of water was slowly added. Gas evolved immediately, and a precipitate formed. The precipitate was filtered, washed with water, and dried under a stream of air to provide 2.34 g (13.4 mmol; 88%) of Compound 2 as a white solid.

The following were prepared in a manner analogous to Compound 2.

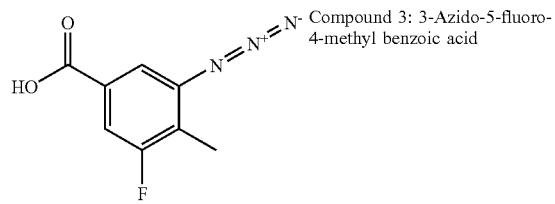

Compound 3: 3-Azido-5-fluoro-4-methyl benzoic acid

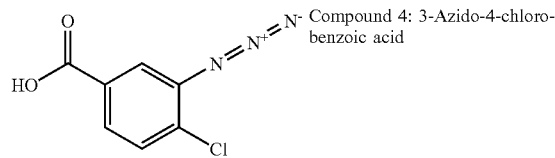

Compound 4: 3-Azido-4-chloro-benzoic acid

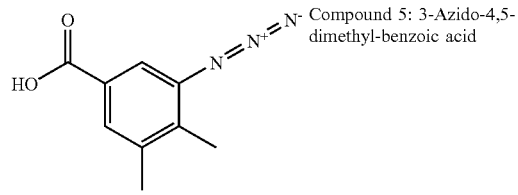

Compound 5: 3-Azido-4,5-dimethyl-benzoic acid

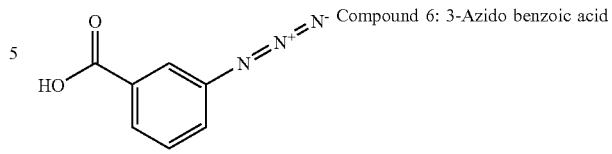

Compound 6: 3-Azido benzoic acid

Compound 7: 3-Azido-4-methyl-benzoic acid

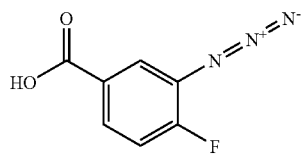

A mixture of 1.04 g (5.62 mmol) 3-nitro-4-fluoro benzoic acid and 105 mg of Pd/C in 10 mL of TFA was stirred for 12 h under an H₂ atmosphere. The mixture was then filtered through celite and the filter cake was washed with 20 mL of TFA. The pale yellow solution was then stirred under N₂ at 0° C. for 10 min and 405 mg (5.87 mmol) of NaNO₂ was added in small portions over 15 min. After an additional 15 min, 400 mg (6.15 mmol) of NaN₃ was then added carefully in portions. Gas evolved slowly, and after 1 h the mixture was poured over 20 mL of water and 50 mL of ice. After the ice had melted, the resulting precipitate was filtered and washed with water and hexanes, then dried under vacuum to provide 964 mg of Compound 7 as a white powder.

Compound 8: 3-Azido-N-(5-tert-butyl-3-methane-sulfonylamino-2-methoxy-phenyl)-5-fluoro-4-methyl-benzamide

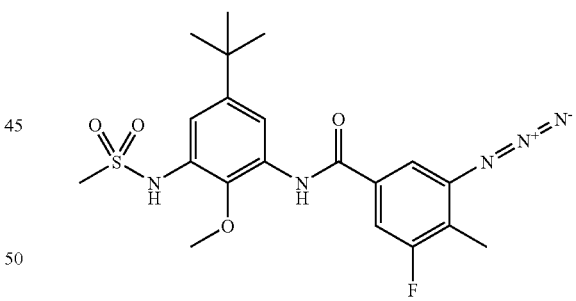

Compound 3 (241 mg, 1.24 mmol) was suspeneded in 3 mL of dichloromethane and 3 mL of THF. Oxalyl choride (0.14 mL, 1.5 mmol) was added, followed by 1 drop of 10% DMF in THF. Gas evolved immediately, and the mixture became homogeneous within 10 min. The mixture was stirred for a total of 1 h, and then concentrated to provide an off-white solid. The residue was re-dissolved in dry dichloromethane (5 mL) and 391 mg (1.27 mmol) of N-(3-Amino-5-tert-butyl-2-methoxy-phenyl)-methanesulfonamide hydrochloride was added followed by 0.44 mL (2.5 mmol) of iPr₂EtN. The mixture became homogeneous, and was stirred for 4 h, then 10 mL of dichloromethane was added and the solution was washed with 1M NaHSO₄ and sat'd. NaHCO₃. The extract was dried with Na₂SO₄, filtered, and concentrated to provide 516 mg of Compound 8 as a pale-brown powder.

Compound 9: 3-Azido-N-(5-tert-butyl-3-methanesulfonylamino-2-methoxy-phenyl)-4-fluoro-benzamide was prepared from Compound 7 in a manner analogous to Compound 8

Example 1

Synthesis of 1-[5-(5-tert-butyl-3-methanesulfonylamino-2-methoxy-phenylcarbamoyl)-2-methyl-phenyl]-1H-1,2,3-triazole-4-carboxylic acid methyl ester

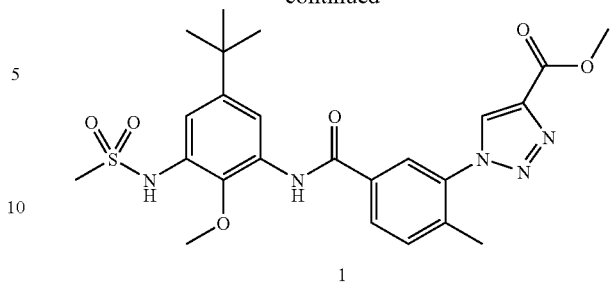

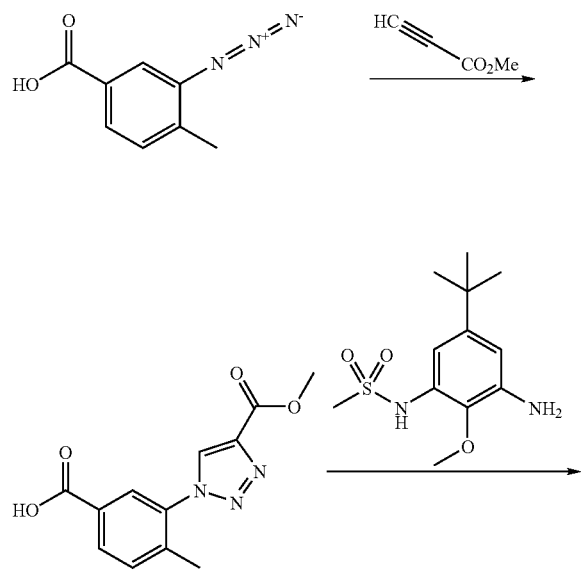

A mixture of 1.11 g (6.27 mmol) of 3-azido-4-methyl benzoic acid (Compound 2) and 1.12 mL (12.5 mmol) of methyl propiolate, was stirred in 4.2 mL of DMA at 110° C. in a sealed tube overnight. The resulting brown solution was poured into water, and the resulting precipitate was filtered, and then recrystallized from EtOH/water to provide 1.02 g (62.3%) of 1-(5-carboxy-2-methyl-phenyl)-1H-1,2,3-triazole-4-carboxylic acid methyl ester as tan crystals. ESI MS (m/z 262, 100, M+1)

1-(5-Carboxy-2-methyl-phenyl)-1H-1,2,3-triazole-4-carboxylic acid methyl ester (0.444 g, 1.70 mmol) was suspended in 15 mL of dichloromethane and 5 mL of THF. Oxalyl chloride (0.185 mL, 2.13 mmol) was added to the stirring slurry, and 2 drops of DMF followed. After 30 min, the clear tan solution was concentrated to provide an off-white solid. This residue was taken up in 15 mL of dichloromethane, and 0.50 g (1.62 mmol) of N-(3-amino-5-tert-butyl-2-methoxy-phenyl)-methanesulfonamide hydrochloride was added, resulting in a slurry. Then 2,6-lutidine (0.50 mL, 4.9 mmol) was added, and the mixture became homogeneous. After 2 h, the mixture was diluted with 15 mL of dichloromethane, then was washed with 1M NaHSO$_4$ and saturated NaHCO$_3$. The dichloromethane portion was dried and concentrated, then chromatographed with 0–7.5% MeOH in dichloromethane to provide 789 mg (1.53 mmol; 95%) of Example 1 as a white fluffy solid, mp 198° C. ESI MS (m/z 514, 100, M−H).

The following compound was prepared with the appropriate acid and aniline coupling partners in a manner analogous to Example 1.

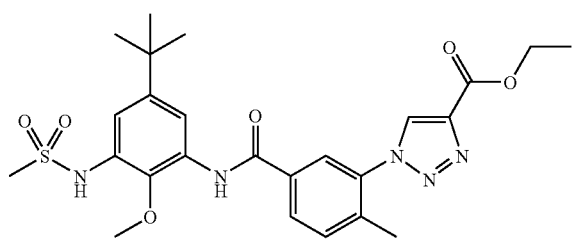

Example 2: 1-[5-(5-tert-Butyl-3-methanesulfonylamino-2-methoxy-phenylcarbamoyl)-2-methyl-phenyl]-1H-1,2,3-triazole-4-carboxylic acid ethyl ester ESI MS (m/z 528, 100, M − H)

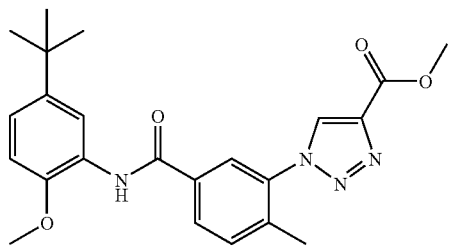

Example 3: 1-[5-(5-tert-Butyl-2-methoxy-phenylcarbamoyl)-2-methyl-phenyl]-1H-1,2,3-triazole-4-carboxylic acid methyl ester, ESI MS (m/z 423, 100, M − H).

-continued

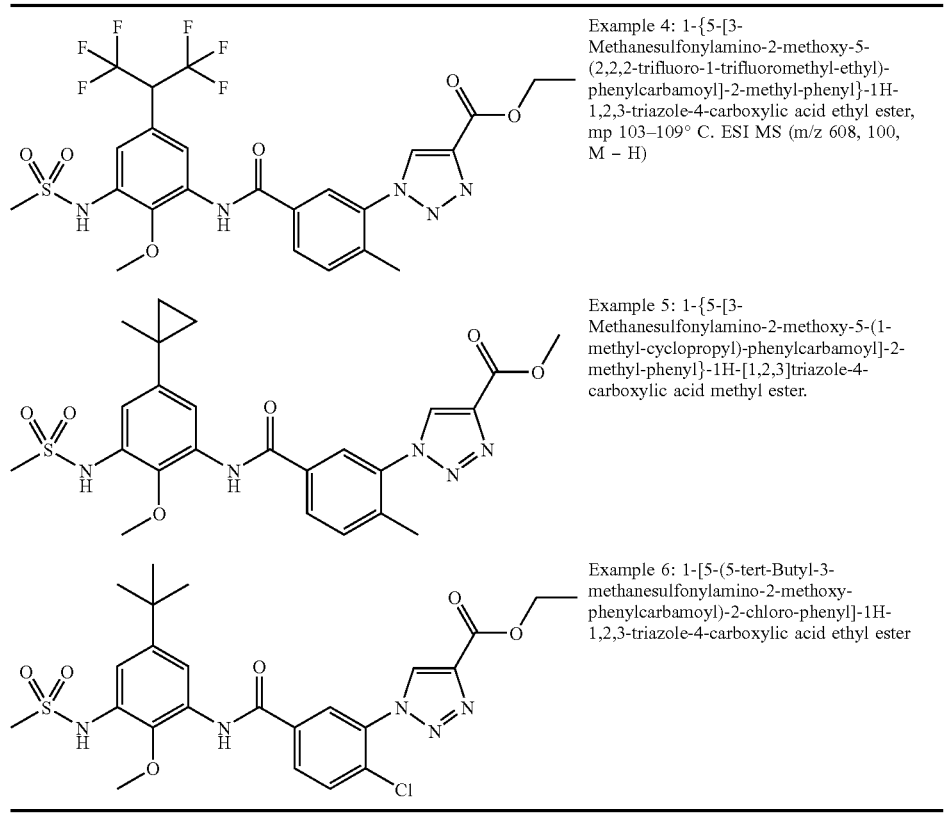

Example 4: 1-{5-[3-Methanesulfonylamino-2-methoxy-5-(2,2,2-trifluoro-1-trifluoromethyl-ethyl)-phenylcarbamoyl]-2-methyl-phenyl}-1H-1,2,3-triazole-4-carboxylic acid ethyl ester, mp 103–109° C. ESI MS (m/z 608, 100, M – H)

Example 5: 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid methyl ester.

Example 6: 1-[5-(5-tert-Butyl-3-methanesulfonylamino-2-methoxy-phenylcarbamoyl)-2-chloro-phenyl]-1H-1,2,3-triazole-4-carboxylic acid ethyl ester

Example 7

1-[5-(5-tert-Butyl-3-methanesulfonylamino-2-methoxyphenyl-carbamoyl)-3-fluoro-2-methyl-phenyl]-1H-[1,2,3]triazole-4-carboxylic acid ethyl ester

Example 8

1-[5-(5-tert-butyl-3-methanesulfonylamino-2-methoxyphenyl-carbamoyl)-2-chloro-phenyl]-1H-1,2,3-triazole-4-carboxylic acid methyl ester

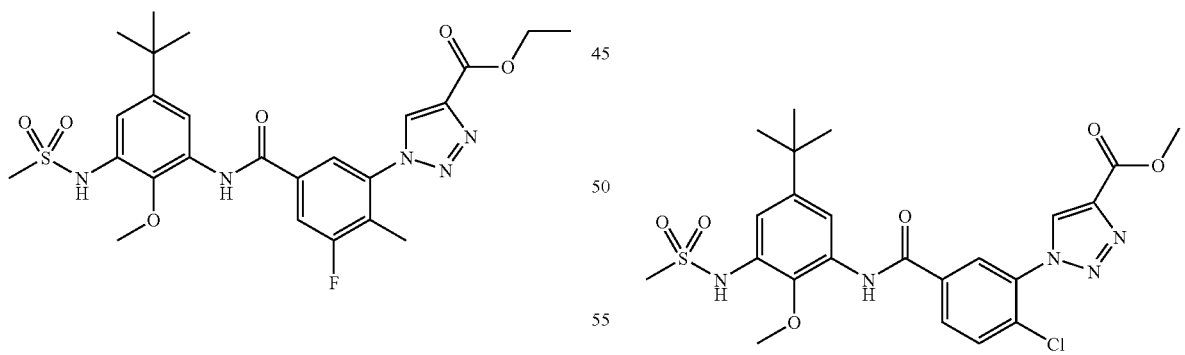

Compound 8 (252 mg, 0.561 mmol) was suspended in 1.5 mL of EtOH and 1 mL of water. 4N NaOH was added dropwise until the solution became homogeneous. Then 111 mg of Na-ascorbate, 0.06 mL (0.58 mmol) of ethylpropiolate, and 0.56 mL of 0.1 M aq. CuSO$_4$ solution were added in sequence to the rapidly stirring solution. The resulting yellow suspension was stirred rapidly for 4 h. The mixture was poured into ice-cold water and HOAc was added to bring the pH to 4. The resulting precipitate was filtered, and dried to provide 117 mg of Example 7. ESI MS (m/z 546, 100, M–H).

Example 6 (115 mg, 209 mmol) 4 mL of MeOH and 0.4 mL of 4M HCl in dioxane in a sealed tube at 60° C. for 6 h. The vessel was carefully vented at about 55° C. and 1 mL of water was added. The solution was slowly cooled, and the resulting precipitate was filtered and washed with water to provide 68.3 mg (127 mmol, 61%) of Example 8, mp 251–252° C. (dec.). ESI MS (m/z 534, 100, M–H).

Example 9

5-amino-1-[5-(5-tert-butyl-3-methanesulfonylamino-2-methoxy-phenylcarbamoyl)-2-methyl-phenyl]-1H-1,2,3-triazole-4-carboxylic acid methyl ester

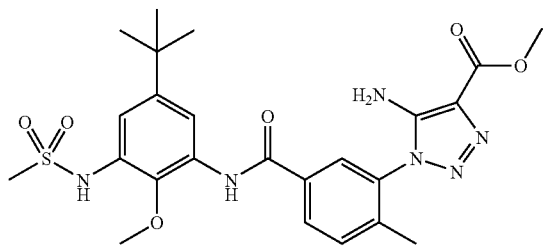

Sodium metal (241 mg, 10.5 mmol) was dissolved in dry MeOH (3.4 mL) under nitrogen. Methylcyanoacetate (0.31 mL, 3.5 mmol) was added and a solid formed in the flask. 3-Azido-N-(5-tert-butyl-3-methanesulfonylamino-2-methoxy-phenyl)-4-methyl-benzamide (1.50 g, 3.5 mmol) was added in one portion. The reaction was heated at 60° C. for approximately 1 h. The reaction was quenched with sat'd NH₄Cl solution and diluted with water. The pH was adjusted to 8 with 1 N HCl. The resulting solid was collected by vacuum filtration and washed with water. The solid was dissolved in CH$_2$Cl$_2$ and washed with brine. The organic layer was dried over Na$_2$SO$_4$, filtered and concentrated. The resulting residue was recrystallized from MeOH and ethyl acetate. The resulting solid was collected by vacuum filtration and washed with hexanes to provide Example 9 (1.14 g, 61%) as a white solid: mp 204–205° C. ESI MS (m/z 531, 100, M+H).

Example 10

Synthesis of 3-(4-benzoyl-1,2,3-triazol-1-yl)-N-(5-tert-butyl-3-methanesulfonylamino-2-methoxy-phenyl)-4-methyl-benzamide

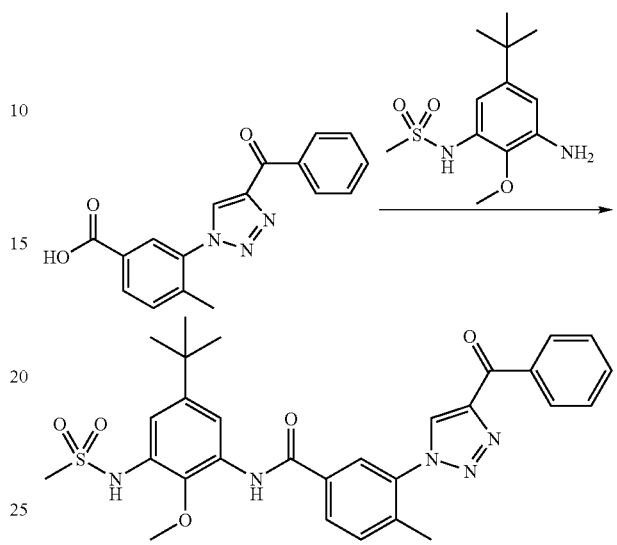

3-(4-Benzoyl-1,2,3-triazol-1-yl)-4,5-dimethyl-benzoic acid was prepared in 53.6% yield from 1-phenylpropynone in a manner analogous to the preparation of 1-(5-carboxy-2-methyl-phenyl)-1H-1,2,3-triazole-4-carboxylic acid methyl ester described in Example 1.

3-(4-Benzoyl-1,2,3-triazol-1-yl)-4,5-dimethyl-benzoic acid (57 mg, 0.185 mmol) and 42 mg (0.277 mmol) of 1-hydroxybenzotriazole hydrate (HOBt) were dissolved in 0.5 mL of DMF. 1-(3-Dimethylaminopropyl)-3-ethylcarbodiimide hydrochloride (EDC) 39 (0.204 mmol) was added, and the mixture stirred for 20 min, after which time 50 mg (0.185 mmol) of N-(3-amino-5-tert-butyl-2-methoxy-phenyl)-methanesulfonamide was added. The mixture was then poured into water and the resulting precipitate was filtered, dried in vacuo and chromatographed (0–4% MeOH in CH$_2$Cl$_2$) to provide 28 mg (26.7% yield) of Example 10 as an off-white solid. mp: 212–124° C. ESI MS (m/z 560, 100, M–H).

The following compounds were prepared by methods analogous to Example 10, using the appropriate propynone and azides.

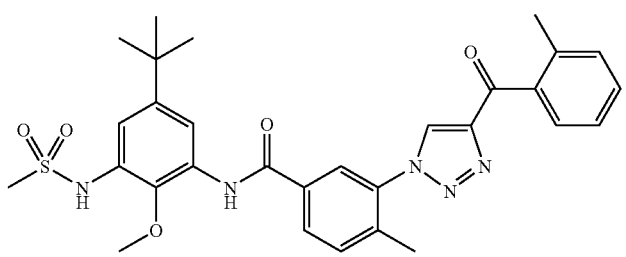

Example 11: N-(5-tert-Butyl-3-methanesulfonylamino-2-methoxy-phenyl)-4-methyl-3-[4-(2-methyl-benzoyl)-1,2,3-triazol-1-yl]-benzamide, ESI MS (m/z 576, 100, M + H)

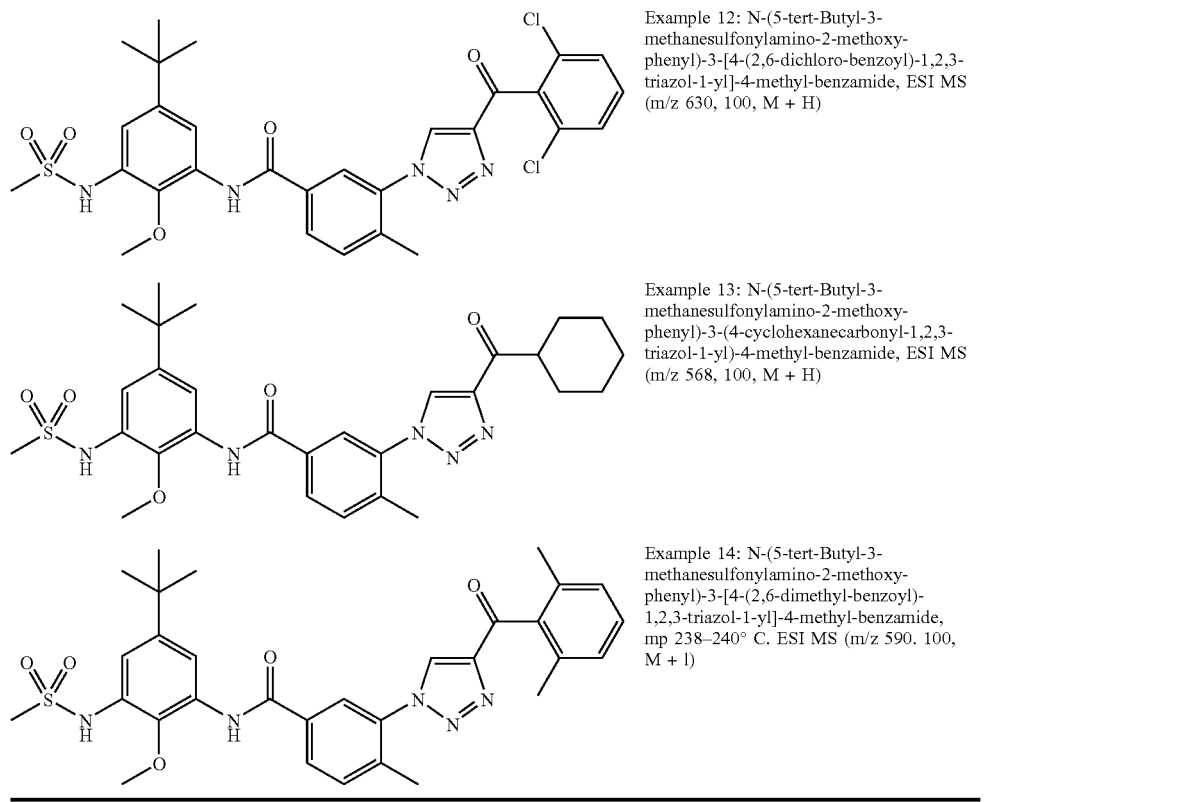

| | |
|---|---|
| | Example 12: N-(5-tert-Butyl-3-methanesulfonylamino-2-methoxy-phenyl)-3-[4-(2,6-dichloro-benzoyl)-1,2,3-triazol-1-yl]-4-methyl-benzamide, ESI MS (m/z 630, 100, M + H) |
| | Example 13: N-(5-tert-Butyl-3-methanesulfonylamino-2-methoxy-phenyl)-3-(4-cyclohexanecarbonyl-1,2,3-triazol-1-yl)-4-methyl-benzamide, ESI MS (m/z 568, 100, M + H) |
| | Example 14: N-(5-tert-Butyl-3-methanesulfonylamino-2-methoxy-phenyl)-3-[4-(2,6-dimethyl-benzoyl)-1,2,3-triazol-1-yl]-4-methyl-benzamide, mp 238–240° C. ESI MS (m/z 590. 100, M + 1) |

Example 15

Synthesis of 1-[5-(3-methanesulfonylamino-2-methoxy-5-trifluoromethyl-phenylcarbamoyl)-2-methyl-phenyl]-1H-1,2,3-triazole-4-carboxylic acid methyl ester

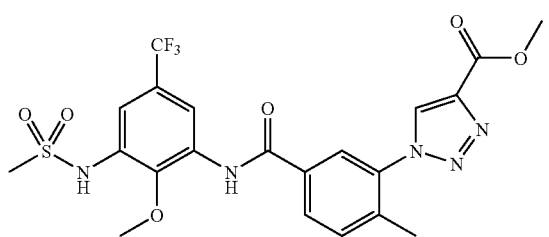

1-(5-Carboxy-2-methyl-phenyl)-1H-1,2,3-triazole-4-carboxylic acid methyl ester (26 mg, 0.101 mmol) was stirred with 21 mg (0.153 mmol) of 1-hydroxy-7-azabenzotriazole (HOAt) in 1 mL of DMF and 24 mg (0.126 mmol) of EDC was added. After 1 h of stirring at about 10° C., 30 mg (0.106 mmol) of N-(3-amino-2-methoxy-5-trifluoromethyl-phenyl)-methanesulfonamide was added. The mixture was stirred overnight then heated to 60° C. for 6 h. The reaction was then cooled and water was added. The precipitate was collected and chromatographed twice by preparative TLC (5% MeOH in CH$_2$Cl$_2$) and once by flash chromatography (0–4.5% MeOH in dichloromethane). The pure fractions yielded 3 mg (5.6%) of the title compound. ESI MS (m/z 526, 100, M–H).

Example 16

Synthesis of 1-[5-(5-tert-butyl-3-methanesulfonylamino-2-methoxy-phenylcarbamoyl)-2,3-dimethyl-phenyl]-1H-1,2,3-triazole-4-carboxylic acid methyl ester

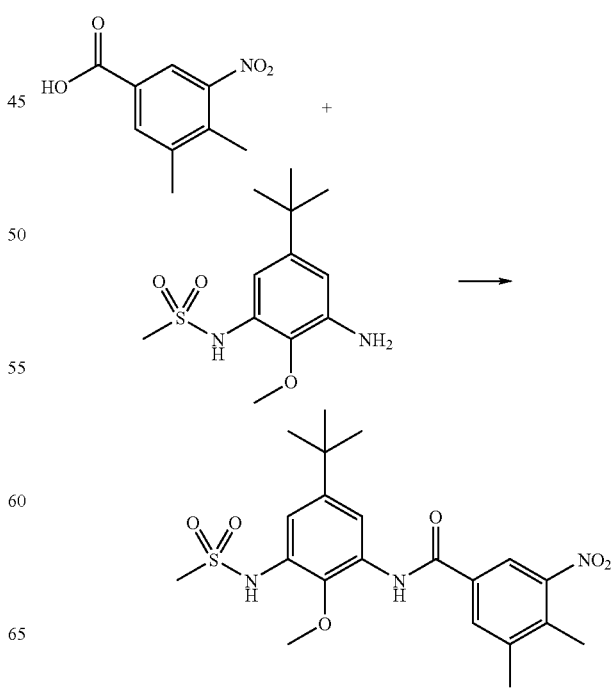

-continued

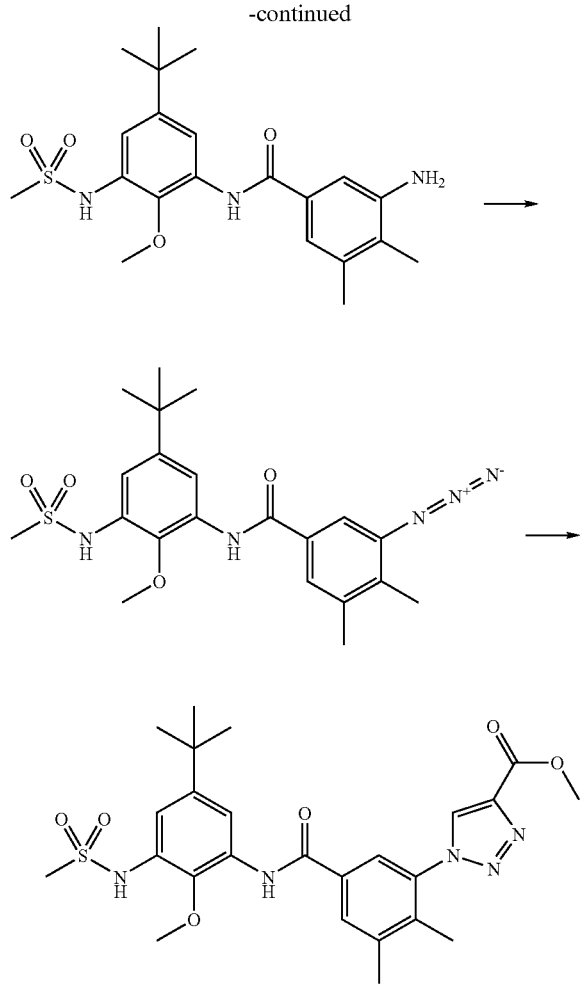

To a solution of 0.133 g (0.681 mmol) of 3-nitro-4,5-dimethyl benzoic acid in 2 mL of dichloromethane (10% THF) was added 89 μL (1.02 mmol) of oxalyl chloride. One drop of 25% DMF in dichloromethane was added to the stirring solution, and gas was rapidly evolved. After 30 min the solvent was removed and the residue dried in vacuo.

The resulting acid chloride was then re-dissolved in dry dichloromethane and N-(3-amino-5-tert-butyl-2-methoxy-phenyl)-methanesulfonamide (0.177 g, 0.650 mmol) was added, followed by 79 μL (0.681 mmol) of 2,6-lutidine. The mixture was stirred overnight, then concentrated and chromatographed (10–50% EtOAc in hexanes) to provide 234 mg (0.521 mmol, 80%) of (N-(5-tert-butyl-3-methanesulfonylamino-2-methoxy-phenyl)-3,4-dimethyl-5-nitro-benzamide), mp: 189° C. (dec) ESI MS (m/z 448, 100, M−H).

N-(5-tert-Butyl-3-methanesulfonylamino-2-methoxy-phenyl)-3,4-dimethyl-5-nitro-benzamide (0.198, 0.440 mmol) was dissolved in warm MeOH with 1% HOAc, and 20 mg of Pd/C was added. The mixture was cooled to room temperature and stirred under an atmosphere of $H_2$ for 6 h. The mixture was filtered through diatomaceous earth and concentrated. The resulting residue was taken up in EtOAc, and washed with $NaHCO_3$ and brine. The organic portion was then dried with $Na_2SO_4$, filtered, and concentrated. The residue was chromatographed with 0–7.5% MeOH in dichloromethane to provide 184 mg (0.439, 99.7%) of the aniline product. The resulting aniline (0.186 g, 0.443 mmol) was suspended in 1 M $H_2SO_4$ (about 5 mL), and a solution of 37 mg (0.53 mmol) $NaNO_2$ was slowly added. After 10 min, the aniline had not dissolved, and MeOH was slowly added until a homogeneous solution was obtained. The mixture was then diluted with 20 mL of water, and a solution of $NaN_3$ (32 mg, 0.49 mmol) in 2 mL of water was slowly added. Gas was evolved and a precipitate formed. The mixture was stirred for 1 h, and then chilled to 0° C. The precipitate was filtered and washed with water, then dried to provide 3-azido-N-(5-tert-butyl-3-methanesulfonylamino-2-methoxy-phenyl)-4,5-dimethyl-benzamide, 121 mg, 0.272 mmol.

A mixture of 0.112 g (0.252 mmol) of 3-azido-N-(5-tert-butyl-3-methanesulfonylamino-2-methoxy-phenyl)-4,5-dimethyl-benzamide and 0.069 mL (0.756 mmol) of methyl propiolate was stirred in 0.5 mL of DMA at 110° C. overnight. The vial was cooled to room temperature, and the contents were poured into stirring water. The precipitate was collected and chromatographed (10–60% EtOAc in hexanes). Fractions containing predominantly the major product were collected and further purified by precipitating from dichloromethane with hexanes to provide 57 mg of a white powder. The filtrate was combined with the mixed fractions from the first chromatography, and the resulting mixture was chromatographed again to provide 22 mg of the title compound as a pale yellow solid for a total yield of 79 mg (0.149 mmol; 59%), mp: 199° C. ESI MS (m/z 528, 100, M−H).

Example 17

Synthesis of 1-[5-(5-tert-butyl-3-methanesulfonylamino-2-methoxy-phenylcarbamoyl)-2-methyl-phenyl]-1H-1,2,3-triazole-4-carboxylic acid

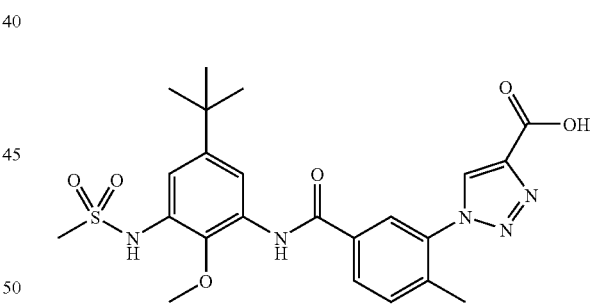

Example 1 (0.271 g, 0.525 mmol) was suspended in 2 mL of MeOH and 10 mL of 10% NaOH solution was slowly added. The solid dissolved quickly, and the solution was stirred rapidly for about 1 h. Concentrated HCl was added dropwise until a pH<2 was achieved, and the resulting white slurry was stirred until it cooled to room temperature. The precipitate was filtered and washed with water and dried under a stream of air to provide 0.250 g (0.498 mmol) of Example 17 as a white solid, mp: 222–224° C. ESI MS (m/z 500, 100, M−H).

The following Intermediates were prepared from their methyl or ethyl esters by a procedure analogous to Example 17:

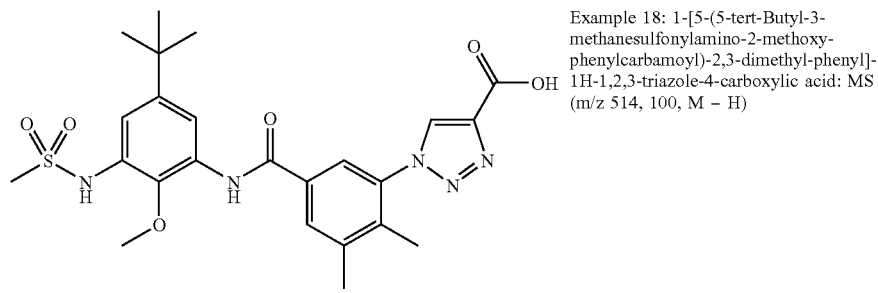

Example 18: 1-[5-(5-tert-Butyl-3-methanesulfonylamino-2-methoxy-phenylcarbamoyl)-2,3-dimethyl-phenyl]-1H-1,2,3-triazole-4-carboxylic acid: MS (m/z 514, 100, M − H)

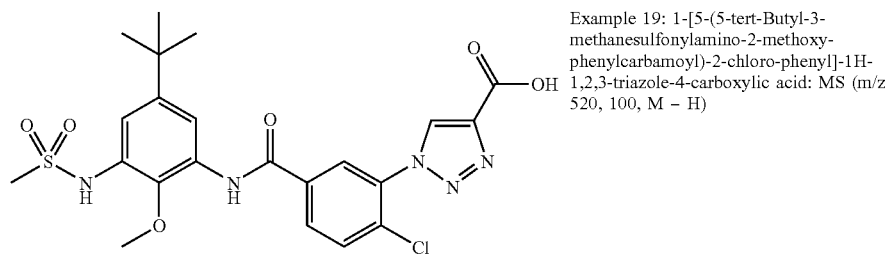

Example 19: 1-[5-(5-tert-Butyl-3-methanesulfonylamino-2-methoxy-phenylcarbamoyl)-2-chloro-phenyl]-1H-1,2,3-triazole-4-carboxylic acid: MS (m/z 520, 100, M − H)

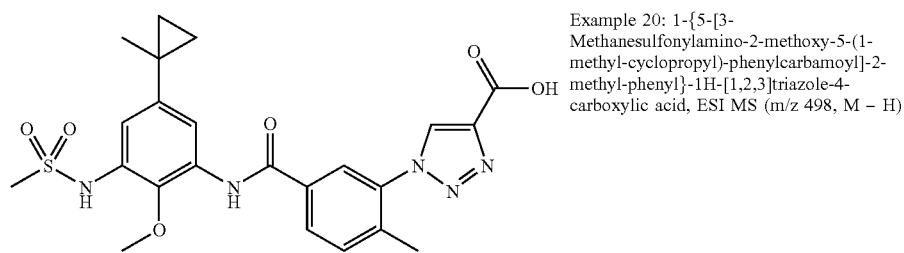

Example 20: 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid, ESI MS (m/z 498, M − H)

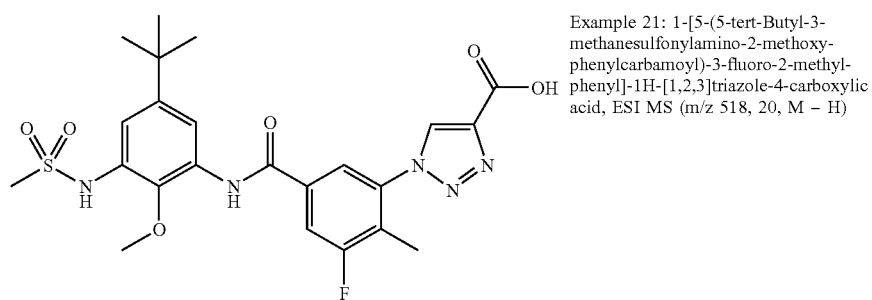

Example 21: 1-[5-(5-tert-Butyl-3-methanesulfonylamino-2-methoxy-phenylcarbamoyl)-3-fluoro-2-methyl-phenyl]-1H-[1,2,3]triazole-4-carboxylic acid, ESI MS (m/z 518, 20, M − H)

Example 22 (Intermediate)

5-Amino-1-[5-(5-tert-butyl-3-methanesulfonylamino-2-methoxy-phenylcarbamoyl)-2-methyl-phenyl]-1H-[1,2,3]triazole-4-carboxylic acid

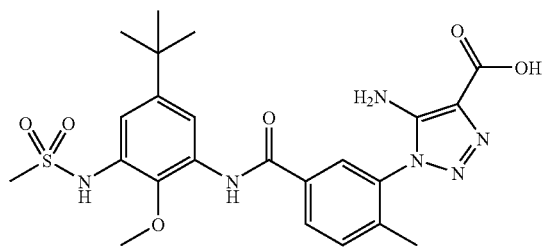

5-Amino-1-[5-(5-tert-butyl-3-methanesulfonylamino-2-methoxy-phenylcarbamoyl)-2-methyl-phenyl]-1H-1,2,3-triazole-4-carboxylic acid methyl ester (Example 9) (500 mg) was dissolved in MeOH (4 mL). A solution of 10% sodium hydroxide (20 mL) was added. The reaction was stirred for 5 h and then acidified to pH 4 with concentrated hydrochloric acid. The suspension was cooled in ice and the solid was collected by vacuum filtration, washed with water and dried under vacuum overnight. The solid was chromatographed over silica gel (6:3:1 chloroform/MeOH/ammonium hydroxide) to provide Example 22 (375 mg, 77%) as a white solid.

Example 23 (Intermediate)

1-[5-(5-tert-Butyl-3-methanesulfonylamino-2-methoxy-phenylcarbamoyl)-2-fluoro-phenyl]-1H-[1,2,3]triazole-4-carboxylic acid ethyl ester

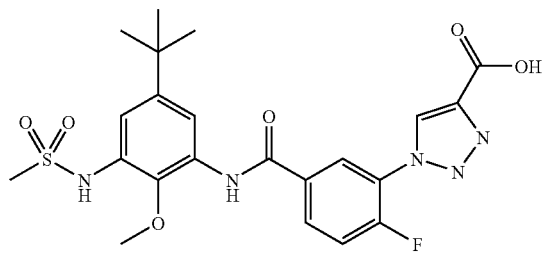

Compound 9 (500 mg, 1.15 mmol) was suspended in 4 mL of EtOH and 4N NaOH was added until the pH was ca. 10 and all of the azide had dissolved. A fresh solution of Na-ascorbate in 3 mL of water, 0.14 mL (1.38 mmol) of ethyl acrylate, and 1.15 mL of 0.1 M aq. $CuSO_4$ solution were added in sequence to the rapidly stirring mixture. MeOH was added as necessary to facilitate stirring. After 30 min, 10 mL of water was added and the conc. HCl was added until the pH reached 2. The resulting precipitate (a mixture of ethyl and methyl esters) was filtered and dried. The solids were then suspended in 10 mL of MeOH and 3 mL of 4N NaOH was added. After stirring for 30 min, the suspension was filtered through celite and the filter cake was washed with MeOH. The filtrate was concentrated to ca. 5 mL, and then was added to 100 mL of ice-water. The pH was adjusted to ca. 2 with conc. HCl, and the resulting fluffy white precipitate was filtered and washed with water to deliver 472 mg of Example 23 along with 20% of its triazole isomer. Recrystallization from MeOH provided isomerically enriched prodcuct (>10:1).

Example 24

Synthesis of 1-[5-(5-tert-butyl-3-methanesulfonylamino-2-methoxy-phenylcarbamoyl)-2-methyl-phenyl]-1H-1,2,3-triazole-4-carboxylic acid benzylamide

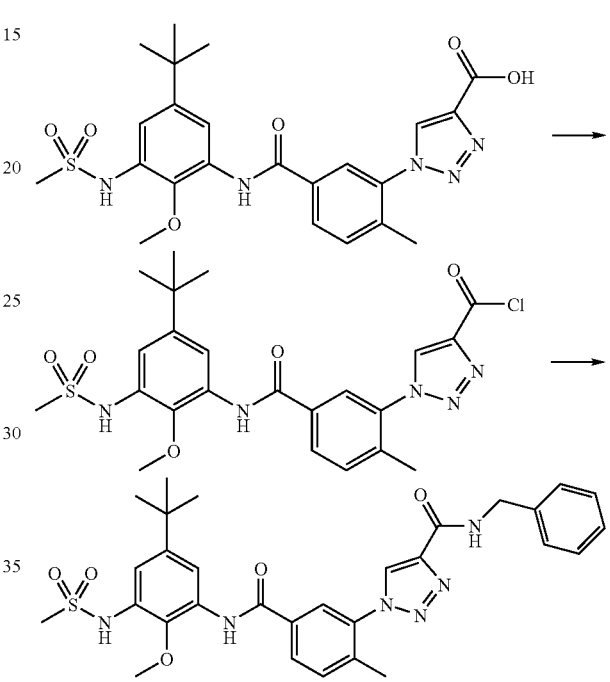

Example 17 was suspended in $CH_2Cl_2$ at 0° C. Oxalyl chloride was added, followed by 1 drop of 10% DMF in THF. The mixture was stirred for 30 min, and the resulting yellow solution was concentrated to provide 1-[5-(5-tert-butyl-3-methanesulfonylamino-2-methoxy-phenylcarbamoyl)-2-methyl-phenyl]-1H-1,2,3-triazole-4-carbonyl chloride.

To the 0.065 g (0.125 mmol) of the above acid chloride in 0.5 mL of $CH_2Cl_2$ was added 0.028 mL (0.260 mmol) of benzylamine and 0.029 mL (0.260 mmol) N-methylmorpholine. The mixture was stirred for 2 h, then concentrated and chromatographed with 0–5% MeOH in $CH_2Cl_2$ to provide Example 24, mp: 205–207° C. ESI MS (m/z 589, 100, M–H).

The following examples were prepared from the appropriate acid and amine coupling partners in a manner analogous to Example 24.

Example 25

N-(5-tert-Butyl-3-methanesulfonylamino-2-methoxy-phenyl)-4-methyl-3-[4-(morpholine-4-carbonyl)-1,2,3-triazol-1-yl]-benzamide, mp: 244–245° C. ESI MS (m/z 569, 100, M–H)

Example 26

1-[5-(5-tert-Butyl-3-methanesulfonylamino-2-methoxy-phenylcarbamoyl)-2-methyl-phenyl]-1H-1,2,3-triazole-4-carboxylic acid (1-methyl-1-phenyl-ethyl)-amide, mp: 209–210° C. ESI MS (m/z 619, 100, M+H)

Example 27

1-[5-(5-tert-Butyl-3-methanesulfonylamino-2-methoxy-phenylcarbamoyl)-2-fluoro-phenyl]-1H-[1,2,3]triazole-4-carboxylic acid (2,2-dimethyl-propyl)-amide, mp: 124–216° C. ESI MS (m/z 575, 100, M+H; 597, 60, M+Na)

Example 28

Synthesis of 1-[5-(5-tert-butyl-3-methanesulfonylamino-2-methoxy-phenylcarbamoyl)-2,3-dimethyl-phenyl]-1H-1,2,3-triazole-4-carboxylic acid (2-morpholin-4-yl-ethyl)-amide

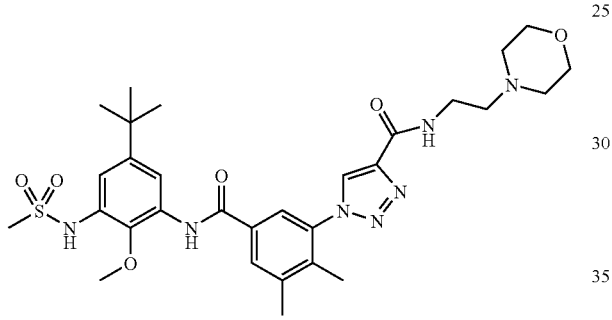

To a solution of 0.075 g (0.145 mmol) of Example 18 in 1 mL DMF was added 33 mg (0.174 mmol) of HOBt and 33 mg (0.217 mmol) of EDC. Twenty minutes later, 0.044 mL (0.290) of aminoethylmorpholine was added. The mixture was stirred for 12 h, and then poured into water, and the resulting mixture was extracted with EtOAc. The organic portion was collected, dried with $Na_2SO_4$, filtered, and concentrated. The resulting residue was chromatographed (0–10% MeOH in $CH_2Cl_2$) to provide Example 28, mp:>200° C. (dec). ESI MS (m/z 628, 100, M+H).

The following compounds were prepared from the appropriate carboxylic acid and amine by a procedure analogous to Example 28.

Example 29

1-[5-(5-tert-Butyl-3-methanesulfonylamino-2-methoxy-phenylcarbamoyl)-2-methyl-phenyl]-1H-1,2,3-triazole-4-carboxylic acid (2-morpholin-4-yl-ethyl)-amide, mp: 210 (dec). ESI MS (m/z 614, 100, M+H)

Example 30

1-[5-(5-tert-Butyl-3-methanesulfonylamino-2-methoxy-phenylcarbamoyl)-2-methyl-phenyl]-1H-1,2,3-triazole-4-carboxylic acid methylamide, mp 224–225° C. ESI MS (m/z 515, 100, M+1)

Example 31

1-[5-(5-tert-Butyl-3-methanesulfonylamino-2-methoxy-phenylcarbamoyl)-2-methyl-phenyl]-1H-1,2,3-triazole-4-carboxylic acid (2,2-dimethyl-propyl)-amide, mp 230–234° C. ESI MS (m/z 571, 100, M+H)

Example 32

1-[5-(5-tert-Butyl-3-methanesulfonylamino-2-methoxy-phenylcarbamoyl)-2-methyl-phenyl]-1H-1,2,3-triazole-4-carboxylic acid cyclopentylmethyl-amide, mp: 248–251° C. ESI MS (m/z 583, 100, M+H)

Example 33

1-[5-(5-tert-Butyl-3-methanesulfonylamino-2-methoxy-phenylcarbamoyl)-2-methyl-phenyl]-1H-1,2,3-triazole-4-carboxylic acid (pyridin-3-ylmethyl)-amide, mp: 220–222° C. ESI MS (m/z 592, 100, M+H)

Example 34

1-[5-(5-tert-Butyl-3-methanesulfonylamino-2-methoxy-phenylcarbamoyl)-2-methyl-phenyl]-1H-1,2,3-triazole-4-carboxylic acid (pyridin-4-ylmethyl)-amide, mp: 186–189° C. ESI MS (m/z 592, 100, M+H)

Example 35

1-[5-(5-tert-Butyl-3-methanesulfonylamino-2-methoxy-phenylcarbamoyl)-2-methyl-phenyl]-1H-1,2,3-triazole-4-carboxylic acid (2-dimethylamino-ethyl)-amide, mp: 224–226° C. ESI MS (m/z 572, 100, M+H)

Example 36

1-[5-(5-tert-Butyl-2-methoxy-phenylcarbamoyl)-2-methyl-phenyl]-1H-1,2,3-triazole-4-carboxylic acid benzylamide, mp: 106–109° C. ESI MS (m/z 498, 100, M+H)

Example 37

1-[5-(5-tert-Butyl-2-methoxy-phenylcarbamoyl)-2-methyl-phenyl]-1H-1,2,3-triazole-4-carboxylic acid (2-morpholin-4-yl-ethyl)-amide, mp: 198–200° C. ESI MS (m/z 521, 100, M+H)

Example 38

1-[5-(5-tert-Butyl-2-methoxy-phenylcarbamoyl)-2-methyl-phenyl]-1H-1,2,3-triazole-4-carboxylic acid ((R)-1-phenyl-ethyl)-amide, mp: 128–131° C. ESI MS (m/z 512, 100, M+H)

Example 39

N-(5-tert-Butyl-3-methanesulfonylamino-2-methoxy-phenyl)-3-[4-((S)-3-hydroxy-2-phenyl-propionyl)-1,2,3-triazol-1-yl]4-methyl-benzamide, mp: 147–150° C. ESI MS (m/z 621100, M+H)

Example 40

1-[5-(5-tert-Butyl-3-methanesulfonylamino-2-methoxy-phenylcarbamoyl)-2-methyl-phenyl]-1H-1,2,3-triazole-4-carboxylic acid ((R)-1-cyclohexyl-ethyl)-amide, mp: 266–268° C. ESI MS (m/z 611, 100, M+H)

Example 41

1-[5-(5-tert-Butyl-3-methanesulfonylamino-2-methoxy-phenylcarbamoyl)-2-methyl-phenyl]-1H-1,2,3-triazole-4-carboxylic acid ((R)-1,2,2-trimethyl-propyl)-amide, mp: 234–236° C. ESI MS (m/z 585, 100, M+H)

Example 42

1-[5-(5-tert-Butyl-3-methanesulfonylamino-2-methoxy-phenylcarbamoyl)-2-methyl-phenyl]-1H-1,2,3-triazole-4-carboxylic acid ((S)-2-methoxy-1-phenyl-ethyl)-amide, mp: 229–231° C. ESI MS (m/z 635, 100, M+H)

Example 43

4-[({1-[5-(5-tert-Butyl-3-methanesulfonylamino-2-methoxy-phenylcarbamoyl)-2-methyl-phenyl]-1H-1,2,3-triazole-4-carbonyl}-amino)-methyl]-piperidine-1-carboxylic acid tert-butyl ester, mp: 202° C. ESI MS (m/z 698, 100, M+H)

Example 44

1-[5-(5-tert-Butyl-3-methanesulfonylamino-2-methoxy-phenylcarbamoyl)-2,3-dimethyl-phenyl]-1H-1,2,3-triazole-4-carboxylic acid benzylamide, mp: 191 (dec.). ESI MS (m/z 605, 100, M+H)

Example 45

1-[5-(5-tert-Butyl-3-methanesulfonylamino-2-methoxy-phenylcarbamoyl)-2-methyl-phenyl]-1H-1,2,3-triazole-4-carboxylic acid cyclopropylmethyl-amide, mp: 247–248° C. ESI MS (m/z 555, 100, M+H)

Example 46

N-(5-tert-Butyl-3-methanesulfonylamino-2-methoxy-phenyl)-4-methyl-3-[4-((R)-2-phenyl-propionyl)-1,2,3-triazol-1-yl]-benzamide, mp: 227–232° C. ESI MS (m/z 605, 100, M+H)

Example 47

1-[5-(5-tert-Butyl-3-methanesulfonylamino-2-methoxy-phenylcarbamoyl)-2-methyl-phenyl]-1H-1,2,3-triazole-4-carboxylic acid ((S)-1-phenyl-ethyl)-amide, mp: 227–230° C. ESI MS (m/z 605, 100, M–H)

Example 48

1-[5-(5-tert-Butyl-3-methanesulfonylamino-2-methoxy-phenylcarbamoyl)-2-methyl-phenyl]-1H-1,2,3-triazole-4-carboxylic acid cyclohexylmethyl-amide, mp: 245–247° C. ESI MS (m/z 597, 100, M+H)

Example 49

1-[5-(5-tert-Butyl-3-methanesulfonylamino-2-methoxy-phenylcarbamoyl)-2-methyl-phenyl]-1H-1,2,3-triazole-4-carboxylic acid cyclopropylamide, mp: 245–248° C. ESI MS (m/z 541, 100, M+H)

Example 50

1-[5-(5-tert-Butyl-3-methanesulfonylamino-2-methoxy-phenylcarbamoyl)-2-methyl-phenyl]-1H-1,2,3-triazole-4-carboxylic acid (2-piperidin-1-yl-ethyl)-amide, mp: 226–231° C. ESI MS (m/z 612, 100, M+H)

Example 51

1-[5-(5-tert-Butyl-3-methanesulfonylamino-2-methoxy-phenylcarbamoyl)-2-methyl-phenyl]-1H-1,2,3-triazole-4-carboxylic acid 3-methyl-benzylamide, mp: 200–202° C. ESI MS (m/z 605, 100, M+H)

Example 52

1-[5-(5-tert-Butyl-3-methanesulfonylamino-2-methoxy-phenylcarbamoyl)-2-methyl-phenyl]-1H-1,2,3-triazole-4-carboxylic acid tert-butylamide, mp: 219–222° C. ESI MS (m/z 557, 100, M+H)

Example 53

1-[5-(5-tert-Butyl-3-methanesulfonylamino-2-methoxy-phenylcarbamoyl)-2-methyl-phenyl]-1H-1,2,3-triazole-4-carboxylic acid cyclopentylamide, mp: 264–266° C. ESI MS (m/z 569, 100, M+H)

Example 54

1-[5-(5-tert-Butyl-3-methanesulfonylamino-2-methoxy-phenylcarbamoyl)-2-methyl-phenyl]-1H-1,2,3-triazole-4-carboxylic acid (2-hydroxy-2-methyl-propyl)-amide, 242–243° C. ESI MS (m/z 571, 100, M–H)

Example 55

1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-propyl)-amide, ESI MS (m/z 637, 100, M+H)

Example 56

1-[5-(5-tert-Butyl-3-methanesulfonylamino-2-methoxy-phenylcarbamoyl)-2-methyl-phenyl]-1H-1,2,3-triazole-4-carboxylic acid ((R)-1-phenyl-propyl)-amide, ESI MS (m/z 619, 100, M+H)

Example 57

1-[5-(5-tert-Butyl-3-methanesulfonylamino-2-methoxy-phenylcarbamoyl)-2-chloro-phenyl]-1H-1,2,3-triazole-4-carboxylic acid (pyridin-3-ylmethyl)-amide, ESI MS (m/z 612, 100, M+H)

Example 58

1-[5-(5-tert-Butyl-3-methanesulfonylamino-2-methoxy-phenylcarbamoyl)-2-chloro-phenyl]-1H-1,2,3-triazole-4-carboxylic acid (2,2-dimethyl-propyl)-amide, ESI MS (m/z 591, 100, M+H)

Example 59

1-[5-(5-tert-Butyl-3-methanesulfonylamino-2-methoxy-phenylcarbamoyl)-2-methyl-phenyl]-1H-1,2,3-triazole-4-carboxylic acid ((S)-1,2,2-trimethyl-propyl)-amide, mp: 230–232° C. ESI MS (m/z 585, 100, M+H)

Example 60

1-[5-(5-tert-Butyl-3-methanesulfonylamino-2-methoxy-phenylcarbamoyl)-2-methyl-phenyl]-1H-1,2,3-triazole-4-carboxylic acid ((S)-1-cyclohexyl-ethyl)-amide, mp: 256–258° C. ESI MS (m/z 611, 100, M+H)

Example 61

1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-ethyl)-amide, ESI ESI MS (m/z 625, 21, M+H)

Example 62

1-[5-(5-tert-Butyl-3-methanesulfonylamino-2-methoxy-phenylcarbamoyl)-2-methyl-phenyl]-1H-1,2,3-triazole-4-carboxylic acid ((S)-2-dimethylamino-1-phenyl-ethyl)-amide, mp: 206–209° C. (dec). ESI MS (m/z 648, 100, M+H)

Example 63

1-[5-(5-tert-Butyl-3-dibenzylamino-2-methoxy-phenylcarbamoyl)-2-methyl-phenyl]-1H-[1,2,3]triazole-4-carboxylic acid (2,2-dimethyl-propyl)-amide. ESI MS (m/z 673, M+H)

Example 64

1-{(5-[3-Methanesulfonylamino-2-methoxy-5-(2,2,2-trifluoro-1-trifluoromethyl-ethyl)-phenylcarbamoyl]-2-methyl-phenyl}-1H-[1,2,3]triazole-4-carboxylic acid ((R)-1-phenyl-ethyl)-amide, mp: 126–129° C. ESI MS (m/z 699, 100, M+H)

Example 65

1-[5-(5-tert-Butyl-3-methanesulfonylamino-2-methoxy-phenylcarbamoyl)-3-fluoro-2-methyl-phenyl]-1H-[1,2,3]triazole-4-carboxylic acid (2,2-dimethyl-propyl)-amide, mp: 226–229° C. ESI MS (m/z 587, 100, M–H)

Example 66

1-[5-(5-tert-butyl-3-methanesulfonylamino-2-methoxyphenyl-carbamoyl)-2-methyl-phenyl]-1H-1,2,3-triazole-4-carboxylic acid amide

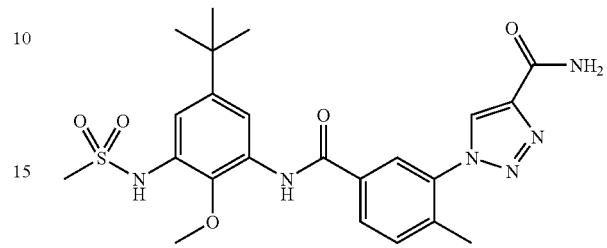

1-[5-(5-tert-Butyl-3-methanesulfonylamino-2-methoxyphenylcarbamoyl)-2-methyl-phenyl]-1H-1,2,3-triazole-4-carboxylic acid methyl ester (Example 1) (108 mg, 0.209 mmol) was suspended in 4 mL of 0.5 M $NH_3$ in MeOH in a sealed tube. The tube was then heated to 65° C. for 36 h. After cooling to room temperature, the suspension was filtered and the filter cake was washed with MeOH. The filter cake was then suspended in 20 mL of hot EtOH and DMF was added slowly until a homogeneous solution resulted. Water was slowly added until the mixture became faintly cloudy, and the mixture was removed from the heat and left to cool. The resulting precipitate was filtered, washed with EtOH and water, and dried in vacuo to provide 75 mg (71% yield) of Example 66 as a white fluffy powder, mp: >250° C. ESI MS (m/z 499, 100, M–H).

Example 67

1-[5-(5-tert-butyl-3-methanesulfonylamino-2-methoxyphenyl-carbamoyl)-2-methyl-phenyl]-1H-1,2,3-triazole-4-carboxylic acid (piperidin-4-ylmethyl)-amide

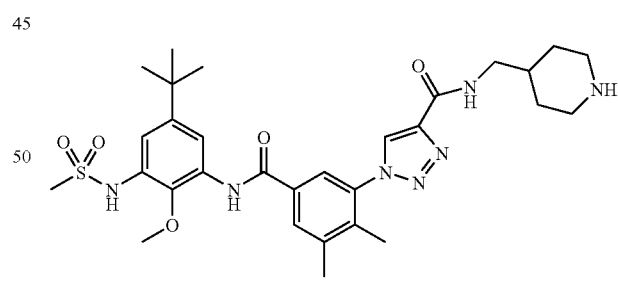

4-[({1-[5-(5-tert-Butyl-3-methanesulfonylamino-2-methoxy-phenylcarbamoyl)-2-methyl-phenyl]-1H-1,2,3-triazole-4-carbonyl}-amino)-methyl]-piperidine-1-carboxylic acid tert-butyl ester (Example 43; 93 mg, 133 mmol) was dissolved in about 5 mL of $CH_2Cl_2$, and then 0.7 mL of 4 M HCl in dioxane was added with stirring. After about 10 min, a white precipitate formed and 0.5 mL of MeOH was added. The turbid solution became clear. After 30 min total, the solvent was removed in vacuo, and the residue was partitioned between EtOAc and sat'd $NaHCO_3$. The aqueous layer was extracted twice with EtOAc and the combined organic extracts were dried with $Na_2SO_4$, filtered, concentrated, and chromatograped (0–10% B in dichloromethane: B=2% aq. $NH_4OH$, 18% MeOH, 80% dichloromethane) to provide 50 mg (63.3% yield) of Example 67 as a white powder. ESI MS (m/z 598, 25, M+H).

Example 68 (75 mg, 88%) as a white solid. mp 189–193° C. ESI MS (m/z 586, 100, M+H).

The following compound was prepared by amide bond forming reactions with the appropriate acid and amine partners in manner analogous to the above Example 68:

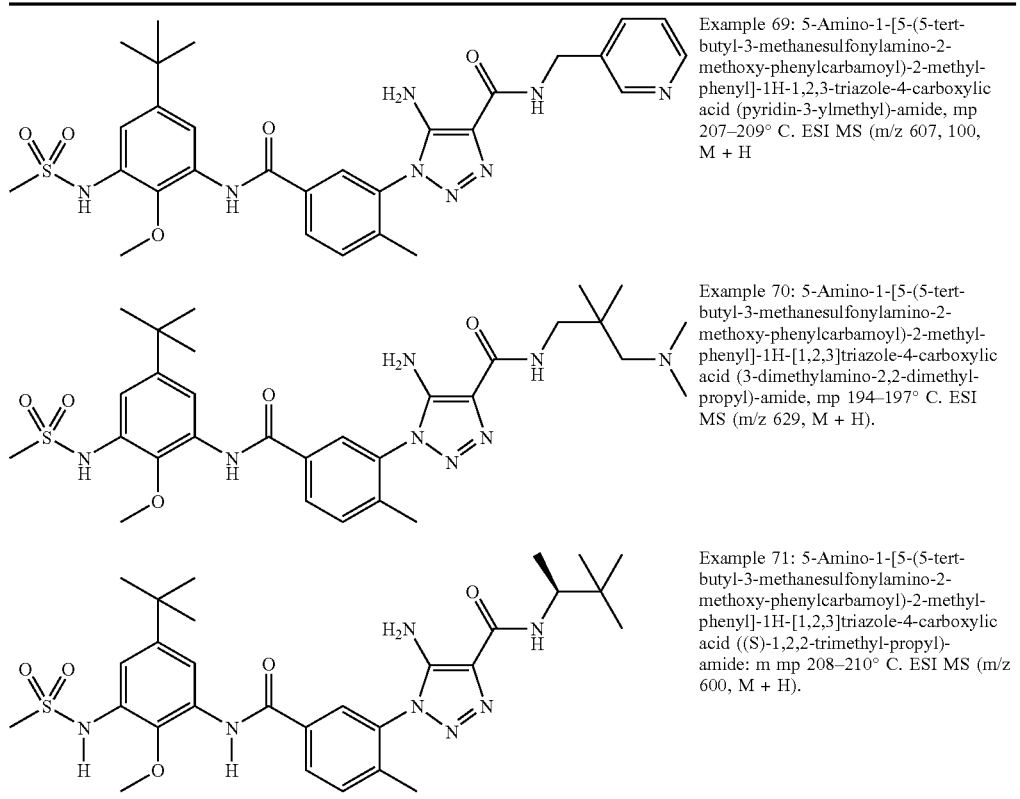

Example 69: 5-Amino-1-[5-(5-tert-butyl-3-methanesulfonylamino-2-methoxy-phenylcarbamoyl)-2-methyl-phenyl]-1H-1,2,3-triazole-4-carboxylic acid (pyridin-3-ylmethyl)-amide, mp 207–209° C. ESI MS (m/z 607, 100, M + H Example 70: 5-Amino-1-[5-(5-tert-butyl-3-methanesulfonylamino-2-methoxy-phenylcarbamoyl)-2-methyl-phenyl]-1H-[1,2,3]triazole-4-carboxylic acid (3-dimethylamino-2,2-dimethyl-propyl)-amide, mp 194–197° C. ESI MS (m/z 629, M + H).

Example 71: 5-Amino-1-[5-(5-tert-butyl-3-methanesulfonylamino-2-methoxy-phenylcarbamoyl)-2-methyl-phenyl]-1H-[1,2,3]triazole-4-carboxylic acid ((S)-1,2,2-trimethyl-propyl)-amide: m mp 208–210° C. ESI MS (m/z 600, M + H).

Example 68

5-amino-1-[5-(5-tert-butyl-3-methanesulfonylamino-2-methoxy-phenylcarbamoyl)-2-methyl-phenyl]-1H-1,2,3-triazole-4-carboxylic Acid (2,2-dimethyl-propyl)-amide

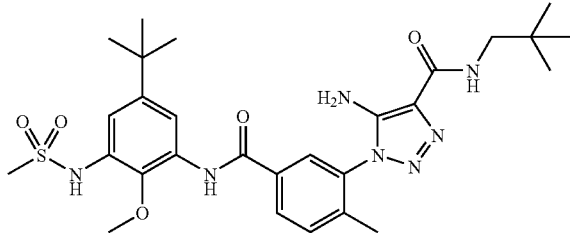

O-(7-Azabenzotriazol-1-yl)-N,N,N',N',-tetramethyluronium hexafluorophosphate (HATU) (85 mg, 0.23 mmol) and Example 22 (75 mg, 0.15 mmol) were dissolved in dry DMF (1.5 mL). Neopentylamine (18 microL, 0.23 mmol) and N,N-diisopropylethylamine (78 microL, 0.45 mmol) were added and the reaction stirred 20 min. Water (5 mL) was added and the cloudy solution was extracted with $CH_2Cl_2$ (4×15 mL). The combined organic extracts were washed with 5% lithium chloride (2×) solution and brine. The organic solution was dried over sodium sulfate, filtered and concentrated. The resulting residue was triturated with $Et_2O$ and dried under vacuum at 55° C. overnight to provide Example 72

3-[({1-[5-(5-tert-Butyl-3-methanesulfonylamino-2-methoxy-phenylcarbamoyl)-2-methyl-phenyl]-1H-[1,2,3]triazole-4-carbonyl}-amino)-methyl]-piperidine-1-carboxylic acid tert-butyl ester, mp: 200–202° C. ESI MS (m/z 696, M−H)

Example 73

1-[5-(5-tert-Butyl-3-methanesulfonylamino-2-methoxy-phenylcarbamoyl)-2-methyl-phenyl]-1H-1,2,3-triazole-4-carboxylic acid (3-dimethylamino-2,2-dimethyl-propyl)-amide, ESI MS (m/z 614, 62, M+H)

Example 74

1-[5-(5-tert-Butyl-3-methanesulfonylamino-2-methoxy-phenylcarbamoyl)-2-methyl-phenyl]-1H-[1,2,3]triazole-4-carboxylic acid (2-dimethylamino-2-methyl-propyl)-amide, mp: 190–293° C. ESI MS (m/z 600, M+H)

Example 75

1-[5-(5-tert-Butyl-3-methanesulfonylamino-2-methoxy-phenylcarbamoyl)-2-methyl-phenyl]-1H-[1,2,3]triazole-4-carboxylic acid ((R)-1-ethyl-pyrrolidin-2-ylmethyl)-amide, mp: 209–211° C. ESI MS (m/z 612, 100, M+H)

Example 76

1-[5-(5-tert-Butyl-3-methanesulfonylamino-2-methoxy-phenylcarbamoyl)-2-methyl-phenyl]-1H-[1,2,3]triazole-4-carboxylic acid ((S)-1-ethyl-pyrrolidin-2-ylmethyl)-amide, mp: 205–207° C. ESI MS (m/z 612, 100, M+H)

Example 77

1-[5-(5-tert-Butyl-3-methanesulfonylamino-2-methoxy-phenylcarbamoyl)-2-methyl-phenyl]-1H-1,2,3-triazole-4-carboxylic acid benzyl-methyl-amide, ESI MS (m/z 603, 100, M−H)

Example 78

1-[5-(5-tert-Butyl-3-methanesulfonylamino-2-methoxyphenyl-carbamoyl)-2-methyl-phenyl]-1H-[1,2,3]triazole-4-carboxylic acid ((R)-3-dimethylamino-1-phenyl-propyl)-amide, mp: 110–199° C. ESI MS (m/z 662, 100, M+H)

Example 79

1-[5-(5-tert-Butyl-3-methanesulfonylamino-2-methoxy-phenylcarbamoyl)-2-methyl-phenyl]-1H-[1,2,3]triazole-4-carboxylic acid phenylamide, mp: 263–264° C. ESI MS (m/z 557, 100, M+H)

Example 80

1-[5-(5-tert-Butyl-3-methanesulfonylamino-2-methoxy-phenylcarbamoyl)-2-methyl-phenyl]-1H-[1,2,3]triazole-4-carboxylic acid m-tolylamide, mp: 214–217° C. ESI MS (m/z 591, 100, M+H)

Example 81

1-[5-(5-tert-Butyl-3-methanesulfonylamino-2-methoxy-phenylcarbamoyl)-2-methyl-phenyl]-1H-[1,2,3]triazole-4-carboxylic acid pyridin-4-ylamide, mp: 237–240° C. ESI MS (m/z 578, 100, M+H)

Example 82

1-[5-(5-tert-Butyl-3-methanesulfonylamino-2-methoxy-phenylcarbamoyl)-2-methyl-phenyl]-1H-[1,2,3]triazole-4-carboxylic acid o-tolylamide, mp: 220–222° C. ESI MS (m/z 591, 100, M+H)

Example 83

1-[5-(5-tert-Butyl-3-methanesulfonylamino-2-methoxy-phenylcarbamoyl)-2-methyl-phenyl]-1H-[1,2,3]triazole-4-carboxylic acid p-tolylamide, mp: 268–270° C. ESI MS (m/z 591, 100, M+H)

Example 84

1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid (2,2-dimethyl-propyl)-amide, mp: 226–228° C. (dec). ESI MS (m/z 569, 100, M+H)

Example 85

1-[5-(5-tert-Butyl-3-methanesulfonylamino-2-methoxy-phenylcarbamoyl)-2-fluoro-phenyl]-1H-[1,2,3]triazole-4-carboxylic acid benzylamide, mp: 209–210° C. ESI MS (m/z 595, 100, M+H)

Example 86

1-[5-(5-tert-Butyl-3-methanesulfonylamino-2-methoxy-phenylcarbamoyl)-2-methyl-phenyl]-1H-[1,2,3]triazole-4-carboxylic acid (1-pyridin-3-yl-ethyl)-amide trifluroacetic acid salt, mp: 220–223° C. (dec). ESI MS (m/z 606, 100, M+H)

Example 87

1-[3-(5-tert-Butyl-3-methanesulfonylamino-2-methoxy-phenylcarbamoyl)-phenyl]-1H-[1,2,3]triazole-4-carboxylic acid (2,2-dimethyl-propyl)-amide, mp: 228–230° C. ESI MS (m/z 555, 100, M−H)

Example 88

1-[3-(5-tert-Butyl-3-methanesulfonylamino-2-methoxy-phenylcarbamoyl)-phenyl]-1H-[1,2,3]triazole-4-carboxylic acid benzylamide, mp: 176–179° C. ESI MS (m/z 577, 100, M+H)

Example 89

1-[3-(5-tert-Butyl-3-methanesulfonylamino-2-methoxy-phenylcarbamoyl)-phenyl]-1H-[1,2,3]triazole-4-carboxylic acid ((R)-1-phenyl-ethyl)-amide, mp: 226–229° C. ESI MS (m/z 591, 100, M+H)

Example 90

1-[5-(5-tert-Butyl-3-methanesulfonylamino-2-methoxy-phenylcarbamoyl)-2-methyl-phenyl]-1H-[1,2,3]triazole-4-carboxylic acid ((S)-2-dimethylamino-1-phenyl-ethyl)-methyl-amide, mp: 101–111° C. ESI MS (m/z 662, 100, M_H)

Example 91

5-amino-1-[5-(5-tert-butyl-3-methanesulfonylamino-2-methoxy-phenylcarbamoyl)-2-methyl-phenyl]-1H-1,2,3-triazole-4-carboxylic acid ((R)-1-phenyl-ethyl)-amide

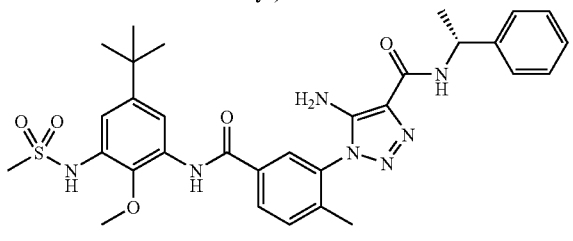

Example 22 (50 mg, 0.1 mmol), EDC (21 mg, 0.11 mmol), and HOBt (16 mg, 0.12 mmol) were dissolved in dry DMF (0.75 mL). (R)-(+)-1-methylbenzylamine (39 μL, 0.3 mmol) was added and the reaction stirred overnight. Water was added and a precipitate formed. The precipitate was collected by vacuum filtration and washed with water. The solid was dissolved in CH$_2$Cl$_2$ and dried over sodium sulfate, filtered and concentrated. The residue was chromatographed over silica gel (5% MeOH in CH$_2$Cl$_2$) to provide Example 91. ESI MS (m/z 620, 100, M+H).

Example 92

1-[5-(3-Amino-5-tert-butyl-2-methoxy-phenylcarbamoyl)-2-methyl-phenyl]-1H-[1,2,3]triazole-4-carboxylic acid (2,2-dimethyl-propyl)-amide

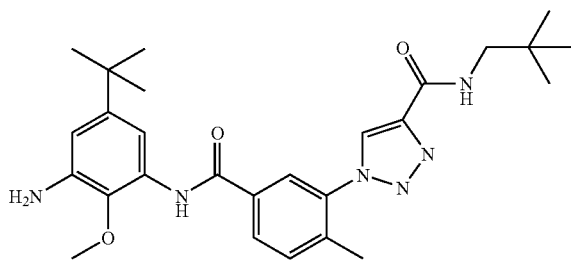

To a solution of 161 mg of 1-[5-(5-tert-Butyl-3-dibenzylamino-2-methoxy-phenylcarbamoyl)-2-methyl-phenyl]-1H-[1,2,3]triazole-4-carboxylic acid (2,2-dimethyl-propyl)-amide in 10 mL of MeOH was added 80 mg of Pd/C and 1.0 mL of 96% formic acid added. The mixture was stirred at rt for 16 h and then filtered through celite with MeOH washings. The filtrate was concentrated and redissolved in 20 mL of CH$_2$Cl$_2$ and washed with 1M NaOH (10 mL). The wash was further extracted with CH$_2$Cl$_2$ (3×20 mL). The extracts were dried, concentrated, dried with MgSO$_4$, filtered, and concentrated. Chromatography with 0 to 80% EtOAc in hexanes gave 44 mg of Example 92 as a white foam. ESI MS (m/z 593, 100, M+H).

Example 93

1-[5-(5-tert-Butyl-3-methanesulfonylamino-2-methoxy-phenylcarbamoyl)-2-methyl-phenyl]-1H-[1,2,3]triazole-4-carboxylic acid (1-methyl-piperidin-3-ylmethyl)-amide

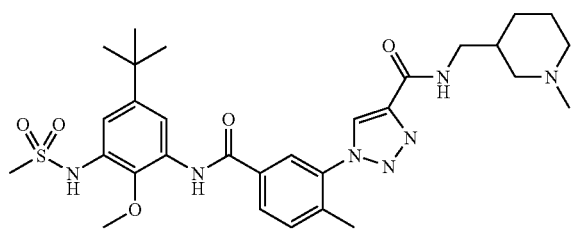

To a solution of 336 mg (0.481 mmol) of 3-[({1-[5-(5-tert-Butyl-3-methanesulfonylamino-2-methoxy-phenylcarbamoyl)-2-methyl-phenyl]-1H-[1,2,3]triazole-4-carbonyl}-amino)-methyl]-piperidine-1-carboxylic acid tert-butyl ester (Example 72) in 5 mL CH$_2$Cl$_2$ was added dropwise 1.2 mL of 4N HCl in dioxane. As a gummy yellow precipitate began to form in the flask, 10 drops of MeOH were added and the solution was stirred overnight. The mixture was partitioned between CH$_2$Cl$_2$ (75 mL) and 50% saturated aqueous NaHCO$_3$ (50 mL). The layers were separated and the aqueous portion was extracted with CH$_2$Cl$_2$ (2×30 mL). The combined extracts were washed with water (30 mL), brine (30 mL), dried (Na$_2$SO$_4$), filtered and concentrated to afford 190 mg of 1-[5-(5-tert-Butyl-3-methanesulfonylamino-2-methoxy-phenylcarbamoyl)-2-methyl-phenyl]-1H-[1,2,3]triazole-4-carboxylic acid (piperidin-3-ylmethyl)-amide as a pale yellow solid.

To a 0° C. suspension of 106 mg (0.268 mmol) of 1-[5-(5-tert-Butyl-3-methanesulfonylamino-2-methoxyphenylcarbamoyl)-2-methyl-phenyl]-1H-[1,2,3]triazole-4-carboxylic acid (piperidin-3-ylmethyl)-amide in 2 mL of MeOH containing 1% HOAc was added 70 μL of aqueous formaldehyde. The suspension was stirred at 0° C. for five minutes then 18 mg (0.281 mmol) of sodium cyanoborohydride was added and the mixture was warmed to rt. After stirring for ~1 the reaction mixture was diluted with 40 mL of CH$_2$Cl$_2$ and washed with 25 mL of water. The aqueous wash was extracted with CH$_2$Cl$_2$ (2×25 mL), the combined organic extracts were dried (Na$_2$SO$_4$), filtered and evaporated to afford a yellow solid. Chromatography provided 42 mg of product. mp: 209–211. ESI MS (m/z 612, 100, M+H).

Example 94

1-[5-(5-tert-Butyl-3-methanesulfonylamino-2-methoxy-phenylcarbamoyl)-2-methyl-phenyl]-1H-[1,2,3]triazole-4-carboxylic acid (1-methyl-piperidin-4-ylmethyl)-amide was prepared from 4-[({1-[5-(5-tert-Butyl-3-methanesulfonylamino-2-methoxy-phenylcarbamoyl)-2-methyl-phenyl]-1H-[1,2,3]triazole-4-carbonyl}-amino)-methyl]-piperidine-1-carboxylic acid tert-butyl ester in a manner analogous to Example 93. mp: 202–203° C. ESI MS (m/z 612, M+H).

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in the provisional application No. 60/403,422.

The compounds of the invention are also p38 MAP kinase inhibitors. As disclosed in the Background of the Invention, the compounds of the invention will therefore be useful for treating oncological diseases. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/ml final; Siga L-2630, from *E. coli* serotype 0111.B4; stored as 1 mg/ml stock in endotoxin screened distilled $H_2O$ at –80° C.). Blanks (unstimulated) received $H_2O$ vehicle; final incubation volume was 250 µl. Overnight incubation (18–24 hr) proceeded as described above. Assay was terminated by centrifuging plates 5 min, room temperature, 1600 rpm (400×g); supernatants were transferred to clean 96 well plates and stored –80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50} < 1$ uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

What is claimed is:
1. A compound of the formula (I)

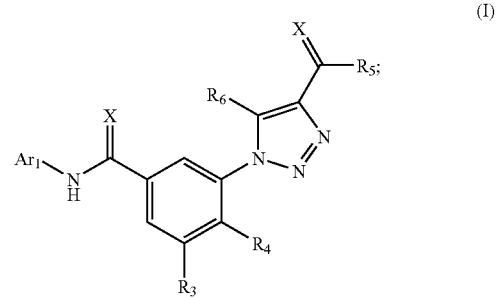

wherein:
$Ar_1$ is carbocycle substituted with one $R_1$, and wherein $Ar_1$ is independently substituted with two $R_2$ groups;
$R_1$ is $NO_2$, —$N(R^c)_2$, J-C(O)—N($R^c$)— or J-S(O)$_m$—N($R^c$)—
m is 0, 1 or 2
and wherein $R^c$ is chosen from hydrogen or C1–5 alkyl;
J is chosen from C1–10 alkyl and carbocycle each optionally substituted by $R^b$;
$R_2$ is chosen from C1–6 alkyl or C3–7 cycloalkyl which may optionally be partially or fully halogenated, C1–4 acyl, aroyl, C1–4 alkoxy, which may optionally be partially or fully halogenated, halogen, C1–6 alkoxycarbonyl, carbocyclesulfonyl and —$SO_2$—$CF_3$;
$R_3$, $R_4$, $R_5$, $R_7$ and $R_8$ are each independently chosen from hydrogen, halogen, C1–5 alkyl, C1–5 alkoxy, C1–5 alkylC1–5 alkoxy, hydroxy, hydroxy C1–5 alkyl or amino optionally mono- or di-substituted by C1–5 alkyl, aryl or aryl C1–5 alkyl;
$R_5$ is chosen from a bond, —O—, —S—, —N<, —NH—, C(O), a linear chain chosen from —NH(CR$_7$R$_8$)$_n$—, —(CR$_7$R$_8$)$_n$—, —O(CR$_7$R$_8$)$_n$—, —C(O)—O(CR$_7$R$_8$)$_n$—, —S(CR$_7$R$_8$)$_n$—, C(O)(CR$_7$R$_8$)$_n$— and —C(O)NH(CR$_7$R$_8$)$_n$—, wherein n is 1–5 and each of the aforementioned $R_5$ is further substituted by $R^a$,
or $R_5$ is aryl optionally substituted by $R^a$;
$R^a$ and $R^b$ are each independently chosen from hydrogen, C1–5 alkyl, hydroxyC1–5 alkyl, C2–5 alkenyl, C2–5 alkynyl, carbocycle, C1–5 alkoxy, C1–5 alkylthio, amino, C1–5 alkylamino, C1–5 dialkylamino, C1–5 acyl, C1–5 alkoxycarbonyl, C1–5 acyloxy, C1–5 acylamino, each of the aforementioned are optionally partially or fully halogenated, or $R^a$ and $R^b$ are chosen from C1–5 alkylsulphonylamino, hydroxy, oxo, halogen, nitro and nitrile, and
each X is independently O or S
or the pharmaceutically acceptable salts, acids, esters or isomers thereof.
2. The compound according to claim 1 wherein:
J is chosen from C1–10 alkyl, aryl or C3–7 cycloalkyl each optionally substituted by $R^b$;
$R_2$ is independently chosen from C1–6 alkyl which may optionally be partially or fully halogenated, acetyl, aroyl, C1–4 alkoxy, which may optionally be partially or fully halogenated, halogen, methoxycarbonyl, phenylsulfonyl and —$SO_2$—$CF_3$;
n is 1–4;
$R^a$ and $R^b$ are each independently chosen from hydrogen, C1–5 alkyl, C2–5 alkenyl, C2–5 alkynyl, C3–8 cycloalkylC0–2 alkyl, aryl, C1–5 alkoxy, C1–5 alkylthio, amino, C1–5 alkylamino, C1–5 dialkylamino, C1–5 acyl, C1–5 alkoxycarbonyl, C1–5 acyloxy, C1–5 acylamino, C1–5 sulphonylamino, hydroxy, halogen, trifluoromethyl, nitro and nitrile;

$R_7$ is hydrogen;

and each X is O.

3. The compound according to claim 2 wherein $R_5$ is chosen from —O—, —S—, —NH—, C(O), a linear chain chosen from —NH(CR$_7$R$_8$)$_n$—, —(CR$_7$R$_8$)$_n$—, —O(CR$_7$R$_8$)$_n$—, —C(O)—O(CR$_7$R$_8$)$_n$—, —S(CR$_7$R$_8$)$_n$—, C(O)(CR$_7$R$_8$)$_n$— and —C(O)NH(CR$_7$R$_8$)$_n$—, wherein n is 1–3 and each of the aforementioned $R_5$ is further substituted by $R^a$.

4. The compound according to claim 3 wherein $Ar^1$ is chosen from cyclopropyl, cyclobutyl, cyclopentyl, cyclohexyl and cycloheptyl, phenyl, naphthyl, tetrahydronaphthyl, indanyl and indenyl, $R^1$ is $NO_2$, $NH_2$, C1–3acylNH— or the formula:

J-S(O)$_m$—N(R$^c$)—;

J is C1–10 alkyl;

$R_2$ is independently chosen from C1–6 alkyl which may optionally be partially or fully halogenated and C1–3 alkoxy, which may optionally be partially or fully halogenated;

$R_3$ and $R_4$ are each independently chosen from hydrogen, C1–3 alkyl and chloro;

$R_6$ is chosen from hydrogen and amino;

$R_5$ is: —NH—, C(O), a linear chain chosen from —NH(CR$_7$R$_8$)$_n$—, —(CR$_7$R$_8$)$_n$—, —O(CR$_7$R$_8$)$_n$—, —C(O)—O(CR$_7$R$_8$)$_n$—, C(O)(CR$_7$R$_8$)$_n$— and —C(O)NH(CR$_7$R$_8$)$_n$— wherein n is 1–2 and each of the aforementioned $R_5$ is further substituted by $R^a$, $R^a$ and $R^b$ are each independently chosen from hydrogen, C1–5 alkyl, C3–7 cycloalkylC0–2 alkyl, aryl, C1–5 alkoxy, amino, C1–5 alkylamino, C1–3 dialkylamino, C1–3 acyl, C1–5 alkoxycarbonyl, C1–3 acyloxy, C1–3 acylamino, C1–3 sulphonylamino, hydroxy, halogen, trifluoromethyl, nitro and nitrile.

5. The compound according to claim 4 wherein $Ar^1$ is

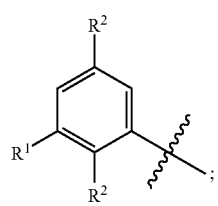

$R^1$ is the formula:

J-S(O)$_2$—NH—;

J is C1–5 alkyl;

$R_2$ is independently chosen from C1–5 alkyl which may optionally be partially or fully halogenated and C1–2 alkoxy, which may optionally be partially or fully halogenated;

$R_3$ is hydrogen;

$R_4$ is chosen from hydrogen and methyl;

$R_8$ is chosen from hydrogen, methyl, ethyl, $CH_2OH$ and $CH_2OCH_3$.

6. The compound according to claim 5 wherein $R^a$ is chosen from hydrogen, C1–5 alkyl, C3–6 cycloalkyl, phenyl, C1–5 alkoxy, C1–5 alkoxycarbonyl, C1–3 acyloxy, C1–3 acylamino, hydroxyl and halogen.

7. The compound according to claim 6 wherein $Ar^1$ is

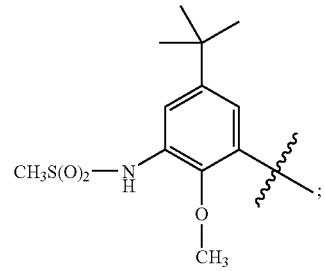

$R_5$ is —NH(CR$_7$R$_8$)$_n$—R$^a$, wherein $R^a$ is chosen from phenyl, cyclopropyl, cyclohexyl, C1–5 alkyl and C1–3 alkoxy.

8. A compound chosen from

1-[5-(3-Methanesulfonylamino-2-methoxy-5-trifluoromethyl-phenylcarbamoyl)-2-methyl-phenyl]-1H-1,2,3-triazole-4-carboxylic acid methyl ester 1-[5-(5-tert-Butyl-2-methoxy-phenylcarbamoyl)-2-methyl-phenyl]-1H-1,2,3-triazole-4-carboxylic acid ((R)-1-phenyl-ethyl)-amide 1-[5-(5-tert-Butyl-2-methoxy-phenylcarbamoyl)-2-methyl-phenyl]-1H-1,2,3-triazole-4-carboxylic acid benzylamide 1-[5-(5-tert-Butyl-2-methoxy-phenylcarbamoyl)-2-methyl-phenyl]-1H-1,2,3-triazole-4-carboxylic acid methyl ester 1-[3-(5-tert-Butyl-3-methanesulfonylamino-2-methoxy-phenylcarbamoyl)-phenyl]-1H-[1,2,3]triazole-4-carboxylic acid ((R)-1-phenyl-ethyl)-amide 1-[3-(5-tert-Butyl-3-methanesulfonylamino-2-methoxy-phenylcarbamoyl)-phenyl]-1H-[1,2,3]triazole-4-carboxylic acid benzylamide 1-[3-(5-tert-Butyl-3-methanesulfonylamino-2-methoxy-phenylcarbamoyl)-phenyl]-1H-[1,2,3]triazole-4-carboxylic acid (2,2-dimethyl-propyl)-amide 1-[5-(5-tert-Butyl-3-methanesulfonylamino-2-methoxy-phenylcarbamoyl)-2,3-dimethyl-phenyl]-1H-1,2,3-triazole-4-carboxylic acid benzylamide 1-[5-(5-tert-Butyl-3-methanesulfonylamino-2-methoxy-phenylcarbamoyl)-2,3-dimethyl-phenyl]-1H-1,2,3-triazole-4-carboxylic acid methyl ester 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-ethyl)-amide 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-propyl)-amide 1-[5-(5-tert-Butyl-3-methanesulfonylamino-2-methoxy-phenylcarbamoyl)-2-chloro-phenyl]-1H-1,2,3-triazole-4-carboxylic acid (2,2-dimethyl-propyl)-amide 1-[5-(5-tert-Butyl-3-methanesulfonylamino-2-methoxy-phenylcarbamoyl)-2-chloro-phenyl]-1H-1,2,3-triazole-4-carboxylic acid ethyl ester 1-[5-(5-tert-Butyl-3-methanesulfonylamino-2-methoxy-phenylcarbamoyl)-2-chloro-phenyl]-1H-1,2,3-triazole-4-carboxylic acid methyl ester 1-[5-(5-tert-Butyl-3-methanesulfonylamino-2-methoxy-phenylcarbamoyl)-2-fluoro-phenyl]-1H-[1,2,3]triazole-4-carboxylic acid benzylamide 1-[5-(5-tert-Butyl-3-methanesulfonylamino-2-methoxy-phenylcarbamoyl)-2-fluoro-phenyl]-1H-[1,2,3]triazole-4-carboxylic acid (2,2-dimethyl-propyl)-amide 1-[5-(5-tert-Butyl-3-methanesulfonylamino-2-methoxy-phenylcarbamoyl)-2-fluoro-2-methyl-phenyl]-1H-[1,2,3]triazole-4-carboxylic acid (2,2-dimethyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid 1-[5-(5-tert-Butyl-3-methanesulfonylamino-2-methoxy-phenylcarbamoyl)-2-methyl-phenyl]-1H-1,2,3-triazole-4-carboxylic acid ((R)-1,2,2-trimethyl-propyl)-amide 1-{5-[3-Methanesulfonylamino-2-methoxy-5-(2,2,2-trifluoro-1-trifluoromethyl-ethyl)-phenylcarbamoyl]-2-methyl-phenyl}-1H-[1,2,3]triazole-4-carboxylic acid ((R)-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((R)-1-cyclohexyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((R)-1-phenyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((S)-1,2,2-trimethyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((S)-1-cyclohexyl-ethyl)-amide 1-[5-(5-tert-Butyl-3-methanesulfonylamino-2-methoxy-phenylcarbamoyl)-2-methyl-phenyl]-1H-1,2,3-triazole-4-Carboxylic acid ((S)-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((S)-2-dimethylamino-1-phenyl-ethyl)-amide 1-[5-(5-tert-Butyl-3-methanesulfonylamino-2-methoxy-phenylcarbamoyl)-2-methyl-phenyl]-1H-[1,2,3]triazole-4-carboxylic acid ((R)-3-dimethylamino-1-phenyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((S)-2-methoxy-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid (1-methyl-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid (2,2-dimethyl-propyl)-amide 1-[5-(3-Amino-5-tert-butyl-2-methoxy-phenylcarbamoyl)-2-methyl-phenyl]-1H-[1,2,3]triazole-4-carboxylic acid (2,2-dimethyl-propyl)-amide 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid (2,2-dimethyl-propyl)-amide 1-[5-(5-tert-Butyl-3-methanesulfonylamino-2-methoxy-phenylcarbamoyl)-2-methyl-phenyl)-1H-1,2,3-triazole-4-carboxylic acid (2-dimethylamino-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid (2-hydroxy-2-methyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid (3-dimethylamino-2,2-dimethyl-propyl)-amide 1-[5-(5-tert-Butyl-3-methanesulfonylamino-2-methoxy-phenylcarbamoyl)-2-methyl-phenyl]-1H-[1,2,3]triazole-4-carboxylic acid (2-dimethylamino-2-methyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid 3-methyl-benzylamide 1-[5-(5-tert-Butyl-3-methanesulfonylamino-2-methoxy-phenylcarbamoyl)-2-methyl-phenyl]-1H-1,2,3-triazole-4-carboxylic acid amide 1-[5-(5-tert-Butyl-3-methanesulfonylamino-2-methoxy-phenylcarbamoyl)-2-methyl-phenyl]-1H-1,2,3-triazole-4-carboxylic acid benzylamide 1-[5-(5-tert-Butyl-3-methanesulfonylamino-2-methoxy-phenylcarbamoyl)-2-methyl-phenyl]-1H-[1,2,3]triazole-4-carboxylic acid phenylamide 1-[5-(5-tert-Butyl-3-methanesulfonylamino-2-methoxy-phenylcarbamoyl)-2-methyl-phenyl]-1H-[1,2,3]triazole-4-carboxylic acid phenylamide 1-[5-(5-tert-Butyl-3-methanesulfonylamino-2-methoxy-phenylcarbamoyl)-2-methyl-phenyl]-1H-[1,2,3]triazole-4-carboxylic acid phenylamide 1-[5-(5-tert-Butyl-3-methanesulfonylamino-2-methoxy-phenylcarbamoyl)-2-methyl-phenyl]-1H-[1,2,3]triazole-4-carboxylic acid o-tolylamide 1-[5-(5-tert-Butyl-3-methanesulfonylamino-2-methoxy-phenylcarbamoyl)-2-methyl-phenyl]-1H-1,2,3-triazole-4-carboxylic acid benzyl-methyl-amide 1-[5-(5-tert-Butyl-3-methanesulfonylamino-2-methoxy-phenylcarbamoyl)-2-methyl-phenyl]-1H-[1,2,3]triazole-4-carboxylic acid ((S)-2-dimethylamino-1-phenyl-ethyl)-methyl-amide 1-[5-(5-tert-Butyl-3-methanesulfonylamino-2-methoxy-phenylcarbamoyl)-2-methyl-phenyl]-1H-1,2,3-triazole-4-carboxylic acid cyclohexylmethyl-amide 1-[5-(5-tert-Butyl-3-methanesulfonylamino-2-methoxy-phenylcarbamoyl)-2-methyl-phenyl]-1H-1,2,3-triazole-4-carboxylic acid cyclopentylamide 1-[5-(5-tert-Butyl-3-methanesulfonylamino-2-methoxy-phenylcarbamoyl)-2-methyl-phenyl]-1H-1,2,3-triazole-4-carboxylic acid cyclopentylmethyl-amide 1-[5-(5-tert-Butyl-3-methanesulfonylamino-2-methoxy-phenylcarbamoyl)-2-methyl-phenyl]-1H-1,2,3-triazole-4-carboxylic acid cyclopropylamide 1-[5-(5-tert-Butyl-3-methanesulfonylamino-2-methoxy-phenylcarbamoyl)-2-methyl-phenyl]-1H-1,2,3-triazole-4-carboxylic acid cyclopropylmethyl-amide 1-[5-(5-tert-Butyl-3-methanesulfonylamino-2-methoxy-phenylcarbamoyl)-2-methyl-phenyl]-1H-1,2,3-triazole-4-carboxylic acid ethyl ester 1-[5-(5-tert-Butyl-3-methanesulfonylamino-2-methoxy-phenylcarbamoyl)-2-methyl-phenyl]-1H-1,2,3-triazole-4-carboxylic acid methyl ester 1-[5-(5-tert-Butyl-3-methanesulfonylamino-2-methoxy-phenylcarbamoyl)-2-methyl-phenyl]-1H-1,2,3-triazole-4-carboxylic acid methylamide 1-[5-(5-tert-Butyl-3-methanesulfonylamino-2-methoxy-phenylcarbamoyl)-2-methyl-phenyl]-1H-1,2,3-triazole-4-carboxylic acid tert-butylamide 1-{5-[3-Metanesulfonylamino-2-methoxy-5-(2,2,2-trifluoro-1-trifluoromethyl-ethyl)-phenylcarbamoyl]-2-methyl-phenyl}-1H-1,2,3-triazole-4-carboxylic acid ethyl ester 3-(4-Benzoyl-1,2,3-triazol-1-yl)-N-(5-tert-butyl-3-methanesulfonylamino-2-methoxy-phenyl)-4-methyl-benzamide 3-{1-[5-(5-tert-Butyl-3-methanesulfanylamino-2-methoxy-phenylcarbamoyl)-2-methyl-phenyl]-1H-1,2,3-triazole-4-carbonyl}-benzoic acid methyl ester 5-Amino-1-[5-(5-tert-butyl-3-methanesulfonylamino-2-methoxy-phenylcarbamoyl)-2-methyl-phenyl]-1H-1,2,3-triazole-4-carboxylic acid ((R)-1-phenyl-ethyl)-amide 5-Amino-1-[5-(5-tert-butyl-3-methanesulfonylamino-2-methoxy-phenylcarbamoyl)-2-methyl-phenyl]-1H-1,2,3-triazole-4-carboxylic acid (2,2-dimethyl-propyl)-amide 5-Amino-1-[5-(5-tert-butyl-3-methanesulfonylamino-2-methoxy-phenylcarbamoyl)-2-methyl-phenyl]-1H-[1,2,3]triazole-4-carboxylic acid ((S)-1,2,2-trimethyl-propyl)-amide 5-Amino-1-[5-(5-tert-butyl-3-methanesulfonylamino-2-methoxy-phenylcarbamoyl)-2-methyl-phenyl]-1H-[1,2,3]triazole-4-carboxylic acid (3-dimethylamino-2,2-dimethyl-propyl)-amide 5-Amino-1-[5-(5-tert-butyl-3-methanesulfonylamino-2-methoxy-phenylcarbamoyl)-2-methyl-phenyl]-1H-1,2,3-triazole-4-carboxylic acid methyl ester N-(5-tert-Butyl-3-methanesulfonylamino-2-methoxy-phenyl)-3-(4-cyclohexanecarbonyl-1,2,3-triazol-1-yl)-4-methyl-benzamide N-(5-tert-Butyl-3-methanesulfonylamino-2-methoxy-phenyl)-3-[4-((S)-3-hydroxy-2-phenyl-propionyl)-1,2,3-triazol-1-yl]-4-methyl-benzamide N-(5-tert-Butyl-3-methanesulfonylamino-2-methoxy-phenyl)-3-[4-(2,6-dichloro-benzoyl)-1,2,3-triazol-1-yl]-4-methyl-benzamide N-(5-tert-Butyl-3-methanesulfonylamino-2-methoxy-phenyl)-3-[4-(2,6-dimethyl-benzoyl)-1,2,3-triazol-1-yl]-4-methyl-benzamide N-(5-tert-Butyl-3-methanesulfonylamino-2-methoxy-phenyl)-4-methyl-3-[4-((R)-2-phenyl-propionyl)-1,2,3-triazol-1-yl]-benzamide and N-(5-tert-Butyl-3-methanesulfonylamino-2-methoxy-phenyl)-4-methyl-3-[4-(2-methyl-benzoyl)-1,2,3-triazol-1-yl]-benzamide or the pharmaceutically acceptable salts, acids, esters or isomers thereof.

9. A compound chosen from

1-[5-(5-tert-Butyl-2-methoxy-phenylcarbamoyl)-2-methyl-phenyl]-1H-1,2,3-triazole-4-carboxylic acid ((R)-1-phenyl-ethyl)-amide 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-ethyl)-amide 1-[5-(5-tert-Butyl-3-methanesulfonylamino-2-methoxy-phenylcarbamoyl)-2-chloro-phenyl]-1H-1,2,3-triazole-4-carboxylic acid ((R)-1-phenyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((R)-1,2,2-trimethyl-propyl)-amide 1-[5-(5-tert-Butyl-2-methoxy-phenylcarbamoyl)-2-methyl-phenyl]-1H-[1,2,3]triazole-4-carboxylic acid (2,2-dimethyl-propyl)-amide 1-{5-[3-Methanesulfonylamino-2-methoxy-5-(1-methyl-cyclopropyl)-phenylcarbamoyl]-2-methyl-phenyl}-1H-[1,2,3]triazole-4-carboxylic acid (2,2-dimethyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((R)-1-cyclohexyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((R)-1-phenyl-propyl)-amide 1-{5-[3-Methanesulfonylamino-2-methoxy-5-(2,2,2-trifluoro-1-trifluoromethyl-ethyl)-phenylcarbamoyl]-2-methyl-phenyl}-1H-[1,2,3]triazole-4-carboxylic acid ((R)-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid ((S)-2-methoxy-1-phenyl-ethyl)-amide 1-[5-(5-tert-Butyl-3-methanesulfonylamino-2-methoxy-phenylcarbamoyl)-2-methyl-phenyl]-1H-1,2,3-triazole-4-carboxylic acid (2-hydroxy-2-methyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid (3-dimethylamino-2,2-dimethyl-propyl)-amide 1-[5-(5-tert-Butyl-3-methanesulfonylamino-2-methoxy-phenylcarbamoyl)-2-methyl-phenyl]-1H-1,2,3-triazole-4-carboxylic acid cyclohexylmethyl-amide 1-[5-(5-tert-Butyl-3-methanesulfonylamino-2-methoxy-phenylcarbamoyl)-2-methyl-phenyl]-1H-1,2,3-triazole-4-carboxylic acid cyclopentylamide 1-[5-(5-tert-Butyl-3-methanesulfonylamino-2-methoxy-phenylcarbamoyl)-2-methyl-phenyl]-1H-1,2,3-triazole-4-carboxylic acid cyclopentylmethyl-amide 5-Amino-1-[5-(5-tert-butyl-3-methanesulfonylamino-2-methoxy-phenylcarbamoyl)-2-methyl-phenyl]-1H-1,2,3-triazole-4-carboxylic acid ((R)-1-phenyl-ethyl)-amide 5-Amino-1-[5-(5-tert-butyl-3-methanesulfonylamino-2-methoxy-phenylcarbamoyl)-2-methyl-phenyl]-1H-1,2,3-triazole-4-carboxylic acid (2,2-dimethyl-propyl)-amide 5-Amino-1-[5-(5-tert-butyl-3-methanesulfonylamino-2-methoxy-phenylcarbamoyl)-2-methyl-phenyl]-1H-1,2,3]triazole-4-carboxylic acid ((S)-1,2,2-trimethyl-propyl)-amide 5-Amino-1-[5-(5-tert-butyl-3-methanesulfonylamino-2-methoxy-phenylcarbamoyl)-2-methyl-phenyl]-1H-[1,2,3]triazole-4-carboxylic acid (3-dimethylamino-2,2-dimethyl-propyl)-amide 1-[5-(5-tert-Butyl-3-methanesulfonylamino-2-methoxy-phenylcarbamoyl)-2-methyl-phenyl]-1H-[1,2,3]triazole-4-carboxylic acid o-tolylamide N-(5-tert-Butyl-3-methanesulfonylamino-2-methoxy-phenyl)-3-(4-cyclohexanecarbonyl-1,2,3-triazol-1-yl)-4-methyl-benzamide N-(5-tert-Butyl-3-methanesulfonylamino-2-methoxy-phenyl)-3-[4-((S)-3-hydroxy-2-phenyl-propionyl)-1,2,3-triazol-1-yl]-4-methyl-benzamide N-(5-tert-Butyl-3-methanesulfonylamino-2-methoxy-phenyl)-4-methyl-3-[4-((R)-2-phenyl-propionyl)-1,2,3-triazol-1-yl]-benzamide and 1-[5-(5-tert-Butyl-3-methanesulfonylamino-2-methoxy-phenylcarbamoyl)-2-methyl-phenyl]-1H-1,2,3-triazole-4-carboxylic acid ((S)-2-dimethylamino-1-phenyl-ethyl)-amide or the pharmaceutically acceptable salts, acids, esters or isomers thereof.

10. A method of treating a disease or condition chosen from:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, diabetes, inflammatory bowel diseases, acute and chronic pain, stroke, myocardial infarction, thermal injury, adult respiratory distress syndrome (ARDS), multiple organ injury secondary to trauma, acute glomerulonephritis, dermatoses, acute purulent meningitis, necrotizing entrerocolitis, restenosis following percutaneous transluminal coronary angioplasty, sepsis, chronic obstructive pulmonary disease said method comprising administering to a patient a pharmaceutically effective amount of a compound according to claim 1.

11. A process of making a compound of the formula:

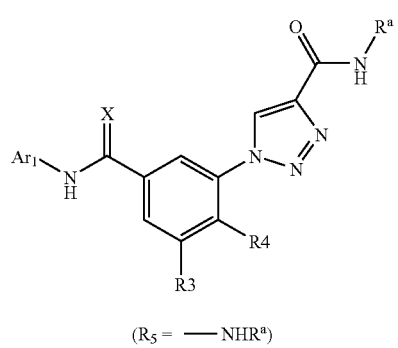

($R_5$ = —$NHR^a$)

wherein $Ar_1$, $R_3$, $R_4$ and $R^a$ are as defined in claim 1 and $H_5$ is —$NHR^a$;

said process comprising:

reacting a 3-aminobenzoic acid (II) with $NaNO_2$ in an aqueous acid at about 0° C.;

reacting the formed diazonium salt in situ with a cold aqueous solution of $NaN_3$ at about 0° C. to provide the azide III:

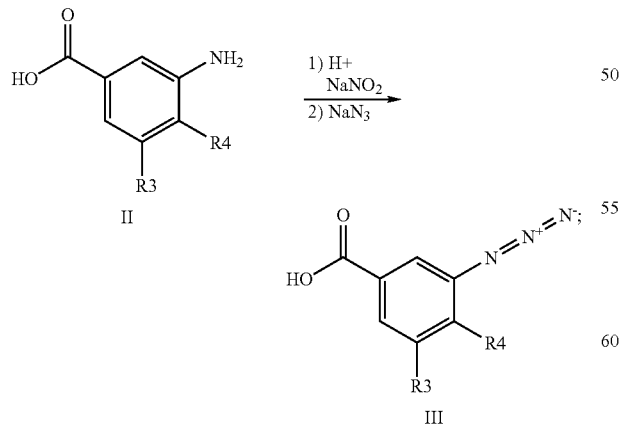

reacting the azide III with an alkyne ester IVa in a suitable solvent at about 100° C. to 120° C., or with a copper catalyst to provide triazole Va and its regioisomer:

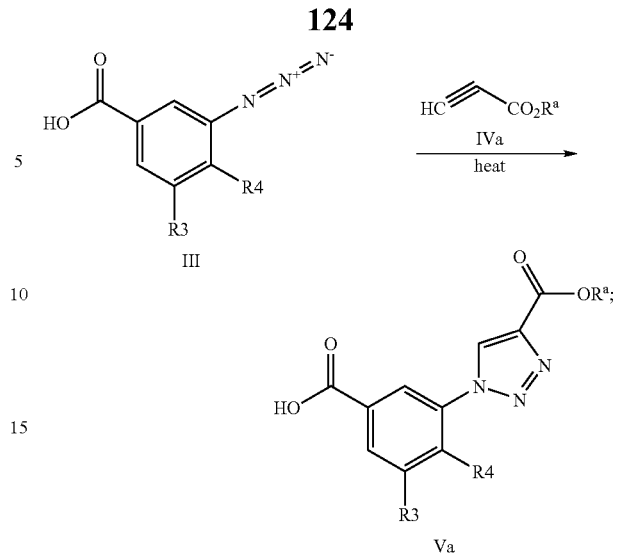

coupling under suitable conditions the intermediate Va and $Ar_1NH_2$ intermediate to produce the ester of formula I ($R_5$ is —$OR_2$):

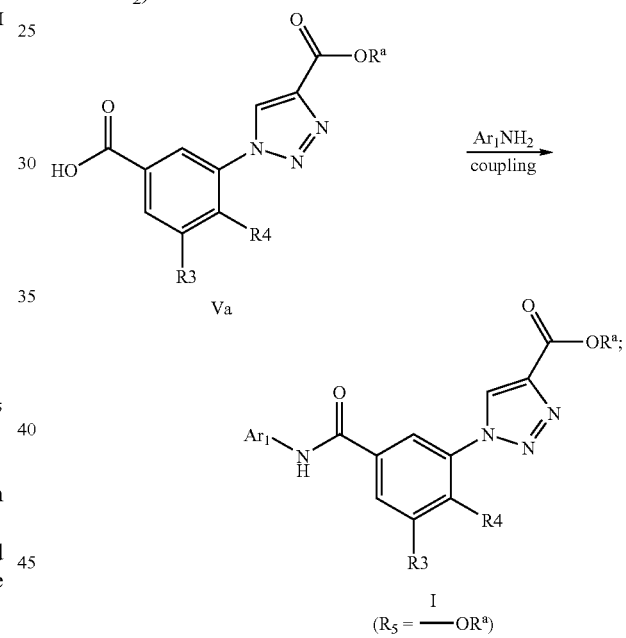

($R_5$ = —$OR^a$)

hydrolyzing the ester of formula I with aqueous base in a suitable solvent to provide the carboxylic acid of formula I ($R_5$=—OH):

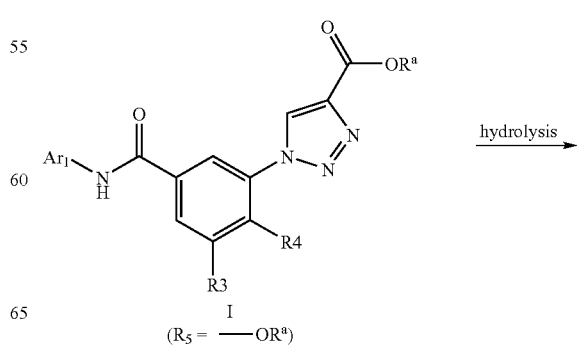

($R_5$ = —$OR^a$)

-continued

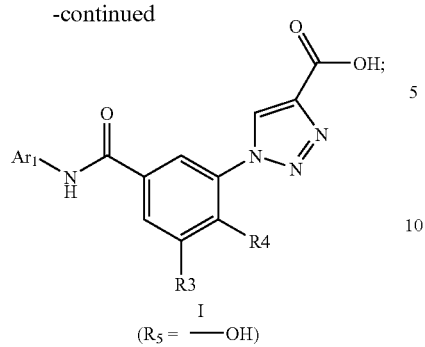

coupling the carboxylic acid of formula I with amine $R_aNH_2$ under suitable coupling conditions to provide the product compound of formula I ($R_5$=—NHR$^a$):

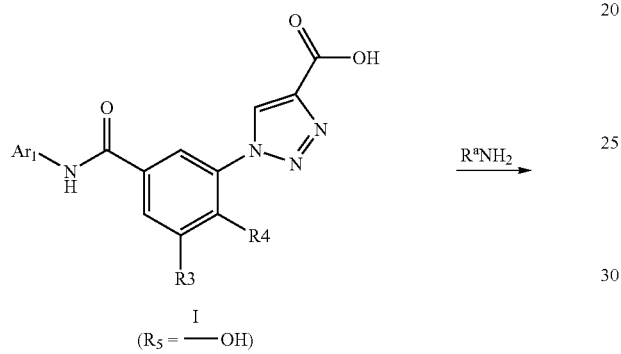

-continued

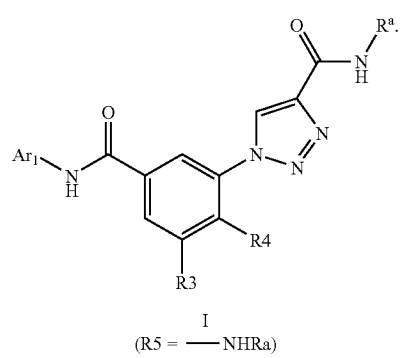

12. A pharmaceutical composition containing a pharmaceutically effective amount of a compound according to claim 1 and one or more pharmaceutically acceptable carriers and/or adjuvants.

13. The compound according to claim 5 and wherein:
$R^4$ is methyl;
$R^a$ is chosen from hydrogen, C1–5 alkyl, C3–6 cycloalkylC0–2 alkyl, phenyl, C1–5 alkoxy, amino, C1–5 alkylamino, C1–3 dialkylamino, C1–3 acyl, C1–5 alkoxycarbonyl, C1–3 acyloxy, C1–3 acylamino, hydroxyl and halogen.

* * * * *